US011413283B2

(12) United States Patent
Brown et al.

(10) Patent No.: US 11,413,283 B2
(45) Date of Patent: *Aug. 16, 2022

(54) TOPICAL FORMULATIONS FOR DELIVERY OF HEDGEHOG INHIBITOR COMPOUNDS AND USE THEREOF

(71) Applicant: PellePharm, Inc., Orinda, CA (US)

(72) Inventors: Marc Barry Brown, Watford (GB); Cameron Robert Stevenson, Guildford (GB); Charles Rodney Greenaway Evans, Worthing (GB)

(73) Assignee: PellePharm, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/878,301

(22) Filed: May 19, 2020

(65) Prior Publication Data

US 2020/0383975 A1 Dec. 10, 2020

Related U.S. Application Data

(60) Continuation of application No. 16/239,457, filed on Jan. 3, 2019, now Pat. No. 10,695,344, which is a division of application No. 15/173,257, filed on Jun. 3, 2016, now Pat. No. 10,369,147.

(60) Provisional application No. 62/275,185, filed on Jan. 5, 2016, provisional application No. 62/171,117, filed on Jun. 4, 2015.

(51) Int. Cl.
| | |
|---|---|
| *A61K 31/496* | (2006.01) |
| *A61K 9/00* | (2006.01) |
| *A61K 47/02* | (2006.01) |
| *A61K 47/08* | (2006.01) |
| *A61K 47/10* | (2017.01) |
| *A61K 47/12* | (2006.01) |
| *A61K 47/22* | (2006.01) |
| *A61K 9/06* | (2006.01) |
| *A61K 9/70* | (2006.01) |
| *A61K 31/4355* | (2006.01) |

(52) U.S. Cl.
CPC .......... *A61K 31/496* (2013.01); *A61K 9/0014* (2013.01); *A61K 9/06* (2013.01); *A61K 9/7084* (2013.01); *A61K 31/4355* (2013.01); *A61K 47/02* (2013.01); *A61K 47/08* (2013.01); *A61K 47/10* (2013.01); *A61K 47/12* (2013.01); *A61K 47/22* (2013.01)

(58) Field of Classification Search
CPC ........ A61K 31/496; A61K 9/00; A61K 47/02; A61K 47/08; A61K 47/10; A61K 47/12; A61K 47/22; A61K 9/06; A61K 9/7084; A61K 31/4355
See application file for complete search history.

(56) References Cited

U.S. PATENT DOCUMENTS

| | | | |
|---|---|---|---|
| 4,843,071 | A | 6/1989 | Hohenwarter |
| 4,968,787 | A | 11/1990 | Inada et al. |
| 5,086,047 | A | 2/1992 | Gourvest et al. |
| 5,169,780 | A | 12/1992 | Stirling et al. |
| 5,378,475 | A | 1/1995 | Smith et al. |
| 5,767,161 | A | 6/1998 | Stroppolo et al. |
| 6,177,407 | B1 | 1/2001 | Rodgers et al. |
| 6,184,381 | B1 | 2/2001 | Ikariya et al. |
| 6,238,876 | B1 | 5/2001 | Altaba |
| 6,291,516 | B1 | 9/2001 | Dudek et al. |
| 6,372,931 | B1 | 4/2002 | Blacker et al. |
| 6,432,970 | B2 | 8/2002 | Beachy et al. |
| 6,509,467 | B1 | 1/2003 | Blacker et al. |
| 6,545,188 | B2 | 4/2003 | Blacker et al. |
| 6,552,016 | B1 | 4/2003 | Baxter et al. |
| 6,613,798 | B1 | 9/2003 | Porter et al. |
| 6,686,388 | B2 | 2/2004 | Dudek et al. |
| 6,867,216 | B1 | 3/2005 | Beachy et al. |
| 6,887,820 | B1 | 5/2005 | Ikariya et al. |
| 6,909,003 | B2 | 6/2005 | Storz |
| 7,098,196 | B1 | 8/2006 | Beachy et al. |
| 7,112,690 | B2 | 9/2006 | Chi et al. |

(Continued)

FOREIGN PATENT DOCUMENTS

| | | |
|---|---|---|
| CN | 102085176 A | 6/2011 |
| EP | 0255331 A2 | 2/1988 |

(Continued)

OTHER PUBLICATIONS

Aboulkassim et al., "Alteration of the PATCHED locus in superficial bladder cancer", Oncogene, vol. 22, No. 19, pp. 2967-2971 (2003).

(Continued)

*Primary Examiner* — Shirley V Gembeh
(74) *Attorney, Agent, or Firm* — McDermott Will & Emery LLP; Judy M. Mohr; Brennen P. Baylor

(57) ABSTRACT

Compositions for topical administration of a hedgehog inhibitor compound are described. In one embodiment, the hedgehog inhibitor compound is patidegib and the topical composition comprises the compound in a solvent system of a monohydric primary alcohol and a polyol in a w/w ratio of between about 0.9-1.8. In another embodiment, the hedgehog inhibitor is itraconazole and the topical composition comprises the compound in a solvent system comprising a monohydric primary alcohol and an optionally lower alkyl end-capped oligomeric alkylene glycol in a w/w ratio of between about 0.8 and 2.6 and a fused bicyclic ether. Method of using the compositions are also described, where in one embodiment, the compositions are topically applied for treating or preventing basal cell carcinoma.

21 Claims, 8 Drawing Sheets

(56) References Cited

U.S. PATENT DOCUMENTS

| | | |
|---|---|---|
| 7,230,004 B2 | 6/2007 | Adams et al. |
| 7,250,526 B2 | 7/2007 | Blacker et al. |
| 7,291,626 B1 | 11/2007 | Beachy et al. |
| 7,407,967 B2 | 8/2008 | Adams et al. |
| 7,476,661 B2 | 1/2009 | Beachy et al. |
| 7,541,183 B2 | 6/2009 | Rudnicki et al. |
| 7,605,167 B2 | 10/2009 | Tas et al. |
| 7,629,352 B2 | 12/2009 | Tas et al. |
| 7,648,994 B2 | 1/2010 | Castro et al. |
| 7,655,674 B2 | 2/2010 | Beachy et al. |
| 7,812,164 B2 | 10/2010 | Austad et al. |
| 7,867,492 B2 | 1/2011 | Beachy et al. |
| 7,875,628 B2 | 1/2011 | Adams et al. |
| 7,893,078 B2 | 2/2011 | Tas et al. |
| 7,928,133 B2 | 4/2011 | Cheng et al. |
| 7,964,590 B2 | 6/2011 | Castro et al. |
| 7,994,191 B2 | 8/2011 | Castro et al. |
| 8,017,648 B2 | 9/2011 | Castro et al. |
| 8,063,043 B2 | 11/2011 | Bajwa et al. |
| 8,227,509 B2 | 7/2012 | Castro et al. |
| 8,236,956 B2 | 8/2012 | Adams et al. |
| 8,293,760 B2 | 10/2012 | Castro et al. |
| 8,426,436 B2 | 4/2013 | Castro et al. |
| 8,431,566 B2 | 4/2013 | Castro et al. |
| 8,481,542 B2 | 7/2013 | He et al. |
| 8,669,365 B2 | 3/2014 | Austad et al. |
| 8,703,448 B2 | 4/2014 | Austad et al. |
| 8,716,479 B2 | 5/2014 | Austad et al. |
| 8,722,672 B2 | 5/2014 | Fritze et al. |
| 8,785,635 B2 | 7/2014 | Austad et al. |
| 8,895,576 B2 | 11/2014 | Castro et al. |
| 9,000,023 B2 | 4/2015 | Hipskind et al. |
| 9,145,422 B2 | 9/2015 | Castro et al. |
| 9,238,672 B2 | 1/2016 | Austad et al. |
| 9,376,447 B2 | 6/2016 | Genov et al. |
| 9,394,313 B2 | 7/2016 | Genov et al. |
| 9,409,871 B2 | 8/2016 | He et al. |
| 9,492,435 B2 | 11/2016 | Austad et al. |
| 9,669,011 B2 | 6/2017 | Castro et al. |
| 9,879,025 B2 | 1/2018 | Genov et al. |
| 9,879,293 B2 | 1/2018 | Austad et al. |
| 9,951,083 B2 | 8/2018 | Austad et al. |
| 10,045,970 B2 | 8/2018 | Castro et al. |
| 10,314,827 B2 | 6/2019 | Castro et al. |
| 10,369,147 B2 | 8/2019 | Brown et al. |
| 10,406,139 B2 | 9/2019 | Austad et al. |
| 2002/0006931 A1 | 1/2002 | Beachy et al. |
| 2002/0087258 A1 | 7/2002 | Johnson |
| 2002/0193347 A1 | 12/2002 | Bulliard et al. |
| 2003/0114393 A1 | 6/2003 | Liscovitch et al. |
| 2003/0162870 A1 | 8/2003 | Kimura et al. |
| 2003/0175355 A1 | 9/2003 | Tobyn et al. |
| 2003/0220314 A1 | 11/2003 | Shackleton et al. |
| 2004/0023949 A1 | 2/2004 | Baxter et al. |
| 2004/0072913 A1 | 4/2004 | Tas et al. |
| 2004/0072914 A1 | 4/2004 | Tas et al. |
| 2004/0073404 A1 | 4/2004 | Brooks et al. |
| 2004/0110663 A1 | 6/2004 | Dudek et al. |
| 2004/0126359 A1 | 7/2004 | Lamb et al. |
| 2004/0127474 A1 | 7/2004 | Dudek et al. |
| 2004/0247643 A1 | 12/2004 | Martinod et al. |
| 2005/0049218 A1 | 3/2005 | Gilbertson |
| 2005/0112707 A1 | 5/2005 | Altaba et al. |
| 2005/0203061 A1 | 9/2005 | Yamashita et al. |
| 2006/0020020 A1 | 1/2006 | Dudek et al. |
| 2006/0074030 A1 | 4/2006 | Adams et al. |
| 2006/0094660 A1 | 5/2006 | Thomson |
| 2006/0128639 A1 | 6/2006 | Beachy |
| 2006/0142245 A1 | 6/2006 | Beachy et al. |
| 2006/0252073 A1 | 11/2006 | Yilmaz et al. |
| 2007/0003550 A1 | 1/2007 | Antonia et al. |
| 2007/0009530 A1 | 1/2007 | Altaba et al. |
| 2007/0021493 A1 | 1/2007 | Guicherit et al. |
| 2007/0036800 A1 | 2/2007 | Bergstein |
| 2007/0060546 A1 | 3/2007 | Ruat et al. |
| 2007/0179091 A1 | 8/2007 | De Sauvage et al. |
| 2007/0191410 A1 | 8/2007 | Adams et al. |
| 2007/0219250 A1 | 9/2007 | Singh et al. |
| 2007/0231828 A1 | 10/2007 | Beachy et al. |
| 2007/0281040 A1 | 12/2007 | Weichselbaum et al. |
| 2008/0019961 A1 | 1/2008 | Wicha et al. |
| 2008/0057071 A1 | 3/2008 | Watkins et al. |
| 2008/0058298 A1 | 3/2008 | Beachy et al. |
| 2008/0089915 A1 | 4/2008 | Tas et al. |
| 2008/0095761 A1 | 4/2008 | Beachy et al. |
| 2008/0107749 A1 | 5/2008 | Maitra et al. |
| 2008/0118493 A1 | 5/2008 | Beachy et al. |
| 2008/0138379 A1 | 6/2008 | Jennings-Spring |
| 2008/0182859 A1 | 7/2008 | Brunton et al. |
| 2008/0255059 A1 | 10/2008 | Beachy et al. |
| 2008/0262051 A1 | 10/2008 | Balkovec et al. |
| 2008/0269182 A1 | 10/2008 | Pluda et al. |
| 2008/0269272 A1 | 10/2008 | Adams et al. |
| 2008/0287420 A1 | 11/2008 | Castro et al. |
| 2008/0293754 A1 | 11/2008 | Austad et al. |
| 2008/0293755 A1 | 11/2008 | Castro et al. |
| 2009/0004257 A1 | 1/2009 | Venkatraman et al. |
| 2009/0012109 A1 | 1/2009 | Austad et al. |
| 2009/0041680 A1 | 2/2009 | Tamarkin et al. |
| 2009/0181997 A1 | 7/2009 | Grayzel et al. |
| 2009/0203713 A1 | 8/2009 | Beachy et al. |
| 2009/0208579 A1 | 8/2009 | Ueki et al. |
| 2009/0216022 A1 | 8/2009 | Austad et al. |
| 2009/0246841 A1 | 10/2009 | Jamieson et al. |
| 2009/0263317 A1 | 10/2009 | Chen et al. |
| 2009/0286822 A1 | 11/2009 | Tas et al. |
| 2009/0305338 A1 | 12/2009 | Ritala-Nurmi et al. |
| 2010/0003728 A1 | 1/2010 | Jayatilake et al. |
| 2010/0093625 A1 | 4/2010 | Tarasova et al. |
| 2010/0099116 A1 | 4/2010 | Faia et al. |
| 2010/0144775 A1 | 6/2010 | Castro et al. |
| 2010/0210515 A1 | 8/2010 | Nash et al. |
| 2010/0222287 A1 | 9/2010 | McGovern et al. |
| 2010/0273818 A1 | 10/2010 | Beachy et al. |
| 2010/0286114 A1 | 11/2010 | Thomas et al. |
| 2010/0286180 A1 | 11/2010 | Castro et al. |
| 2010/0297118 A1 | 11/2010 | MacDougall et al. |
| 2010/0311748 A1 | 12/2010 | Dakin et al. |
| 2011/0009442 A1 | 1/2011 | Austad et al. |
| 2011/0034498 A1 | 2/2011 | McGovern et al. |
| 2011/0104254 A1 | 5/2011 | Tas et al. |
| 2011/0135739 A1 | 6/2011 | Carter et al. |
| 2011/0166353 A1 | 7/2011 | Adams et al. |
| 2011/0183948 A1 | 7/2011 | Levine et al. |
| 2011/0230509 A1 | 9/2011 | Castro et al. |
| 2012/0010229 A1 | 1/2012 | MacDougall et al. |
| 2012/0010230 A1 | 1/2012 | MacDougall et al. |
| 2012/0015934 A1 | 1/2012 | Castro et al. |
| 2012/0065218 A1 | 3/2012 | Castro et al. |
| 2012/0065399 A1 | 3/2012 | Genov et al. |
| 2012/0065400 A1 | 3/2012 | Genov et al. |
| 2012/0077834 A1 | 3/2012 | Castro et al. |
| 2012/0083484 A1 | 4/2012 | Castro et al. |
| 2012/0083607 A1 | 4/2012 | Austad et al. |
| 2012/0190742 A1 | 7/2012 | Silver |
| 2012/0214810 A1 | 8/2012 | Bajwa et al. |
| 2013/0102614 A1 | 4/2013 | Liu et al. |
| 2013/0108582 A1 | 5/2013 | Castro et al. |
| 2013/0108583 A1 | 5/2013 | Castro et al. |
| 2013/0109700 A1 | 5/2013 | Epstein, Jr. et al. |
| 2013/0143831 A1 | 6/2013 | Embil et al. |
| 2014/0107142 A1 | 4/2014 | Castro et al. |
| 2014/0357868 A1 | 12/2014 | Austad et al. |
| 2014/0371253 A1 | 12/2014 | Austad et al. |
| 2014/0371456 A1 | 12/2014 | Austad et al. |
| 2015/0025012 A1 | 1/2015 | MacDougall et al. |
| 2016/0158208 A1 | 6/2016 | Castro et al. |
| 2016/0168193 A1 | 6/2016 | Jayatilake et al. |
| 2016/0177354 A1 | 6/2016 | Austad et al. |
| 2016/0354368 A1 | 12/2016 | Brown et al. |
| 2017/0022212 A1 | 1/2017 | Austad et al. |
| 2017/0029433 A1 | 2/2017 | Genov et al. |
| 2017/0174703 A1 | 7/2017 | Wu et al. |
| 2017/0231968 A1 | 8/2017 | Epstein |

(56) References Cited

U.S. PATENT DOCUMENTS

| | | |
|---|---|---|
| 2017/0360763 A1 | 12/2017 | Castro et al. |
| 2018/0338962 A1 | 11/2018 | Castro et al. |
| 2019/0134027 A1 | 5/2019 | Brown et al. |
| 2019/0000816 A1 | 6/2019 | Austad et al. |
| 2019/0263852 A1 | 8/2019 | Jayatilake et al. |
| 2020/0022962 A1 | 1/2020 | Castro et al. |

FOREIGN PATENT DOCUMENTS

| | | |
|---|---|---|
| EP | 0388188 A1 | 9/1990 |
| EP | 0434570 A2 | 6/1991 |
| EP | 1401438 B1 | 9/2005 |
| EP | 2225254 A2 | 9/2010 |
| EP | 2443926 A2 | 4/2012 |
| JP | 2010-0514796 A | 5/2010 |
| WO | WO 1994/020520 A1 | 9/1994 |
| WO | WO 1995/018856 A1 | 7/1995 |
| WO | WO 1996/017924 A2 | 6/1996 |
| WO | WO 1997/013518 A1 | 4/1997 |
| WO | WO 1999/049835 A1 | 10/1999 |
| WO | WO 2000/018708 A1 | 4/2000 |
| WO | WO 2000/041545 A2 | 7/2000 |
| WO | WO 2001/009077 A1 | 2/2001 |
| WO | WO 2001/019800 A2 | 3/2001 |
| WO | WO 2001/026644 A2 | 4/2001 |
| WO | WO 2001/027135 A3 | 4/2001 |
| WO | WO 2001/049279 A2 | 7/2001 |
| WO | WO 2001/074344 A2 | 10/2001 |
| WO | WO 2001/090077 A1 | 11/2001 |
| WO | WO 2002/030462 A2 | 4/2002 |
| WO | WO 2002/078703 A1 | 10/2002 |
| WO | WO 2002/078704 A1 | 10/2002 |
| WO | WO 2003/011219 A2 | 2/2003 |
| WO | WO 2003/088964 A1 | 10/2003 |
| WO | WO 2003/088970 A2 | 10/2003 |
| WO | WO 2004/020599 A2 | 3/2004 |
| WO | WO 2004/058976 A1 | 7/2004 |
| WO | WO 2005/013800 A2 | 2/2005 |
| WO | WO 2005/032343 A2 | 4/2005 |
| WO | WO 2005/033288 A2 | 4/2005 |
| WO | WO 2005/042700 A2 | 5/2005 |
| WO | WO 2006/026430 A1 | 3/2006 |
| WO | WO 2006/028958 A2 | 3/2006 |
| WO | WO 2006/050351 A2 | 5/2006 |
| WO | WO 2006/078283 A2 | 7/2006 |
| WO | WO 2007/053596 A1 | 5/2007 |
| WO | WO 2007/054623 A2 | 5/2007 |
| WO | WO 2007/059157 A1 | 5/2007 |
| WO | WO 2007/093372 A1 | 8/2007 |
| WO | WO 2007/120827 A2 | 10/2007 |
| WO | WO 2007/123511 A2 | 11/2007 |
| WO | WO 2007/131201 A2 | 11/2007 |
| WO | WO 2008/011071 A1 | 1/2008 |
| WO | WO 2008/037732 A1 | 4/2008 |
| WO | WO 2008/063165 A1 | 5/2008 |
| WO | WO 2008/070357 A2 | 6/2008 |
| WO | WO 2008/083248 A2 | 7/2008 |
| WO | WO 2008/083252 A2 | 7/2008 |
| WO | WO 2008/089123 A2 | 7/2008 |
| WO | WO 2008/109184 A1 | 9/2008 |
| WO | WO 2008/109829 A1 | 9/2008 |
| WO | WO 2008/110611 A1 | 9/2008 |
| WO | WO 2008/112913 A1 | 9/2008 |
| WO | WO 2008/131354 A2 | 10/2008 |
| WO | WO 2009/086416 A1 | 7/2009 |
| WO | WO 2009/086451 A1 | 7/2009 |
| WO | WO 2009/099625 A2 | 8/2009 |
| WO | WO 2009/126840 A1 | 10/2009 |
| WO | WO 2010/000070 A1 | 1/2010 |
| WO | WO 2010/002970 A2 | 1/2010 |
| WO | WO 2010/085654 A1 | 7/2010 |
| WO | WO 2011/017551 A1 | 2/2011 |
| WO | WO 2011/041075 A1 | 4/2011 |
| WO | WO 2011/057222 A1 | 5/2011 |
| WO | WO 2011/063309 A1 | 5/2011 |
| WO | WO 2012/006584 A2 | 1/2012 |
| WO | WO 2012/006589 A2 | 1/2012 |
| WO | WO 2012/037217 A1 | 3/2012 |
| WO | WO 2013/049332 A1 | 4/2013 |
| WO | WO 2014/093871 A1 | 6/2014 |

OTHER PUBLICATIONS

Ahlford, "Asymmetric transfer hydrogenation of ketones, catalyst development and mechanistic investigation", Department of Organic Chemistry, Stockholm University, US-AB Stockholm, pp. 1-49 (2011).

Ailles and Siu, "Targeting the hedgehog pathway in cancer: can the spines be smoothened?", Clin. Cancer Res.; vol. 17, No. 8, pp. 2071-2073 (2011).

Alexandre et al., "Transcriptional activation of hedgehog target genes in *Drosophila* is mediated directly by the Cubitus interruptus protein, a member of the GLI family of zinc finger DNA-bindInq proteins", Genes Dev., vol. 10, pp. 2003-2013 (1996).

Alonso et al., "Ru(arene)(amino alcohol)-catalyzed transfer hydrogenation of ketones: mechanism and origin of enantioselectivity", J. Am. Chem. Soc., vol. 121, pp. 9580-9588 (1999).

Athar et al., "Hedgehog signaling in skin development and cancer", Exp. Dermatol., vol. 15, No. 9, pp. 667-677 (2006).

Bailey et al., "Sonic hedgehog promotes desmoplasia in pancreatic cancer", Clin. Cancer Res., vol. 14, No. 19, pp. 5995-6004 (2008).

Bailey et al., "Sonic hedgehog paracrine signaling regulates metastasis and lymphangiogenesis in pancreatic cancer", Oncogene, vol. 28, No. 40, pp. 3513-3525 (2009).

Bale and Yu, "The hedgehog pathway and basal cell carcinomas", Human Molecular Genetics, vol. 10, No. 7, pp. 757-762 (2001).

Banerjee et al., "Recruitment of the sonic hedgehog signalling cascade in electroconvulsive seizure-mediated regulation of adult rat hippocampal neurogenesis", Eur. J. Neurosci., vol. 22, No. 7, pp. 1570-1580 (2005).

Bar et al., "Cyclopamine-mediated hedgehog pathway inhibition depletes stem-like cancer cells in glioblastoma", Stem Cells, vol. 25, No. 10, pp. 2524-2533 (2007).

Barken et al., "Noscapine inhibits human prostate cancer progression and metastasis in a mouse model," Anticancer Res., vol. 28, No. 6A, pp. 3701-3704 (2008).

Belloni et al., "Identification of Sonic hedgehog as a candidate gene responsible for holoprosencephaly", Nature Genetics, vol. 14, pp. 353-356 (1996).

Berge et al., "Pharmaceutical salts", J. Pharm. Sci., 66, No. 1, pp. 1-19 (1977).

Berger et al., "Regulator of G-protein signaling-5 induction in pericytes coincides with active vessel remodeling during neovascularization," Blood, vol. 105, No. 3, pp. 1094-1101 (2005).

Berman et al., "Medulloblastoma growth inhibition by hedgehog pathway blockade", Science, vol. 297, pp. 1559-1561 (2002).

Berman et al., "Widespread requirement for Hedgehog ligand stimulation in growth of digestive tract tumours", Nature, vol. 425, pp. 846-851 (2003).

Bhat et al., "Synthesis and biological evaluation of novel steroidal pyrazoles as substrates for bile acid transporters", Bioorg. Med. Chem. Lett., vol. 15, pp. 85-87 (2005).

Bhattacharya et al., "Role of Hedgehog signaling in ovarian cancer", Clin. Cancer Res., vol. 14, No. 23, pp. 7659-7666 (2008).

Biospace, Print News Article, "Infinity Pharmaceuticals, Inc. Announces Hedgehog Pathway Inhibitor Agreement with AstraZeneca PLC (AZN)", Cambridge, Mass., Nov. 12, 2007, (Prime Newswire), 2 pages, Retreived from the internet: http://www.biospace.com/news_story.aspx?NewsEntityId=77067.

Brown and Keeler, "Structure-activity relation of steroid teratogens, 1. Jervine ring system", J. Agric. Food Chem., vol. 26, No. 3, pp. 561-563 (1978).

Brown and Keeler, "Structure-activity relation of steroid teratogens, 2. N-substituted jervines", J. Agric. Food Chem., vol. 26, No. 3, pp. 564-566 (1978).

(56) References Cited

OTHER PUBLICATIONS

Browne et al., "Isolation of teratogenic alkaloids by reversed-phase high-performance liquid chromatography" Journal of Chromatography Biomedical Applications, vol. 336, pp. 211-220 (1984).

Business Wire, "Infinity Reports Update from Phase 2 Study of Saridegib Plus Gemcitabine in Patients with Metastatic Pancreatic Cancer", Infinity Pharmaceuticals, 3 pages, Jan. 27, 2012, Retreived from the internet: http://www.businesswire.com/news/home/20120127005146/en/Infinity-Reports-Update-Phase-2-Study-Saridegib#.U3Us_IdV8E.

Campbell et al., "Direct Targeting of the Hedgehog pathway in primary chondrosarcoma xenografts with smoothened Inhibitor IPI-926", Infinity Pharmaceuticals, Inc., Presentation Poster, Abstract #LB380, 1 page (2011).

Cancer Cluster Salzburg, "CCS researchers identify imiquimod as novel Hedgehog pathway inhibitor in skin cancer", Apr. 29, 2014, retrieved form the internet: URL: http://www.cancercluster-salzberg.at/#!CCS-researchers-identify-imiquimod-as-novel-Hedgehog-pathway-inhibitor-in-skin-cancer/axycm/5687b39c0cf23a10fe3c91fc, accessed on Sep. 28, 2016.

Carter et al., "Formulation for IPI-926 drug product, a novel oral Hedgehog pathway inhibitor in clinical development", Infinity Pharmaceuticals, Inc., Presentation Poster, Abstract #M1169, with Presentation Abstract, 2 pages (2009).

Caserta et al., "p63 overexpression induces the expression of sonic hedgehog", Mol. Cancer Res., vol. 4, No. 10, pp. 759-768 (2006).

Chaumeil, "Micronization: A method of improving the bioavailability of poorly soluble drugs", Methods Find. Exp. Clin. Pharmacol., vol. 20, No. 3, pp. 211-215 (1998).

Chen et al., "Inhibition of Hedgehog signaling by direct binding of cyclopamine to smoothened", Genes Dev., vol. 16, No. 21, pp. 2743-2748 (2002).

Chen et al., "Small molecule modulation of Smoothened activity", PNAS, vol. 99, No. 22, pp. 14071-14076 (2002).

Chen et al., "Targeting the hedgehog pathway to mitigate treatment resistance", Cell Cycle, vol. 6, Issue. 15, pp. 1826-1830 (2007).

Chen et al., "Sonic hedgehog dependent phosphorylation by CK1α and GRK2 is required for ciliary accumulation and activation of smoothened", PloS Biology, vol. 9, Issue. 6, No. e1001083, 16 pages (2011).

Christiansen et al., "Antiandrogenic steroidal sulfonylpyrazoles", J. Med. Chem., vol. 33, pp. 2094-2100 (1990).

Chung et al., "New targets for therapy in prostate cancer: modulation of stromal-epithelial interactions", Urology, vol. 62, Suppl. 5A, pp. 44-54 (2003).

Clement et al., "HEDGEHOG-GLI1 signaling regulates human glioma growth, cancer stem cell self-renewal and tumorigenicity", Curr. Biol., vol. 17, No. 2, pp. 165-172 (2007).

Clinton et al., "Steroidal heterocycles, VI. Formulation of A/B-cis 3-Ketosteroids. Preparation of 5β-Steroidal[3,2-c]pyrazoles", J. Org. Chem., vol. 27, pp. 2800-2807 (1962).

COMTEX, "Infinity announces hedgehog pathway inhibitor agreement with AstraZeneca", Infinity Pharmaceuticals, PrimeWireNewswire via COMTEX News Network, 2 pages, Nov. 12, 2007, Retrieved from the internet: http://files.shareholder.com/downloads/INFI/0x0x144355/71ecb752-43b2-4a26-9867-8feea13ee93d/INFI_News_2007_11_12_General.pdf.

Cong et al., "Steroidal alkaloids from the roots and rhizomes of *Veratrum nigrum* L", Helvetica Chimica Acta, vol. 90, Issue 5, pp. 1038-1042 (2007).

Cooper et al., "Teratogen-mediated inhibition of target tissue response to Shh signaling", Science, vol. 280, pp. 1603-1607 (1998).

Corbit et al., "Vertebrate smoothened functions at the primary cilium", Nature, vol. 437 No. 7061, pp. 1018-1021 (2005).

Cutcliffe et al., "Clear cell sarcoma of the kidney: Up-regulation of neural markers with activation of the sonic hedgehog and Akt pathways", Clin. Cancer Res., vol. 11, No. 22, pp. 7986-7994 (2005).

Dakhova et al., "Global gene expression analysis of reactive stroma in prostate cancer", Clin. Cancer Res., vol. 15, No. 12, pp. 3979-3989 (2009).

Deng et al., "External preparation useful for preparing drug for treating infectious disease caused by fungi, comprises nanosized itraconazole and matrix", Database WPI, Thomson Scientific, London, GB, AN: 2011-H84807, PN: CN102085176, 4 pgs. (2011) Abstract.

Dersnah and Baird, "Chiral $\eta^6$-$C_6H_6$ ruthehium complexes", J. Org. Chem., vol. 127, C55-C58 (1977).

Dierks et al., "Essential role of stromally induced hedgehog signaling in B-cell malignancies", Nat. Med., vol. 13, No. 8, pp. 944-951 (2007) Pre Publication Article, DOI:10.1038/nm1614 pp. 1-8 (2007).

Dierks et al., "Expansion of Bcr-Abl-positive leukemic stem cells is dependent on Hedgehog pathway activation", Cancer Cell, vol. 14, No. 3, pp. 238-249 (2008).

Di Magliano and Hebrok, "Hedgehog signalling in cancer formation and maintenance", Nat. Rev., vol. 3, No. 12, pp. 903-911 (2003).

Djerassi and Gutzwiller, "Selective reduction of steroids by homogeneous catalytic hydrogenation", J. Am. Chem. Soc., vol. 88, No. 19, pp. 4537-4538 (1966).

Dormeyer et al., "Plasma membrane proteomics of human embryonic stem cells and human embryonal carcinoma cells", J. Proteome Res., vol. 7, No. 7, pp. 2936-2951 (2008).

Dörwald, "Side reactions in organic synthesis, a guide to successful synthesis design", Wiley-VCH, Verlag GmbH & Co. KGaA, Weinheim, ISBN:3-527-31021-5, p. IX of Preface and pp. 8-13 (2005).

Ehtesham et al., "Ligand-dependent activation of the hedgehog pathway in glioma progenitor cells", Oncogene, vol. 26, No. 39, pp. 5752-5761 (2007).

Engelman and Settleman, "Acquired resistance to tyrosine kinase inhibitors during cancer therapy", Curr, Opin. Genet. Dev., vol. 18, No. 1, pp. 73-79 (2008).

Everaere et al., "Ruthenium (II)-catalyzed asymmetric transfer hydrogenation of carbonyl compounds with 2-propanol and ephedrine-type ligands", Adv. Synth. Catal., vol. 345, No. 1&2, pp. 67-77 (2003).

Fahrenholtz et al., "Cycloprop[16α, 17α] androstanes", J. Med. Chem., vol. 15, No. 10, pp. 1056-1060 (1972).

Faia et al., "Depilation induced anagen as a model to study hedgehog pathway antagonist IPI-926: Implications for biomarker development", AACR Meeting Abstracts Online, Abstract #2827, with Infinity Pharmaceuticals Poster, 3 pages (2008).

Fan et al., "Hedgehog singaling promotes prostate xenograft tumor growth", Endocrinology, vol. 145, No. 8, pp. 3961-3970 (2004).

Feldmann et al., "Blockade of hedgehog signaling inhibits pancreatic cancer invasion and metastases: A new paradigm for combination therapy in solid cancers", Cancer Res., vol. 67, No. 5, pp. 2187-2196 (2007).

Feldmann et al., "An orally bioavailable small-molecule inhibitor of Hedgehog signaling inhibits tumor initiation and metastasis in pancreatic cancer", Mol. Cancer Ther., vol. 7, No. 9, pp. 2725-2735 (2008).

Furio et al., "Transgenic kallikrein 5 mice reproduce major cutaneous and systemic hallmarks of Netherton syndrome", J. Exp. Med., vol. 211, No. 3, pp. 499-513 (2014).

Geng et al., "Hedgehog signaling in the murine melanoma microenvironment", Angiogenesis, vol. 10, No. 4, pp. 259-267, DOI: 10.1007/s10456-007-9078-9 (2007).

Genov and Ager, "Asymmetric hydrogenation of ketones catalyzed by $Ru^{II}$-bicp complexes", Angew. Chem. Int. Ed. Engl., vol. 43, No. 21, pp. 2816-2819 (2004).

Giannis et al., "Synthesis of cyclopamine using a biomimetic and diastereoselective approach", Angew. Chem. Int. Ed., vol. 48, pp. 1-5 (2009).

Goldberg et al., "Resolution of odontogenic keratocysts of the jaw in basal cell nevus syndrome with GDC-0449", Arch Dematol., vol. 147, No. 7, pp. 839-841 (2011).

Green, "A new approach to the formal classification of covalent compounds of the elements", Journal of Organometallic Chemistry, vol. 500, Issue 1-2, pp. 127-148 (1995).

(56) References Cited

OTHER PUBLICATIONS

Grogan et al., "Synthesis and structure activity relationship of D-homo cyclopamine analogs: A-ring fused heterocyclic analogs", MEDI 97, 237th ACS National Meeting, Infinity Pharmaceuticals, Inc., Presentation Poster, with Presentation Abstract, 2 pgs. (2009).
Growdon et al., "Hedgehog pathway inhibitor cyclopamine suppresses Gli1 expression and inhibits serous ovarian cancer xenograft growth", 40th Annual Meeting on Women's Cancer, Feb. 5-8, 2009, Presentation Slides, 16 pages (2009).
"Guidance for industry: Clinical trial endpoints for the approval of cancer drugs and biologics", US Dept. of Health Services, FDA, CDER and CBER, Section III, p. 4-9 (2007).
Guijarro et al., "Achiral β-amino alcohols as efficient ligands for the ruthenium-catalysed asymmetric transfer hydrogenation of sulfinylimines", Tetrahedron Letters, vol. 52, Issue 7, pp. 789-791 (2011), pre-publication accepted manuscript, DOI:10.1016/j.tetlet. 2010.12.031, 6 pgs. (2010).
Hald et al., "Evidence-based Danish guidelines for the treatment of Malassezia-related skin diseases", Acta Derm. Venereol., vol. 95, No. 1, pp. 12-19 (2015).
Hanahan et al., "Less is more, regularly: metronomic dosing of cytotoxic drugs can target tumor angiogenesis in mice", J. Clin. Inv., vol. 105, No. 8, pp. 1045-1047 (2000).
Harrington et al., "Targeted radiosensitisation by pegylated liposome-encapsulated 3', 5'-O-dipalmitoyl 5-iodo-2'-deoxyuridine in a head and neck cancer xenograft model," Br. J. Cancer, vol. 91, No. 2, pp. 366-373 (2004).
Harris et al., "Hedgehog signaling: Networking to nurture a premalignant tumor microenvironment", Mol. Cancer Res., vol. 9, No. 9, pp. 1165-1174 (2011).
Hashiguchi et al., "Asymmetric transfer hydrogenation of aromatic ketones catalyzed by chiral ruthenium (II) complexes", J. Am. Chem. Soc., vol. 117, No. 28, pp. 7562-7563 (1995).
Hashimoto, "Simmons-Smith reaction without hydroxyl groups", Chemical, vol. 61, No. 1, pp. 63-64 (2006) Japanese language with English translation.
Hawley's Condensed Chemical Dictionary, 15th edition, Lewis, ed., John Wiley & Sons, New York, pp. 38 and 100 (2007).
Heftmann, "Recent progress in the biochemistry of plant steroids other than steroids (saponins, glycoalkaloids, pregnane derivatives, cardiac glycosides, and sex hormones)", Lipids, vol. 9, No. 8, pp. 626-639 (1974).
Hegde et al., "Hedgehog-induced survival of B-cell chronic lymphocytic leukemia cells in a stromal cell microenvironment: a potential new therapeutic target", Mol. Cancer Res., vol. 6, No. 12, pp. 1928-1936 (2008).
Heretsch et al., "Cyclopamine and hedgehog signaling: chemistry, biology, medical perspectives", Angew. Chem. Int. Ed., vol. 49, pp. 2-12, DOI: 10.1002/anie.200906967 (2010).
Holton and Necoechea, "Steroids. CLXXV. Further steroidal anabolic agents", J. Med. Chem., pp. 1352-1357 (1962).
Huangfu et al., "Hedgehog signalling in the mouse requires intraflagellar transport proteins", Nature, vol. 426, No. 6962, pp. 83-87 (2003).
Ikariya et al., "Bifunctional transition metal-based molecular catalysts for asymmetric syntheses", Org. Biomol. Chem., vol. 4, No. 3, pp. 393-406 (2006).
Incardona et al., "Cyclopamine inhibition of sonic hedgehog signal transduction is not mediated through effects on cholesterol transport", Dev. Biol., vol. 224, No. 2, pp. 440-452 (2000).
International Search Report from International Patent Application No. PCT/US2005/030406, 2 pages, dated Apr. 4, 2006, application now published as International Patent Publication No. WO2006/026430 dated Mar. 9, 2006.
International Search Report from International Patent Application No. PCT/US2006/010796, 9 pages, dated May 15, 2008.
International Search Report from International Patent Application No. PCT/US2007/088990, 2 pages, dated Aug. 1, 2008.
International Search Report from International Patent Application No. PCT/US2007/088995, 6 pages, dated Aug. 1, 2008.
International Search Report from International Patent Application No. PCT/US2008/003200, 3 pages, dated Aug. 11, 2008.
International Search Report from International Patent Application No. PCT/US2008/050970, 3 pages, dated Aug. 22, 2008.
International Search Report from International Patent Application No. PCT/US2008/056229, 4 pages, dated Aug. 11, 2008.
International Search Report from International Patent Application No. PCT/US2008/088222, 6 pages, dated Feb. 23, 2009.
International Search Report from International Patent Application No. PCT/US2008/088302, 1 pages, dated Mar. 25, 2009.
International Search Report from International Patent Application No. PCT/US2009/049372, 3 pages, dated Mar. 16, 2010.
International Search Report from International Patent Application No. PCT/US2010/021816, 3 pages, dated Jun. 2, 2010.
International Search Report from International Patent Application No. PCT/US2010/044597, 2 pages, dated Oct. 1, 2010.
International Search Report from International Patent Application No. PCT/US2010/055879, 12 pages, dated Jan. 24, 2011.
International Search Report from International Patent Application No. PCT/US2010/057534, 2 pages, dated Jan. 18, 2011.
International Search Report from International Patent Application No. PCT/US2011/043446, 5 pages, dated Oct. 16, 2012.
International Search Report from International Patent Application No. PCT/US2011/043453, 4 pages, dated Mar. 14, 2012.
International Search Report from International Patent Application No. PCT/US2011/051553, 2 pages, dated Feb. 2, 2012.
International Search Report from International Patent Application No. PCT/US2016/035713, 8 pages, dated Nov. 9, 2016.
International Search Report from International Patent Application No. PCT/US2017/017247, 7 pages, dated Apr. 25, 2017.
Iselin et al., "Structure of jervine, VI. The sulfuric acid-catalyzed acetolysis of N-acetyl-3-deoxy-3 alpha.-chlorotetrahydro jervine", J. Am. Chem. Soc., vol. 76, pp. 5616-5620 (1954) Database Accession No. 1955:73589, XP-002672119, 4 pgs. (1954).
Iselin et al., "Jervine, IX. Miscellaneous new derivatives", J. Am. Chem. Soc., vol. 78, No. 2, pp. 403-407 (1956) Database Accession No. 1956:69487, XP-002672116. 3 pgs. (1956).
Jacobs and Craig, "The veratrine alkaloids, XXII. On pseudojervine and veratrosine, a companion glycoside in veratrum viride", J. Biol. Chem., vol. 155, 565-572 (1944).
Jacobs and Craig, "The veratrine alkaloids, XXV. The alkaloids of veratrum viride", J. Biol. Chem., vol. 160, pp. 555-565 (1945).
Jacobs and Huebner, "Veratrine alkaloids, XXVII. Further studies with jervine", J. Biol. Chem., vol. 170, pp. 635-652 (1947).
James et al., "Biomedical applications of poisonous plant research", J. Agric. Food Chem., vol. 52, pp. 3211-3230 (2004).
Ji et al., "Protein kinase A, not EPAC, suppresses hedgehog activity and regulates glucocorticoid sensitivity in acute lymphoblastic leukemia cells", J. Biol. Chem., vol. 282, No. 52, pp. 37370-37377 (2007).
Jiang et al., "Solution type spray of animycotic medicine for external application and its preparation method", Database WPI, Thomson Scientific, London, GB, AN: 2003-258153, PN: CN1380060, 4 pgs. (2002) Abstract.
Kaneko et al., "Biosynthesis of C-nor-D-homo-steroidal alkaloids from acetate-I-$^{14}$C, cholesterol-4-$^{14}$C and cholesterol-26-$^{14}$C in veratrum grandiflorum", Phytochemistry, vol. 9, pp. 2489-2495 (1970).
Kaneko et al., "11-deoxojervine as a precursor for jervine biosynthesis in veratrum grandiflorum", Phytochemistry, vol. 9, pp. 2497-2501 (1970).
Kaneko et al., "Conversion of solanidine to jervatrum alkaloids in veratrum grandiflorum", Phytochemistry, vol. 11, pp. 3199-3202 (1972).
Kaneko et al., "Biosynthesis of rubijervine in veratrum grandiflorum" Phytochemistry, vol. 14, pp. 1295-1301 (1975).
Kaneko et al., "Origin of nitrogen in the biosynthesis of solanidine by veratrum grandiflorum", Phytochemistry, vol. 15, pp. 1391-1393 (1976).
Kaneko et al., "Dormantinol, a possible precursor in solanidine biosynthesis from budding veratrum grandiflorum" Phytochemistry, vol. 16, pp. 1247-1251 (1977).

(56) References Cited

OTHER PUBLICATIONS

Karhadker et al., "Hedgehog signalling in prostate regeneration, neoplasia and metastasis", Nature, 431, pp. 707-712 (2004).

Kasutani et al., "Anti-IL-31 receptor antibody is shown to be a potential therapeutic option for treating itch and dermatitis in mice", British J. Pharmacol., vol. 171, No. 22, pp. 5049-5058 (2014).

Kaulmann et al., "Substrate spectrum of ω-transaminase from Chromobacterium violaceum DSM30191 and its potential for biocatalysis", Enzyme and Microbial Technology, vol. 41, Issue 5, pp. 628-637 (2007).

Kayed et al., "Distribution of indian hedgehog and its receptors patched and smoothened in human chronic pancreatitis". J. Endocrinol., vol. 178, No. 3, pp. 467-478 (2003).

Kayed et al., "Indian hedgehog signaling pathway: expression and regulation in pancreatic cancer", Int. J. Cancer; vol. 110, No. 5, pp. 668-676 (2004).

Keeler and Binns, "Chemical compounds of veratrum californicum related to congenital ovine cyclopian malformations: extraction of active material", Proc. Soc. Exptl. Biol. Med., vol. 116, pp. 123-127 (1964).

Keeler and Binns, "Teratogenic compounds of veratrum californicum (Durand), I. Preparation and characterization of fractions and alkaloids for biologic testing", Canadian Journal of Biochemistry, vol. 44, No. 6, pp. 819-828 (1966).

Keeler and Binns, "Teratogenic compounds of veratrum californicum (Durand), II. Production of ovine fetal cyclopia by fractions and alkaloid preparations", Can. J. Biochem., vol. 44, pp. 829-838 (1966).

Keeler, "Teratogenic compounds of veratrum californicum (Durand), IV. First isolation of veratramine and alkaloid Q and a reliable method for isolation of cyclopamine", Phytochemistry, vol. 7, pp. 303-306 (1968).

Keeler, "Toxic and teratogenic alkaloids of western range plants", J. Agr. Food Chem., vol. 17, No. 3, pp. 473-482 (1969).

Keeler, "Teratogenic Compounds of Veratrum Californicum (Durand) VII. The Structure of the glycosidic alkaloid cycloposine", Steroids, vol. 13, No. 5, pp. 579-588 (1969).

Keeler and Binns, "Teratogenic compounds of veratrum californicum as a function of plant part, stage, and site of growth", Phytochemistry, vol. 10, pp. 1765-1769 (1971).

Keeler, "Isolation of rubijervine from veratrum-californicum", Phytochemistry, vol. 13, pp. 2336-2337 (1974).

Keeler and Baker, "Oral, osmotic minipump, and intramuscular administration to sheep of the veratrum alkaloid cyclopamine (42970)", Cyclopamine Administration to Sheep, P.S.E.B.M., vol. 192, pp. 153-156 (1989).

Kenney et al., "Hedgehog and PI-3 kinase signaling converge on Nmyc1 to promote cell cycle progression in cerebellar neuronal precursors", Development, vol. 131, No. 1, pp. 217-228 (2004).

Kerbel and Kamen, "The anti-angiogenic basis of metronomic chemotherapy", Nature Rev., Cancer, vol. 4, pp. 423-436 (2004).

King, "Roughening up smoothened: chemical modulators of hedgehog signaling", J. Biol., vol. 1, No. 8, pp. 8.1-8.4 (2002).

Kitajima et al., "Steroid alkaloids of fresh bulbs of fritillaria thunbergii miq. and of crude drug "BAI-MO" prepared therefrom", Heterocycles, vol. 15, No. 2, pp. 791-796 (1981).

Koszelewski et al., "Formal asymmetric biocatalytic reductive amination", Angew. Chem. Int. Ed., vol. 47, No. 48, pp. 9337-9340 (2008).

Koszelewski et al., "ω-transaminases for the synthesis of non-racemic α-chiral primary amines", Trends Biotechnol., vol. 28, No. 6, pp. 324-332 (2010).

Kubo et al., "Hedgehog signaling pathway is a new therapeutic target for patients with breast cancer", Cancer Research, vol. 64, pp. 6071-6074 (2004).

Lacasse et al., "Iodomethylzinc phosphates: powerful reagents for the cyclopropanation of alkenes", J. Am. Chem. Soc., vol. 127, No. 36, pp. 12440-12441 (2005).

Lee et al., "Development of an enzyme-linked immunosorbent assay for the veratrum plant teratogens: cyclopamine and jervine", J. Agric. Food Chem., vol. 51, No. 3, pp. 582-586 (2003).

Leontjev et al., "Reduction of steroidal ketones with amine-boranes", Russian Chemical Bulletin, vol. 53, No. 3, pp. 703-708 (2004).

Lescarbeau et al., "Synthesis and structure activity relationship of D-homo cyclopamine hedgehog antagonists: 7-membered A-ring lactam analogs", MEDI 98, 237$^{th}$ ACS National Meeting, Infinity Pharmaceuticals, Inc., Poster, with Presentation Abstract, 2 pgs. (2009).

Lewis and Veltmaat, "Next stop, the twilight zone: hedgehog network regulation of mammary gland development", J. Mamm. Gland Biol. Neopl., vol. 9, No. 2, pp. 165-181 (2004).

Li et al., "Chemistry, bioactivity and geographical diversity of steroidal alkaloids from the Liliaceae family", Natural Product Reports, vol. 23, pp. 735-752 (2006).

Li et al., "Mesodermal deletion of transforming growth factor-β receptor II disrupts lung epithelial morphogenesis: cross-talk between TGF-β and sonic hedgehog pathways", J. Biol. Chem., vol. 283, No. 52, pp. 36257-36264 (2008).

Lin et al., "Self-renewal of acute lymphocytic leukemia cells is limited by the hedgehog pathway inhibitors cyclopamine and IPI-926", PLoS One, vol. 5, Issue 12, No. e15262, pp. 1-8 (2010).

Lindemann, "Stroma-initiated hedgehog signaling takes center stage in B-cell lymphoma", Cancer Res., vol. 68, No. 4, pp. 961-964 (2008).

Lipinski et al., "Dose- and route-dependent teratogenicity, toxicity, and pharmacokinetic profiles of the hedgehog signaling antagonist cyclopamine in the mouse", Toxicol. Sci. Advanced Access Publication, 28 pages, (2008).

Ma et al., "Frequent activation of the hedgehog pathway in advanced gastric adenocarcinomas", Carcinogenesis, vol. 26, No. 10, pp. 1698-1705 (2005).

Ma et al., "Study of sonic hedgehog signaling pathway related molecules in gastric carcinoma", World J. Gastroenterol., vol. 12, No. 25, pp. 3965-3969 (2006).

Ma et al., "Development of in vitro techniques for the important medicinal plant *Veratrum californicum*", Planta Medica, vol. 72, pp. 1142-1148 (2006).

Mandley et al., "The Hh inhibitor IPI-926 delays tumor re-growth of a non-small cell lung cancer xenograft model following treatment with an EGFR targeted tyrosine kinase inhibitor", Infinity Pharmaceuticals, Inc., Presentation Poster, Abstract #5045, 1 page (2010).

Manna et al., "Metabolite identification of IPI-609, a novel and potent inhibitor of the hedgehog pathway, in different species", Infinity Pharmaceuticals, Inc., Presentation Poster, 1 page (2008).

Mao et al., "First example of asymmetric transfer hydrogenation in water induced by a chiral amino alcohol hydrochloride", Tetrahedron Letters, vol. 46, pp. 7341-7344 (2005).

Masamune et al., "11-Deoxojervine, a new alkaloid form *Veratrum* species", Bull. Chem. Soc. Japan, vol. 38, No. 8, pp. 1374-1378 (1965).

Masamune et al., "Syntheses and NMR spectra of 22,27-imino-17,23-oxidojervane derivatives", Tetrahedron, vol. 23, No. 4, pp. 1591-1612 (1967).

Masamune et al., "Synthesis of jervine and related alkaloids", J, Am. Chem. Soc., vol. 89, No. 17, pp. 4521-4523 (1967).

Masumane et al., "The stereochemistry of dihydrojervine and related compounds: The ORD curves of 11-oxoetiojervanes and 11-oxoiminojervanes", Tetrahedron, vol. 25, Issue 19, pp. 4853-4871 (1969).

Mazur, "Azasteroids III. 3-aza-a-homo androgens", J. Org. Chem., vol. 28, pp. 248-250 (1963).

Meloni et al., "Smoothened signal transduction is promoted by G protein-coupled receptor kinase 2", Mol. Cell. Biol., vol. 26, No. 20, pp. 7550-7560 (2006).

Metcalfe and De Sauvage, "Hedgehog fights back: mechanisms of acquired resistance against smoothened antagonists", Cancer Res; vol. 71, No. 15, pp. 5057-5061 and 6087 (2011).

Mrozik et al., "Heterocyclic steroids in the antiinflammatory series", J. Med. Chem., vol. 7, pp. 584-589 (1964).

(56) References Cited

OTHER PUBLICATIONS

Müller-Röver et al., A comprehensive guide for the accurate classification of murine hair follicles in distinct hair cycle stages, J. Invest. Dermatol., vol. 117, No. 1, pp. 3-15 (2001).
Nakamura et al., "Induction of osteogenic differentiation by hedgehog proteins", Biochem. Biophys. Res. Comm., vol. 237, pp. 465-469 Article No. RC977156 (1997).
Niemann et al., "Indian hedgehog and β-catenin signaling: Role in the sebaceous lineage of normal and neoplastic mammalian epidermis". PNAS, vol. 100, Suppl. 1, pp. 11873-11880 (2003).
Nolan-Stevaux et al., "GLI1 is regulated through smoothened-independent mechanisms in neoplastic pancreatic ducts and mediates PDAC cell survival and transformation", Genes Dev., vol. 23, No. 1, pp. 24-36 (2009).
Noyori and Hashiguchi, "Asymmetric transfer hydrogenation catalyzed by chiral ruthenium complexes", Acc. Chem. Res., vol. 30, No. 2, pp. 97-102 (1997).
Oatis et al., "Isolation, purification and full NMR assignments to cyclopamine from veratrum californicum", Chemistry Central Journal, vol. 2, No. 12, 17 pgs. (2008).
Ohta et al., "Investigations on steroids. XI. Synthesis of steroidal oxazole, imidazole, and triazole", Chem. Pharm. Bull. vol. 16, No. 8, pp. 1487-1497 (1968).
Ohta et al., "p53-independent negative regulation of p21/cyclin-dependent kinase-interacting protein 1 by the sonic hedgehog-glioma-associated oncogene 1 pathway in gastric carcinoma Cells", Cancer Res., vol. 65, No. 23, pp. 10822-10829 (2005).
Oka and Hara, "Regiospecific Beckmann rearrangement of 3-oxo-4-ene steroid oximes", J. Org. Chem., vol. 43, No. 19, pp. 3790-3791 (1978).
Oka and Hara, "Synthesis of A-azasteroids by the use of specific Beckmann rearrangement", Chemistry and Industry, pp. 168-170 (1969).
Olive et al., "Inhibition of hedgehog signaling enhances delivery of chemotherapy in a mouse model of pancreatic cancer", Science, vol. 324, No. 5933, pp. 1457-1461 (2009).
Oro and Higgins, "Hair cycle regulation of hedgehog signal reception", Dev. Biol., vol. 255, No. 2, pp. 238-248 (2003).
Paladini et al., "Modulation of hair growth with small molecule agonists of the hedgehog signaling pathway", J. Invest. Dermatol., vol. 125, No. 4, pp. 638-646 (2005).
Pan et al., "Discovery of NVP-LDE225, a potent and selective smoothened antagonist", ACS Med. Chem. Lett., vol. 1, No. 3, pp. 130-134 (2010).
Park and Park, "Differential expression of Runx2 and indian hedgehog in cartilaginous tumors", Pathol. Oncol. Res., vol. 13, No. 1, pp. 32-37 (2007).
Park et al., "Composition useful for treating skin fungal infections, comprises itraconazole, phenol and phenolic alcohol", Database WPI, Thomson Scientific, London, GB, AN: 2010-F87592, PN: KR20100051293, 4 pgs. (2010) Abstract.
Park et al., "A crucial requirement for hedgehog signaling in small cell lung cancer", Nature Med., Author manuscript, vol. 17, No. 11, pp. 1504-1508, DOI: 10.1038/nm.2473 (2012).
Paryzek et al., "Ammonium formate/palladium on carbon: A versatile system for catalytic hydrogen transfer reductions of carbon-carbon double bonds", Synthesis, No. 13, pp. 2023-2026 (2003).
Patil et al., "Hedgehog signaling in human hepatocellular carcinoma", Cancer Biol. Ther., vol. 5, No. 1, pp. 111-117 (2006).
Peacock et al., "Hedgehog signaling maintains a tumor stem cell compartment in multiple myeloma", PNAS USA, vol. 104, No. 10, pp. 4048-4053 (2007).
Peacock et al., "Visualization of SMOOTHENED activation supports an essential role for hedgehog signaling in the regulation of self-renewal in small cell lung cancer", Infinity Pharmaceuticals, Inc., 1 page (2009).
Peluso et al., "Impact of the Smoothened inhibitor, IPI-926, on smoothened ciliary localization and Hedgehog pathway activity", PLOS ONE, vol. 9, Issue 3, No. e90534, 11 pages (2014).

Penova and Trandafiloff, "Intensification of extraction processes with tensides", Pharmazie, vol. 26, No. 8, pp. 489-490 (1971) With English Translation.
Philips et al., "Hedgehog signaling antagonist promotes regression of both liver fibrosis and hepatocellular carcinoma in a murine model of primary liver cancer", PLoS One, vol. 6, Issue 9, No. e23943, pp. 1-12 (2011).
Pietsch et al., "Medulloblastomas of the desmoplastic variant carry mutations of the human homologue of *Drosophila* patched", Cancer Research, vol. 57, pp. 2085-2088 (1997).
Pink et al., "Activity of IPI-926, a potent HH pathway inhibitor, in a novel model of medulloblastoma derived from Ptch/HIC +/− mice", Infinity Pharmaceuticals, Inc., AACR Meeting Abstracts Online, 99th AACR Annual Meeting, Apr. 13, 2008; San Diego, CA, Abstract #1588, Presentation Slides, 15 pages (2008).
Proctor et al., "Hedgehog signaling in castration resistant prostate cancer", AACR Annual Meeting, Apr. 17-21, 2010, Infinity Pharmaceuticals, Inc., Abstract #3857, Presentation Slides, 14 pages (2010).
Qualthrough et al., "Hedgehog signalling in colorectal tumour cells: induction of apoptosis with cyclopamine treatment" Int. J. Cancer, vol. 110, No. 6, pp. 831-837 (2004).
Quirk et al., "The smoothened gene and hedgehog signal transduction in *Drosophila* and vertebrate development", Cold Spring Harbor Symposium Quant. Biol., vol. 62, pp. 217-226 (1997).
Rahman et al., "Alkaloids from veratrum album", Phytochemistry, vol. 30, No. 1, pp. 368-370 (1991).
Rahman and Choudhary, "Chemistry and biology of steroidal alkaloids", The Alkaloids, Cordell, ed., Academic Press, San Diego, vol. 50, Ch. 2, pp. 61-108 (1998).
Rasmusson et al., "Azasteroids: structure-activity relationships for inhibition of 5α-reductase and of androgen receptor binding", J. Med. Chem., vol. 29, pp. 2298-2315 (1986).
Ravasio and Rossi, "Selective hydrogenations promoted by copper catalysts. 1. Chemoselectivity, regioselectivity, and stereoselectivity in the hydrogenation of 3-substituted steroids", J. Org. Chem., vol. 56, No. 13, pp. 4329-4333 (1991).
Read, "Direct targeting of tumor cells with smoothed inhibitor IPI-926", 2011 AACR Read IPI-926 Direct Targeting, Infinity Pharmaceuticals, Inc., Presentation Slides, 27 pages (2011).
Reddy et al., "A new novel and practical one pot methodology for conversion of alchohols to amines", Synthetic Communications, vol. 30, No. 12, pp. 2233-2237 (2000).
Reetz and Li, "An efficient catalyst system for the asymmetric transfer hydrogenation of ketones: remarkably broad substrate scope", J. Am. Chem. Soc., vol. 128, No. 4, pp. 1044-1045 (2006).
Reifenberger et al., "Missense mutations in SMOH in sporadic basal cell carcinomas of the skin and primitive neuroectodermal tumors of the central nervous system", Cancer Research, vol. 58, pp. 1798-1803 (1998).
Remingtons Pharmaceutical Sciences, 17$^{th}$ Edition, Gennaro, ed., Mack Publishing Company, Easton, Pennsylvania 18042, p. 1625 (1985).
Rohatgi et al., "Patched1 regulates hedgehog signaling at the primary cilium", Science, vol. 317, No. 5836, pp. 372-376 (2007).
Rominger et al., "Evidence for allosteric interactions of antagonist binding to the smoothened receptor", J. Pharmacol. Exp. Ther., vol. 329, No. 3, pp. 995-1005 (2009).
Ross, "A Study Evaluating IPI-926 in combination with gemcitabine in patients with metastatic pancreatic cancer", National Cancer Institute, Clinical Trials (PDQ ®), Data processed on Oct. 17, 2013, 3 pgs., Retrieved from the internet http://www.cancer.gov/clinicaltrials/search/view?cdrid=674592&version=HealthProfessional.
Rubin and De Sauvage, "Targeting the hedgehog pathway in cancer", Nature Rev., vol. 5, No. 12, pp. 1026-1033 (2006).
Rudin et al., "Treatment of medulloblastoma with hedgehog pathway inhibitor GDC-0449", N. Eng. J. Med., vol. 361, No. 12, pp. 1173-1178 (2009).
Rudin et al., "A phase 1 study of IPI-926, an inhibitor of the hedgehog pathway, in patients with advanced or metastatic solid tumors", Infinity Pharmaceuticals, Inc., Poster, 1 page. (2010).
Saldanha, "The hedgehog signalling pathway and cancer", J. Pathol., vol. 193, No. 4, pp. 427-432 (2001).

(56) References Cited

OTHER PUBLICATIONS

Samukawa et al., "Red ginseng inhibits scratching behavior associated with atopic dermatitis in experimental animal models", J. Pharmacol. Sci., vol. 118, No. 3, pp. 391-400 (2012).
Sanganwar and Gupta, "Dissolution-rate enhancement of fenofibrate by adsorption onto silica using supercritical carbon dioxide", Int. J. Pharm., vol. 360, No. 1-2, pp. 213-218 (2008).
Sasson et al., "Homogeneous catalytic transfer-hydrogenation of a, β-unsaturated carbonyl compounds by dichlorotris (triphenylphosphine) ruthenium (II)", Tetrahedron Letters, vol. 12, Issue. 24, pp. 2167-2170 (1971).
Sato et al., "Induction of the hair growth phase in postnatal mice by localized transient expression of Sonic hedgehog", J. Clin. Invest., vol. 104, No. 7, pp. 855-864 (1999).
Sato et al., "Effect of adenovirus-mediated expression of sonic hedgehog gene on hair regrowth in mice with chemotherapy-induced alopecia", J. Natl. Cancer Inst., vol. 93, No. 24, pp. 1858-1864 (2001).
Sawada et al., "Asymmetric catalysis of intramolecular cyclopropanation of 5-aryl-1-diazo-1-mesitylsulfonyl-5-hexen-2-ones", Adv. Synth. Catal., vol. 347, Issue 11-13, pp. 1527-1532 (2005).
Shafaee et al., "Cyclopamine increases the cytotoxic effects of paclitaxel and radiation but not cisplatin and gemcitabine in hedgehog expressing pancreatic cancer cells", Cancer Chemother. Pharmacol., vol. 58, No. 6, pp. 765-770 (2006), Original Article, 6 pgs., DOI:10.1007/s00280-006-0227-4 (2006).
Shafiee et al., "Enzymatic deglycosylation of enfumafungin, a triterpene glycoside natural product, and its chemically synthesized analogues", J. Mol. Catalysis B: Enzymatic, vol. 16, pp. 27-32 (2001).
Shaw et al., "The sonic hedgehog pathway stimulates prostate tumor growth by paracrine signaling and recapitulates embryonic gene expression in tumor myofibroblasts", Oncogene, vol. 28, No. 50, pp. 4480-4490 (2009).
Sheng et al., "Activation of the hedgehog pathway in advanced prostate cancer", Molecular Cancer, vol. 3, No. 29, 13 pages (2004).
Sheng et al., "Regulation of Gli1 localization by the cAMP/protein kinase A signaling axis through a site near the nuclear localization signal", J. Biol. Chem. vol. 281, No. 1, pp. 9-12 (2006).
Shibasaki et al., "Hydrolysis of conjugated steroids by the combined use of β-glucuronidase preparations from Helix pomatia and Ampullaria: Determination of urinary cortisol and its metabolites", Steroids, vol. 66, pp. 795-801 (2001).
Shin et al., "Hedgehog / WNT feedback supports regenerative proliferation of epithelial stem cells in bladder", Nature, vol. 472, No. 7341, pp. 110-114, Author Manuscript, 15 pgs. (2011).
Shiotani et al., "Sonic hedgehog and CDX2 expression in the stomach", J. Gastroenterol. Hepatol., vol. 23, Suppl. 2, pp. S161-S166 (2008).
Shner et al., "The sterospecificity of the hydrogenation of 16α-methyl-3-oxo-$\Delta^4$-unsaturated compounds", Chemistry of Natural Compounds, vol. 6, No. 1 , pp. 48-51 (1970).
Shroff and Harper, "3-Aza-A-homoandrostenes" J. Med. Chem., vol. 12, No. 1, pp. 190-191 (1969).
Sicklick et al., "Hedgehog signaling correlates with hepatocellular carcinoma progression" J. Clinical Oncology, 2005 ASCO Annual Meeting Proceedings, vol. 23, No. 16s (Jun. 1 Supplement), Abstract #9610, 1 page (2005).
Sicklick et al., "Hedgehog signaling maintains resident hepatic progenitors throughout life", Am. J. Physiol. Gastrointest. Liver Physiol., vol. 290, No. 5, pp. G859-G870 (2006).
Sicklick et al., "Dysregulatlon of the hedgehog pathway in human hepatocarcinogenesis", Carcinogenesis, vol. 27, No. 4, pp. 748-757 (2006).
Simmons and Smith, "A new synthesis of cyclopropanes from olefins", J. Am. Chem. Soc., vol. 80, No. 19, pp. 5323-5324 (1958).
Sims-Mourtada et al., "Hedgehog: an attribute to tumor regrowth after chemoradiotherapy and a target to improve radiation response", Clin. Cancer Res., vol. 12, No. 21, pp. 6565-6572 (2006).
Singh et al., "Hedgehog-producing cancer cells respond to and require autocrine hedgehog activity", Cancer Res.; vol. 71, No. 13, pp. 4454-4463 (2011).
Siu et al., "A first-in-human, phase I study of an oral hedgehog (HH) pathway antagonist, BMS-833923 (XL 139), in subjects with advanced or metastatic solid tumors", J. Clin Oncol., vol. 28, pp. 15s, Suppl. Abstract #2501, 3 pgs. (2010) Abstract Only.
Skipper et al., "In vivo efficacy of marimastat and chemoradiation in head and neck cancer xenografts", ORL, vol. 71, No. 1, pp. 1-5, Original Paper, DOI:10.1159/000163217 (2009).
Skvara et al., "Topical treatment of basal cell carcinomas in nevoid basal cell carcinoma syndrome with a smoothened inhibitor", J. Invest. Dermatol., vol. 131, No. 8, pp. 1735-1744 Original Article, DOI:10.1038/jid.2011.48 (2011).
Smith and Thomas, "Animal models for the study of squamous cell carcinoma of the upper aerodigestive tract: a historical perspective with review of their utility and limitations, Part A. Chemically-induced de novo cancer, syngeneic animal models of HNSCC, animal models of transplanted xenogeneic human tumors," Int. J. Cancer, vol. 118, No. 9, pp. 2111-2122 (2006).
Stanton et al., "Small-molecule modulators of the sonic hedgehog signaling pathway", Mol. Biosyst., vol. 6, pp. 44-54 (2010).
Stecca et al., "Melanomas require HEDGEHOG-GLI signaling regulated by interactions between GLI1 and the RAS-MEK/AKT pathways", PNAS, vol. 104, No. 14, pp. 5895-5900 (2007).
Steg et al., "Multiple gene expression analyses in paraffin-embedded tissues by TaqMan low-density array, application to hedgehog and Wnt pathway analysis in ovarian endometroid adenocarcinoma", J. Mol. Diagn., vol. 8, No. 1, pp. 76-83 (2006).
Suggs et al., "Facile homogeneous hydrogenations of hindered olefins with [Ir(cod)py(PCy$_3$)]PF$_6$", Tetrahedron Letters, vol. 22, Issue 4, pp. 303-306 (1981).
Suginome et al., "Synthesis of O,N-diacetyl-3β-hydroxy-5α,12α-jervan-11-one with 17-epi-configuration by hypoiodite reaction (1,2)", Tetrahedron Letters, vol. 14, No. 42, pp. 4147-4150 (1973).
Suginome et al., "Photo-induced Radical Rearrangements of Hypoiodite of N-Acetyljervine and the Related C-nor-D-Homosteroid in the Presence of Mercury (II) Oxide and Iodine", Bull. Chem. Soc. Japan, vol. 54, No. 10, pp. 3042-3047 (1981).
Suginome et al., "The transformation of Jervine into 18-Functional D-Homo-C-Norsteroids. IV. The Transformation of Jervine into (20R)-18,20-β-epoxy-3β-hydroxy-17β-ethyletiojervan-18-one 3-acetate via (20R)-18,20β-epoxy-3β-hydroxy-12α,17β-ethyletiojervan-11-one 3-acetate", Bull. Chem. Soc. Jpn., vol. 54, No. 3, pp. 852-861 (1981).
Sydor et al., "Activity of IPI-926, a novel inhibitor of the HH pathway, in subcutaneous and orthotopically implanted xenograft tumors that express SHH ligand", Eur. J. Cancer, Supplement, vol. 6, No. 12, p. 179, Poster 570 (2008).
Taipale et al., "Effects of oncogenic mutations in smoothened and patched can be reversed by cyclopamine", Nature, vol. 406, No. 6799, pp. 1005-1009 (2000).
Tang et al., "Antitumor activity of extracts and compounds from the rhizomes of Veratrum dahuricum", Phytother. Res., vol. 22, No. 8, pp. 1093-1096 (2008).
Tannock et al., "Docetaxel plus prednisone or mitoxantrone plus prednisone for advanced prostate cancer", N. Engl. J. Med., vol. 351, No. 15, pp. 1502-1512 (2004).
Tas and Avci, "Rapid clearance of psoriatic skin lesions induced by topical cyclopamine", Dermatology, vol. 209 pp. 126-131 (2004).
Taylor et al., "Novel biosynthetic approaches to the production of unnatural amino acids using transaminases", Trends Biotechnol., vol. 16, No. 10, pp. 412-418 (1998).
Thayer et al., "Hedgehog is an early and late mediator of pancreatic cancer tumorigenesis", Nature, vol. 425, pp. 851-856 (2003).
Thievessen et al., J. "Hedgehog signaling in normal urothelial cells and urothelial carcinoma cell lines", J. Cell Physiol., vol. 203, No. 2, pp. 372-377 (2005) Abstract Only.
Travaglione et al., "Activity of IPI-926, a novel inhibitor of the Hh pathway, in subcutaneous and orthotopically implanted xenograft tumors that express SHh ligand", Infinity Pharmaceuticals, Inc., Presentation Poster, 1 page (2008).

(56) References Cited

OTHER PUBLICATIONS

Travaglione et al., "A novel HH pathway inhibitor, IPI-926, delays recurrence post-chemotherapy in a primary human SCLC xenograft model", AACR Meeting Abstracts Online, 99th AACR Annual Meeting, Apr. 12-16, 2008, San Diego, CA, Abstract #4611, 2 pags (2008).
Travaglione et al., "Induction of tumor-derived hedgehog ligand by chemotherapy", Infinity Pharmaceuticals, Inc., Presentation Poster, Abstract #323, 1 page (2009).
Travaglione et al., "The Hh inhibitor IPI-926 enhances tumor perfusion and nab-paclitaxel activity in a pancreatic xenograft model", Infinity Pharmaceuticals, Inc., Presentation Poster, Abstract #LB-374, 1 page (2010).
Tremblay et al., "Synthesis of novel, chemically stable D-homo-cyclopamine analogs via a cyclopropanation/ring-expansion sequence", Infinity Pharmaceuticals, Inc., 1 page (2007).
Tremblay et al., "Semisynthetic cyclopamine analogues as potent and orally bioavailable hedgehog pathway antagonists", J. Med. Chem., vol. 51, No. 21, pp. 6646-6649 (2008).
Tremblay et al., "Synthesis and structure activity relationship of D-homo cyclopamine analogs: 3-substituted analogs", Infinity Pharmaceuticals, Inc., Presentation Poster, 1 page (2009).
Tremblay et al., "Discovery of IPI-926, a semi-synthetic clinical candidate that targets the hedgehog pathway", Infinity Pharmaceuticals, ACS Meeting Salt Lake City, UT on Mar. 25, 2009, Presentation Slides, 26 pages (2009).
Tremblay et al., "Discovery of a potent and orally active hedgehog pathway antagonist (IPI-926)", J. Med. Chem., vol. 52, No. 14, pp. 4400-4418 (2009).
Tremblay et al., "Recent patents for hedgehog pathway inhibitors for the treatment of malignancy", Expert Opin. Ther. Pat., vol. 19, No. 8, pp. 1039-1056 (2009).
Tremblay et al., "New Developments in the discovery of small molecule Hedgehog pathway antagonists", Curr. Opin. Chem. Biol., vol. 14, No. 3, pp. 428-435 (2010) Article in press, COCHBI-737, vol. 14, pp. 1-8 (2010).
Tremblay et al., "Development of multi-kilogram synthetic route to IPI-926, a novel hedgehog pathway antagonistic for the treatment of malignant diseases", Infinity Pharmaceuticals, Inc., Apr. 2, 2011, Presentation Slides, 29 pages (2011).
Tschesche et al., "Concerning the biosynthesis of steroid derivatives in the plant kingdom, 3rd mess.[1]: Spirostanol-biogenesis from cholesterol-glucoside", Z. Naturforsch, vol. 21b pp. 494-495 (1966) German language with English translation.
Tsuji et al., "Highly stereoselective hydrogenation of 3-oxo4-ene and -1,4-diene steroids to 5β compounds with palladium catalyst", J. Org. Chem., vol. 45, pp. 2729-2731 (1980).
Turner et al., "Sonic hedgehog pathway inhibition alters epididymal function as assessed by the development of sperm motility", Journal of Andrology, vol. 27, No. 2, pp. 225-232 (2006).
Van Der Horst et al., "Hedgehog stimulates only osteoblastic differentiation of undifferentiated KS483 cells", Bone, vol. 33, No. 6, pp. 899-910 (2003).
Vanhook, "Focus issue: fine-tuning hedgehog signaling in development and disease", Sci. Signaling, vol. 4, Issue 200, No. eg10, pp. 1-2 (2011).
Van Weerden et al., "Human xenograft models as useful tools to assess the potential of novel therapeutics in prostate cancer", Br. J. Cancer, vol. 100, No. 1, pp. 13-18 (2009).
Veratrum nigrum, Wikipedia entry last updated Apr. 23, 2014, Retreived from the internet http://en.wikipedia.org/wiki/Veratrum_nigram.
Villavicencio et al., "The sonic hedgehog-patched-gli pathway in human development and disease", Am. J. Hum. Genet., vol. 67, No. 5, pp. 1047-1054 (2000).
Villavicencio et al., "Activity of the Hh pathway inhibitor IPI-926 in a mouse model of medulloblastoma", Infinity Pharmaceuticals, Inc., Abstract #3199, Presentation Poster, 1 page (2009).
Voituriez and Charette, "Enantioselective cyclopropanation with TADDOL-derived phosphate ligands", Adv. Synth. Catal., vol. 348, Issue 16-17, pp. 2363-2370 (2006).
Von Hoff et al., "Inhibition of the hedgehog pathway in advanced basal-cell carcinoma", N. Eng. J. Med., vol. 361, No. 12, pp. 1164-1172 (2009).
Wang et al., "Revision of structure of peimisine", Yao Xue Xue Bao, vol. 27, No. 4, pp. 273-278 (1992) Database Accession No. 1992:490583, (1992).
Wanshura et al., "Sequential activation of snail1 and N-Myc modulates sonic hedgehog-induced transformation of neural cells", Cancer Res.; vol. 71, No. 15, pp. 5336-5345 (2011).
Warzecha et al., "Inhibition of osteosarcoma cell proliferation by the hedgehog-inhibitor cyclopamine", J. Chemother., vol. 19, No. 5, pp. 554-561 (2007).
Watkins et al., Hedgehog signaling within airway epithelial progenitors and in small-cell lung cancer, Nature, vol. 422, pp. 313-317 (2003).
Wei et al., "Indian hedgehog and its targets in human endometrium: menstrual cycle expression and response to CDB-2914", J. Clin. Endocrinol. Metab., vol. 95, No. 12, pp. 5330-5337 (2010).
Williams et al., "Identification of a small molecule inhibitor of the hedgehog signaling pathway: effects on basal cell carcinoma-like lesions", PNAS USA, vol. 100, No. 8, pp. 4616-4621 (2003).
Wintersteiner et al., "Structure of jervine, V. the sulfuric acid-catalyzed acetolysis of diacetyltetrahydrojervine", J. Am. Chem. Soc., vol. 76, No. 22, pp. 5609-5616 (1954) Database Accession No. 1955:73588 (1954).
Wong et al., "Primary cilia can both mediate and suppress Hedgehog pathway-dependent tumorigenesis", Nat. Med., vol. 15, No. 9, pp. 1055-1061 (2009).
Wu et al., "Chemical constituent of hubeibeimu, V. Isolation and identification of hupehenisine", Yaoxue Xuebao, vol. 21, No. 7, pp. 546-550 (1986) Database Accession No. 1987:15699 (1987).
Wunder et al., "Opportunities for improving the therapeutic ratio for patients with sarcoma", Lancet Oncol., vol. 8, No. 6, pp. 513-524 (2007).
Xie et al., "Activating smoothened mutations in sporadic basal-cell carcinoma", Nature, vol. 391, pp. 90-92 (1998).
Yamakawa et al., "CH/Π attraction: the origin of enantioselectivity in transfer hydrogenation of aromatic carbonyl compounds catalyzed by chiral $\eta^6$-arene-ruthenium(II) complexes", Angew. Chem. Int. Ed., vol. 40, No. 15, pp. 2818-2821 (2001).
Yamaura et al., "Repeated application of glucocorticoids exacerbate pruritus via inhibition of prostaglandin D2 production of mast cells in a murine model of allergic contact dermatitis", J. Toxicol. Sci., vol. 37, No. 6, pp. 1127-1134 (2012).
Yang and Hinds, "pRb-mediated control of epithelial cell proliferation and Indian Hedgehog expression in mouse intestinal development", BMC Developmental Biology, vol. 7, No. 6, pp. 1-12 (2007).
Yauch et al., "Smoothened mutation confers resistance to a hedgehog pathway inhibitor in medulloblastoma", Science, vol. 326, No. 5952, pp. 572-574 (2009).
Yoo et al., "Sonic hedgehog signaling promotes motility and invasiveness of gastric cancer cells through TGF-β-mediated activation of the ALK5-smad 3 pathway", Carcinogenesis, vol. 29, No. 3, pp. 480-490 (2008).
Yoshizaki et al., "Expressions of sonic hedgehog, patched, smoothened and Gli-1 in human intestinal stromal tumors and their correlation with prognosis", World J. Gastroenterol., vol. 12, No. 35, pp. 5687-5691 (2006).
Yu et al., "Chemical constituents of the unibract fritillary (Fritillaria unibracteata)", Zhongcaoyao, vol. 21, No. 1, pp. 2-6 (1990), Database Accession No. 1990:512481 (1990).
Yun et al., "Simultaneous synthesis of enantiomerically pure (R)-1-phenylethanol and (R)-α-methylbenzylamine from racemic α-methylbenzylamine using ω-transaminase/alcohol dehydrogenase/glucose dehydrogenase coupling reaction", Biotechnol. Lett., vol. 25, No. 10, pp. 809-814 (2003).
Yun et al., "β-Amino acid: Pyruvate transaminase from Alcaligenes denitrificans Y2k-2: A new catalyst for kinetic resolution of β-amino acids and amines", Appl. Environ. Microbiol., vol. 70, No. 4, pp. 2529-2534 (2004).

(56) References Cited

OTHER PUBLICATIONS

Zanotti-Gerosa et al., "Ruthenium-catalysed asymmetric reduction of ketones, diphosphine ligands in hydrogenations for pharmaceutical synthesis", Platinum Metals Rev., vol. 49, No. 4, pp. 158-165 (2005).

Zassoinovich et al., "Asymmetric hydrogen transfer reactions promoted by homogeneous transition metal catalysts", Chem. Rev., vol. 92, No. 5, pp. 1051-1069 (1992).

Zeisberg and Neilson, "Biomarkers for epithelial-mesenchymal transitions", J. Clin. Invest., vol. 119, No. 6, pp. 1429-1437 (2009).

Zeng et al., "Neurosteroid analogues. 10. The effect of methyl group substitution at the C-6 and C-7 positions on the GABA modulatory and anesthetic actions of $(3\alpha,5\alpha)$- and $(3\alpha, 5\beta)$-3-hydroxypregnan-20-one", J. Med. Chem., vol. 48, No. 8, pp. 3051-3059 (2005).

Zhang et al., "Hedgehog pathway responsiveness correlates with the presence of primary cilia on prostate stromal cells", BMC Developmental Biology, vol. 9, No. 50, pp. 1-7 (2009).

Zhao et al., "Studies on the constituents of veratrum plants II. Constituents of *Veratrum nigrum* L. var. ussuriense (1). Structure and $^1H$- and $^{13}C$-nuclear magnetic resonance spectra of a new alkaloid, verussurinine, and related alkaloids", Chem. Pharm. Bull., vol. 39, No. 3, 549-554 (1991).

Zhao et al., "Hedgehog signalling is essential for maintenance of cancer stem cells in myeloid leukaemia", Nature, vol. 460, No. 7255, pp. 652-656 (2009) Pre-Publication Article DOI: 10.1038/nature07737, pp. 1-5 (2009).

TOPICAL FORMULATIONS FOR DELIVERY OF HEDGEHOG INHIBITOR COMPOUNDS AND USE THEREOF

CROSS-REFERENCE TO RELATED APPLICATIONS

This application is a Continuation of U.S. Non-Provisional patent application Ser. No. 16/239,457, filed Jan. 3, 2019, which is a Divisional of U.S. Non-Provisional patent application Ser. No. 15/173,257, filed Jun. 3, 2016, now U.S. Pat. No. 10,369,147, Issue Date Aug. 6, 2019, which claims the benefit of U.S. Provisional Application No. 62/171,117, filed Jun. 4, 2015, and of U.S. Provisional Application No. 62/275,185, filed Jan. 5, 2016. All aforementioned applications are incorporated herein by reference in their entireties.

TECHNICAL FIELD

The subject matter described herein relates to compositions for topical application of a hedgehog inhibitor compound and to topical delivery systems for administration of a hedgehog inhibitor compound.

BACKGROUND

Drug administration by topical skin application of a drug offers distinct advantages over conventional administration methods. For example, some drugs cannot be absorbed in the digestive tract and intravenous and subcutaneous administration by injection is inconvenient and invasive. Oral and intravenous administration for treatment of a localized skin condition is undesirable as the drug is circulated systemically rather than restricted to the localized, diseased area. Yet, due to the protective nature of skin serving its intended function of being resistant to external perturbations, only a limited number of drugs are bioavailable via topical application.

Drug administration via the skin may be transdermal or intradermal (also referred to as local or dermal). Transdermal administration involves transport through the skin such that a therapeutic amount of the drug is achieved in the systemic blood circulation. Intradermal or topical administration of a drug involves entry of the drug across the stratum corneum for a cutaneous or local skin effect; that is the pharmacological effect of the drug is localized to the intracutaneous regions of drug penetration and deposition. Preferably, intradermal absorption occurs with little or no systemic absorption or accumulation. Intradermal absorption of a drug involves partitioning of the drug from the applied vehicle into the *stratum corneum*; diffusion of the drug through the *stratum corneum*; and partitioning of the drug from the stratum corneum into the epidermis. In contrast, transdermal absorption further involves diffusion of the drug through the epidermis; and capillary uptake of the drug for circulation in the blood.

Whereas transdermal compositions are intended to deliver drugs for systemic circulation, a different composition would be needed to deliver the same drug intracutaneously. Topical formulations that achieve delivery of a drug across the stratum corneum and retention of the majority of the drug dermally such that it does not enter the blood stream in significant amounts are complicated to design and require innovative approaches. Several factors determine the permeability of the skin or of specific layers, in particular the *stratum corneum*, of the skin to drug compounds. These factors include the characteristics of the skin, the characteristics of the drug compound (e.g., its size (molecular weight or molecular volume), its lipophilicity/hydrophilicity, its polarity), the dosage of the drug compound applied, interactions between the drug compound and the delivery vehicle, interactions between the drug compound and the skin, and interactions of the drug and the skin in the presence of the ingredients in the delivery vehicle. As a result of the multitude of factors involved in administration of a drug intracutaneously, it is generally accepted that whether intracutaneous delivery of a drug compound can be achieved in an amount sufficient for therapy is uncertain. Penetration enhancers are commonly used in transdermal delivery to achieve penetration of a drug across the *stratum corneum* typically to provide for systemic delivery of the drug, rather than its retention in the epidermis or dermis. Thus, topical administration, while desired from a patient convenience and drug delivery view, has been largely unsuccessful for many compounds as evidenced by the relatively few drugs approved for topical administration.

A condition that would benefit from a topical formulation that achieves intracutaneous delivery of a drug is basal cell carcinoma (BCC), the most common form of skin cancer in the United States. BCC is observed in the general population typically on sun-exposed areas of the skin, and in subjects with the Basal Cell Nevus Syndrome, also known as Gorlin syndrome, an inherited condition where the skin is prone to developing BCCs. Although BCCs rarely spread (i.e., metastasize) to other parts of the body, they can be destructive and disfiguring. A variety of surgical and non-surgical therapies are available for BCCs. Nonsurgical therapies include radiation therapy, chemotherapy, and immunotherapy. These therapies can be useful for definitive treatment of primary tumors and some recurrent BCC tumors and for relieving symptoms associated with inoperable tumors. However, some of these therapies also can have significant unpleasant side effects. Side effects of radiation therapy and certain chemotherapies are well documented. One form of immunotherapy involves intralesional injections of interferon. While interferon therapy can be effective against BCC, the multiple intralesional injections can require several clinic visits per week for many weeks and are painful. Thus, there remains a need for a non-surgical therapy for BCC that offers better patient convenience.

The foregoing examples of the related art and limitations related therewith are intended to be illustrative and not exclusive. Other limitations of the related art will become apparent to those of skill in the art upon a reading of the specification and a study of the drawings.

BRIEF SUMMARY

The following aspects and embodiments thereof described and illustrated below are meant to be exemplary and illustrative, not limiting in scope.

In one (or a first) aspect, a composition comprising a hedgehog inhibitor compound and a solvent system comprising (i) a monohydric primary alcohol and a polyol in a w/w ratio of between about 0.9-1.8 and (ii) a buffer or a fatty acid comprising between 13-22 carbon atoms, wherein the hedgehog inhibitor compound is present in the solvent system between about 0.1-10 wt % is provided.

In another (or second) aspect, a composition is provided that is comprised of a hedgehog inhibitor compound and a solvent system, the hedgehog inhibitor having a saturation solubility in the solvent system of between about 0.1-10 wt %, preferably between about 2.5-8 wt %, and the solvent system comprising between about 15-60 wt % of a monohydric primary alcohol and between about 10-50 wt % propylene glycol.

Instill another (or third) aspect, a composition is provided that is comprised of a hedgehog inhibitor compound and a solvent system comprising (i) a monohydric alcohol comprised of at least one of ethanol and benzyl alcohol and propylene glycol, the monohydric alcohol and propylene glycol in a w/w ratio of between about 0.9-1.8 and (ii) a buffer or a fatty acid comprising between 13-22 carbon atoms, wherein the hedgehog inhibitor compound is present in the solvent system between about 0.1-10 wt %.

In one embodiment, the monohydric alcohol is of the form R—OH, where R is selected from methyl, ethyl, propyl, butyl, and pentyl. In another embodiment, the monohydric alcohol is represented by the structure $C_nH_{2n}$—OH, where n is 1, 2, 3 or 4.

In yet another embodiment, the monohydric alcohol additionally includes benzyl alcohol. In still another embodiment, the monohydric primary alcohol is a combination of ethanol and benzyl alcohol. In another embodiment, the primary monohydric alcohol comprises phenoxyethanol.

In another embodiment, the solvent system further comprises diethylene glycol monoethyl ether.

In another embodiment, the fatty acid is a saturated fatty acid. In one embodiment, the saturated fatty acid is selected from myristic acid (C14), palmitic acid (C16), stearic acid (C18) and arachidic acid (C22). In yet another embodiment, the saturated fatty acid is iso-stearic acid.

In one embodiment, the hedgehog inhibitor compound is present in the solvent system in an amount between about 2-8 wt %.

In one embodiment, the solvent system comprises between about 1-3 wt % benzyl alcohol. In still another embodiment, the solvent system further comprises diethylene glycol monoethyl ether. In yet another embodiment, the solvent system comprises diethylene glycol monoethyl ether and does not comprise benzyl alcohol.

In still another embodiment, the monohydric alcohol is ethanol and the ratio (w/w) of ethanol to diethylene glycol monoethyl ether is within about 10-20% of the ratio (w/w) of ethanol to propylene glycol.

In another embodiment, the monohydric alcohol is ethanol and the ratio (w/w) of ethanol to diethylene glycol monoethyl ether is the same as the ratio (w/w) of ethanol to propylene glycol.

In one embodiment, the solvent system comprises a buffer at pH 7.5.

In yet another embodiment, the composition further comprises a gelling agent. An exemplary gelling agent is, in one embodiment, hydroxypropylcellulose.

In one embodiment, the hedgehog inhibitor is patidegib or is a combination of patidegib and itraconazole. In another embodiment, the hedgehog inhibitor is itraconazole.

In another (or fourth) aspect, a composition is provided that is comprised of patidegib and a solvent system comprising (i) ethanol and propylene glycol in a w/w ratio of between about 0.9-1.8, (ii) diethylene glycol monoethyl ether, and (iii) a buffer, wherein the hedgehog inhibitor compound is present in the solvent system in an amount between about 0.1-10 wt %.

In one embodiment, the ratio (w/w) of ethanol to diethylene glycol monoethyl ether is within about 10-20% of the ratio (w/w) of ethanol to propylene glycol. In another embodiment, the ratio (w/w) of ethanol to diethylene glycol monoethyl ether is the same as the ratio (w/w) of ethanol to propylene glycol.

In another (or fifth) aspect, a composition is provided that is comprised of patidegib and a solvent system comprising (i) ethanol, benzyl alcohol and propylene glycol, the ethanol and benzyl alcohol in a w/w ratio with propylene glycol of between about 0.9-1.8 and (ii) a fatty acid comprising between 13-22 carbon atoms, wherein the hedgehog inhibitor compound is present in the solvent system in an amount between about 0.1-10 wt %.

In one embodiment, the fatty acid is a saturated fatty acid. In another embodiment, the saturated fatty acid is selected from myristic acid (C14), palmitic acid (C16), stearic acid (C18) and arachidic acid (C22). In still another embodiment, the saturated fatty acid is iso-stearic acid.

In one embodiment, the solvent system comprises between about 1-3 wt % benzyl alcohol.

In another (or sixth) aspect, a composition is provided that consists essentially of patidegib and a solvent system comprising ethanol and propylene glycol in a w/w ratio of between about 0.9-1.8, wherein the patidegib has a saturation solubility in the solvent system of between about 2.5-8 wt % and wherein formulation provides an in vitro concentration of patidegib in the dermis of greater than about 250 µM 48 hours after topical application.

In one embodiment, the solvent system further comprises diethylene glycol monoethyl ether and a buffer.

In another embodiment, the solvent system further comprises a fatty acid comprising between 13-22 carbon atoms.

In still another embodiment, the solvent system further comprises benzyl alcohol.

In another (or seventh) aspect, a composition is provided that consists essentially of patidegib and a solvent system consisting of ethanol and propylene glycol in a w/w ratio of between about 0.9-1.8, diethylene glycol monoethyl ether and a buffer.

In still another (or eighth) aspect, a composition is provided that consists essentially of patidegib and a solvent system consisting of ethanol and benzyl alcohol in a w/w ratio with propylene glycol of between about 0.9-1.8 and a saturated fatty acid comprising between 13-22 carbon atoms.

In yet another (or ninth) aspect, provide is a composition comprising a hedgehog inhibitor compound and a solvent system comprising (i) a monohydric primary alcohol and an optionally lower alkyl end-capped oligomeric alkylene glycol in a w/w ratio of between about 0.8 and 2.6 and (ii) a fused bicyclic ether having from 8-14 carbon atoms, wherein the hedgehog inhibitor compound is present in the solvent system between about 0.1-10 wt %.

In one or more embodiments related to the ninth aspect, the w/w ratio of the monohydric primary alcohol and the optionally lower alkyl end-capped oligomeric alkylene glycol is between about 1.0 and 2.4, or is between about 1.0 and 2.3. Exemplary monohydric alcohols have been previously described. For example, in one or more embodiments, the monohydric alcohol is of the form R—OH, where R is selected from methyl, ethyl, propyl, butyl, and pentyl. In one or more additional embodiments, the monohydric alcohol is represented by the structure $C_nH_{2n}$—OH, where n is 1, 2, 3 or 4. In a preferred embodiment of the foregoing, R is ethyl.

In one or more additional embodiments related to the ninth aspect, or its related embodiments, the monohydric primary alcohol comprises benzyl alcohol. In one or more exemplary related embodiments, the monohydric primary alcohol comprises a mixture of a C1-C6 primary aliphatic alcohol and benzyl alcohol. In one or more particular embodiments, the composition comprises ethyl alcohol and benzyl alcohol. In one or more related embodiments, the composition comprises from about 1% to about 8% by weight benzyl alcohol, or alternatively, comprises from about 2% to about 6% by weight benzyl alcohol. In yet one or more additional embodiments related to the ninth aspect, the w/w ratio of the monohydric alcohol to benzyl alcohol is in a range of about 3 to 11, or more preferably, is in a range of about 4 to 10.

In one or more additional embodiments related to the ninth aspect, the percent by weight of benzyl alcohol is less than the percent by weight of the optionally lower alkyl end-capped oligomeric alkylene glycol and is also less than the percent by weight of the fused bicylic ether having from 8-14 carbon atoms.

In one or more particular embodiments, the optionally lower alkyl end-capped oligomeric alkylene glycol is end-capped. Illustrative end capping groups include a methyl (—OCH$_3$) or an ethyl (—OCH$_2$CH$_3$) group.

In one or more embodiments, the optionally lower alkyl end-capped oligomeric alkylene glycol comprises from 2 to 4 ethylene oxide repeat units. In one or more particular embodiments, the optionally lower alkyl end-capped oligomeric alkylene glycol comprises 2 ethylene oxide repeat units. In yet a further embodiment, the optionally lower alkyl end-capped oligomeric alkylene glycol is end-capped and is diethylene glycol monoethyl ether (DEGMEE).

In one or more further embodiments, e.g., related to the ninth aspect, the optionally lower alkyl end-capped oligomeric alkylene glycol is a non-end capped oligomeric ethylene glycol having a number average molecular weight from 300-600 (i.e., a PEG having an average molecular weight between about 300 and 600. In one or more particular embodiments, the non-end capped oligomeric ethylene glycol has a number average molecular weight of 400.

In one or more particular embodiments, the optionally lower alkyl end-capped oligomeric alkylene glycol is either diethylene glycol monoethyl ether or is PEG (e.g., PEG 300-600). In yet a further embodiment, the composition comprises either diethylene glycol monoethyl ether or PEG (e.g., PEG 300-600) but does not comprise both.

In one or more further embodiments related to the ninth aspect (and its related embodiments), the w/w ratio of the optionally lower alkyl end-capped oligomeric alkylene glycol to the fused bicyclic ether having from 8-14 carbon atoms is in a range between about 1 and 2, or alternatively, is in a range between about 1.2 and 1.8.

In one or more specific embodiments, the w/w ratio of the optionally lower alkyl end-capped oligomeric alkylene glycol to the fused bicyclic ether having from 8-14 carbon atoms is about 1.7.

In one or more further embodiments related to the ninth aspect, the combined percent by weight of the optionally lower alkyl end-capped oligomeric alkylene glycol and the fused bicyclic ether having from 8-14 carbon atoms is from 30-50 w/w %.

In yet an additional one or more embodiments, the combined percent by weight of the optionally lower alkyl end-capped oligomeric alkylene glycol and the fused bicyclic ether having from 8-14 carbon atoms is 40 w/w %.

In one or more particular embodiments, the fused bicyclic ether having from 8-14 carbon atoms comprises two fused tetrahydrofuran rings. In yet one or more additional embodiments, the two fused tetrahydrofuran rings possess two methoxy substituents. In a preferred embodiment, the fused bicyclic ether is dimethyl isosorbide.

In yet another embodiment related to the ninth aspect or its related embodiments, the composition is absent benzyl alcohol. In yet an additional one or more further related embodiments, the composition is absent benzyl alcohol and further comprises phenoxyethanol, e.g., from 0.5 to 2.5 weight percent phenoxyethanol. In yet a further embodiment related to the foregoing, the composition is absent both benzyl alcohol and propylene carbonate, yet comprises phenoxyethanol.

In one or more additional embodiments related to at least the ninth aspect, the composition further comprising from 1 to 7 weight percent propylene carbonate.

In one or more preferred embodiments, the composition comprises an N-methyl lactam.

In one or more particular embodiments, the composition comprises N-methyl pyrrolidone. In one or more embodiments related to the foregoing, the composition comprises N-methyl pyrrolidone, and the w/w ratio of the monohydric primary alcohol and the optionally lower alkyl end-capped oligomeric alkylene glycol is between about 1.0 and 1.5. In yet one or more further embodiments, the percentage by weight of each of the monohydric primary alcohol, the optionally lower alkyl end-capped oligomeric alkylene glycol, and N-methyl pyrrolidone is from 20-30. In a preferred embodiment, the composition comprises ethanol, diethylene glycol monoethyl ether, and N-methyl pyrrolidone.

In yet an additional aspect (or tenth aspect), provided is a composition comprising a hedgehog inhibitor compound and a solvent system comprising (i) a ternary combination of low molecular weight aliphatic polyols (e.g., having molecular weights in a range from 50 to 550) having 2 or 3 hydroxyl groups and a lower alkyl end-capped oligomeric alkylene glycol in a w/w ratio of between about 1.5 and 2.4 and (ii) a fused bicyclic ether having from 8-14 carbon atoms, wherein the hedgehog inhibitor compound is present in the solvent system between about 0.1-10 wt %.

In one or more embodiments related to the tenth aspect, the ternary combination of low molecular weight aliphatic polyols comprises HOCH$_2$C(OH)HR' where R' is —CH$_3$ or —CH$_2$OH. In yet a more particular embodiment, the ternary combination of low molecular weight aliphatic polyols comprises glycerol and propylene glycol.

In one or more further embodiments, the ternary combination of low molecular weight aliphatic polyols comprises glycerol, propylene glycol and polyethylene glycol. In one or more further embodiments, the polyethylene glycol has a number average molecular weight from 300-500. In one or more particular embodiments, the w/w ratio of propylene glycol to glycerol is between 1.5 and 2.5 and the w/w ratio of polyethylene glycol to glycerol is between 1.5 and 2.5.

In one or more further embodiments related to the tenth aspect, the w/w ratio of the ternary combination of aliphatic polyols to the lower alkyl end-capped oligomeric alkylene glycol is in a range from 1.8 to 2.1. In yet one or more further embodiments, the composition comprises from about 40 to 55 percent by weight of the ternary combination of aliphatic polyols.

In yet another embodiment related to the tenth aspect, the composition is absent an aliphatic monohydric alcohol (e.g., ethanol).

In one or more additional embodiments related to the tenth aspect, the composition further comprises from about 1% to about 8%, or from about 2% to about 6% by weight benzyl alcohol.

In one or more additional embodiments related to the tenth aspect, the weight percent of benzyl alcohol is less than the weight percent of the lower alkyl end-capped oligomeric alkylene glycol and is also less than the weight percent of the fused bicylic ether having from 8-14 carbon atoms.

In one or more further embodiments, the lower alkyl end-capped oligomeric alkylene glycol is end-capped with a methyl or an ethyl group. In one or more particular embodiments, the lower alkyl end-capped oligomeric alkylene glycol comprises 2 ethylene oxide repeat units. In a preferred embodiment, the lower alkyl end-capped oligomeric alkylene glycol is diethylene glycol monoethyl ether (DEGMEE).

In one or more further embodiments directed to at least the tenth aspect, the w/w ratio of the lower alkyl end-capped oligomeric alkylene glycol to the fused bicyclic ether having from 8-14 carbon atoms is in a range between about 1 and 2, or is more preferably in a range between about 1.2 and 1.8.

In one or more additional embodiments related to at least the tenth aspect, the w/w ratio of the lower alkyl end-capped oligomeric alkylene glycol to the fused bicyclic ether having from 8-14 carbon atoms is about 1.7.

In one or more further embodiments related to the tenth aspect, the combined percent by weight of the lower alkyl end-capped oligomeric alkylene glycol and the fused bicyclic ether having from 8-14 carbon atoms is from 30-50 w/w %. In a particular embodiment, the combined percent by weight of the lower alkyl end-capped oligomeric alkylene glycol and the fused bicyclic ether having from 8-14 carbon atoms is 40 w/w %.

In one or more particular embodiments related to the tenth (or ninth) aspect, the fused bicyclic ether having from 8-14 carbon atoms is dimethyl isosorbide.

In one or more embodiments related to the ninth or tenth aspects, the composition is absent a surfactant.

In one or more embodiments related to the ninth or tenth aspects, the composition is non-aqueous.

In one or more embodiments related to the ninth or tenth aspects, the composition is absent a triglyceride.

In one or more embodiments related to the ninth or tenth aspects, the composition is absent a complexing agent such as a cyclodextrin.

In one or more embodiments related to the ninth or tenth aspects, the composition is not an oil-in-water emulsion.

In one or more embodiments related to the ninth or tenth aspects, the composition is absent a hydrophobic oil.

In one or more additional embodiments related to the ninth or tenth aspects, the composition is absent a surfactant, is absent a triglyceride, is absent a complexing agent, is absent a hydrophobic oil, and is not an oil-in-water emulsion.

In yet a further embodiment related to the ninth or tenth aspects, the composition further comprising a gelling agent. In one or more embodiments, the gelling agent is hydroxypropylcellulose. In one or more related embodiments, the composition is in the form of a gel.

In one or more further embodiments related to at least the ninth and tenth aspects, the hedgehog inhibitor compound is a triazolyl-triazolone. In one or more particular embodiments, the hedgehog inhibitor compound is itraconazole or is a combination of itraconazole and patidegib.

In one or more additional embodiments related to the foregoing, the composition possesses a saturated solubility of itraconazole of from about 0.14-1.5 w/w percent, or more preferably, from about 0.25-1.0 w/w percent.

In one or more further embodiments, the itraconazole is present in the solvent system between about 0.1-5 wt %, or more preferably, is present in the solvent system between about 0.1-2 wt %.

In yet another aspect, topical delivery system is provided that is comprised of a composition as described herein. The topical delivery system can further comprise, in one embodiment, a backing member and membrane joined to define a reservoir in which the composition is contained. In one embodiment, the membrane is a non-rate controlling membrane.

In another aspect, the present invention provides a method of treating a skin cancer in a subject, the method comprising the topical administration to the skin of a subject a therapeutically effective amount of a composition comprising, consisting essentially of, or consisting of a composition or topical delivery system as described herein.

In still another aspect, a method for treating basal cell carcinoma is provided, where the method comprises providing a composition as described herein or a topical delivery system as described herein, whereby the providing comprises instructions to topically apply the composition of the system and wherein said topically applying achieves intracutaneous delivery of the hedgehog inhibitor compound in an amount sufficient for treating basal cell carcinoma, with a non-therapeutic concentration of the compound present in the blood of the subject.

In still another aspect, a method for treating basal cell carcinoma is provided, where the method comprises topically applying a composition as described herein or a topical delivery system as described herein to a subject in need thereof, whereby the topically applying achieves intracutaneous delivery of the hedgehog inhibitor compound in an amount sufficient for treating basal cell carcinoma, with a non-therapeutic concentration of the compound present in the blood of the subject.

In still another aspect, a method for preventing basal cell carcinoma in a subject at risk thereof is provided, where the method comprises topically applying a composition as described herein or a topical delivery system as described herein to a subject in need thereof, whereby the topically applying achieves intracutaneous delivery of the hedgehog inhibitor compound in an amount sufficient for treating basal cell carcinoma, with a non-therapeutic concentration of the compound present in the blood of the subject.

In yet another aspect, a method for slowing progression (i.e., controlling the growth) of basal cell carcinoma in a subject with basal cell carcinoma or at risk of basal cell carcinoma is provided, where the method comprises topically applying a composition as described herein or a topical delivery system as described herein to a subject in need thereof, whereby the topically applying achieves intracutaneous delivery of the hedgehog inhibitor compound in an amount sufficient for controlling the growth of the basal cell carcinoma, with a non-therapeutic concentration of the compound present in the blood of the subject.

In one embodiment, the subject has Gorlin syndrome.

In addition to the exemplary aspects and embodiments described above, further aspects and embodiments will become apparent by reference to the drawings and by study of the following descriptions.

Additional embodiments of the present methods and compositions, and the like, will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present invention are set forth in the

DETAILED DESCRIPTION

I. Definitions

Figure 1A:
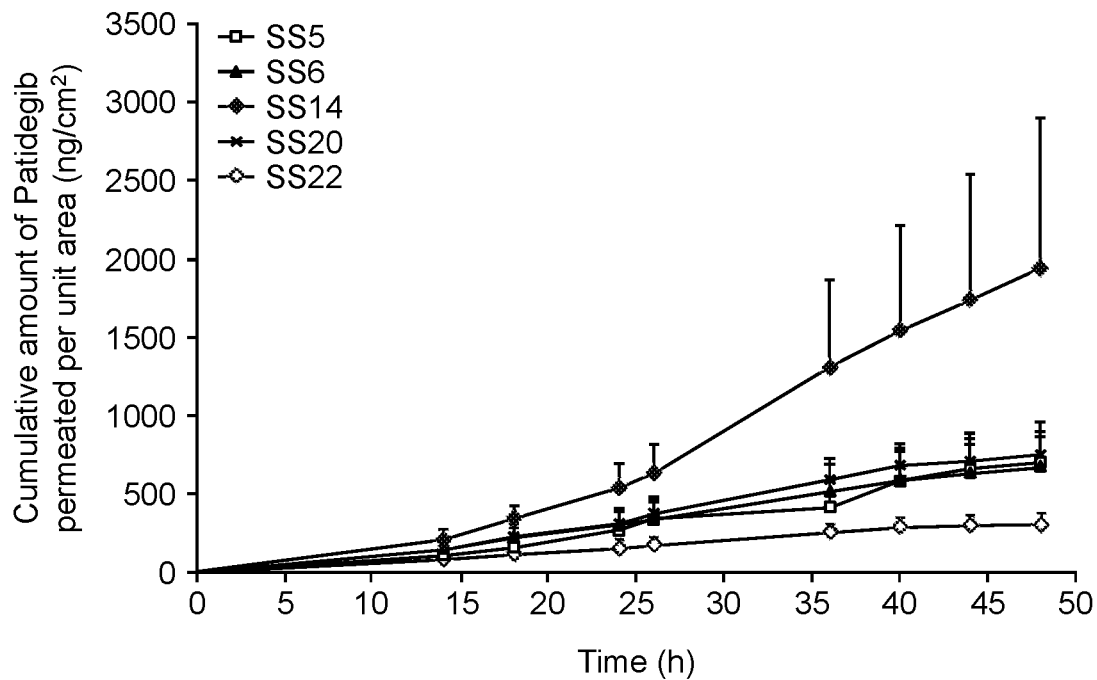
FIG. 1A is a graph showing the cumulative amount of patidegib permeated across human skin in vitro, in $ng/cm^2$, as a function of time, in hours, for five exemplary topical compositions of patidegib.

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

Where a range of values is provided, it is intended that each intervening value between the upper and lower limit of that range and any other stated or intervening value in that stated range is encompassed within the disclosure. For example, if a range of 1 μm to 8 μm is stated, it is intended that 2 μm, 3 μm, 4 μm, 5 μm, 6 μm, and 7 μm are also explicitly disclosed, as well as the range of values greater than or equal to 1 μm and the range of values less than or equal to 8 μm.

As used in this specification, the singular forms "a," "an," and "the" include plural referents unless the context clearly dictates otherwise. Thus, for example, reference to a "polymer" includes a single polymer as well as two or more of the same or different polymers, reference to an "excipient" includes a single excipient as well as two or more of the same or different excipients, and the like.

The compositions of the present disclosure can comprise, consist essentially of, or consist of, the components disclosed.

All percentages, parts and ratios are based upon the total weight of the topical compositions and all measurements made are at about 25° C., unless otherwise specified.

For any particular compound disclosed herein, any general or specific structure presented also encompasses all conformational isomers, regioisomers, and stereoisomers that can arise from a particular set of substituents, unless stated otherwise. Similarly, unless stated otherwise, the general or specific structure also encompasses all enantiomers, diastereomers, and other optical isomers whether in enantiomeric or racemic forms, as well as mixtures of stereoisomers, as would be recognized by a skilled artisan.

The phrase "pharmaceutically acceptable" is employed herein to refer to those compounds, salts, compositions, dosage forms, etc., which are—within the scope of sound medical judgment—suitable for use in contact with the tissues of human beings and/or other mammals without excessive toxicity, irritation, allergic response, or other problem or complication, commensurate with a reasonable benefit/risk ratio. In some aspects, "pharmaceutically acceptable" means approved by a regulatory agency of the federal or a state government, or listed in the U.S. Pharmacopeia or other generally recognized pharmacopeia for use in mammals (e.g., animals), and more particularly, in humans.

The term "treating" is used herein, for instance, in reference to methods of treating cancer, and includes the administration of a compound or composition or topical delivery system which reduces the frequency of, or delays the onset of, symptoms of a medical condition (e.g., cancer) in a subject relative to a subject not receiving the compound or composition or topical delivery system. This can include reversing, reducing, or arresting the symptoms, clinical signs, and underlying pathology of the condition in a manner to improve or stabilize a subject's condition (e.g., regression of tumor growth). Treatment of basal cell carcinoma encompasses, for example, chronic management of the condition, such as controlling the growth of the basal cell carcinoma, reducing the tumor burden, as well as prevention.

The terms "inhibiting" or "reducing" are used in reference to methods to inhibit or to reduce tumor growth (e.g., decrease the size of a tumor) in a population as compared to a untreated control population.

"Substantially" or "essentially" means nearly totally or completely, for instance, 95% or greater, of a given quantity.

"Oligomer" or "oligomeric" as used herein refers to a chemical entity having from 2 to 13 repeat units. For example, an oligomeric alkylene glycol is having from 2 to about 13 alkylene glycol repeat units, such as ethylene oxide or propylene oxide repeat units.

The term "end-capped" as used herein refers to a terminal or endpoint of an entity such as an oligomer having ethylene oxide repeat units in which one of the terminal hydroxyl groups has been converted to a non-reactive group, such as an ether (—OR). Typically, although not necessarily, the end-capping moiety is a lower alkoxy group, such as a $C_{1-6}$ alkoxy group. Examples of end-capping moieties include methoxy, ethoxy, propoxy, butoxy, and the like.

"Lower alkyl" refers to an alkyl group containing from 1 to 6 carbon atoms, and may be straight chain or branched, as exemplified by methyl, ethyl, n-butyl, i-butyl, t-butyl.

A "fused bicyclic ether" refers to a fused bicyclic ring system (i.e., containing two fused aliphatic rings) comprising from 1 to 3 oxygen atoms (e.g., 1, 2 or 3) in the ring system. The fused bicyclic ether possesses no unsaturation, and may comprise from 1 to 4 additional substituents comprising atoms selected from carbon, hydrogen and oxygen. One example of a fused bicyclic ether is isosorbide dimethyl ether (synonyms include dimethyl isosorbide and 1,4:3,6-dianhydro-2,5-di-O-methyl-D-glucitol), which possesses two methoxy groups substituted on the dianhydro-D-glucitol ring system. A fused bicyclic ether having from "8-14 carbon atoms" refers to the total number of carbon atoms contained in the fused bicyclic ether including any substituents.

"Alkoxy" refers to an —O—R group, wherein R is alkyl, preferably $C_1$-$C_6$ alkyl (e.g., methoxy, ethoxy, propoxy, etc.).

A "non-aqueous" formulation generally refers to a formulation comprises less than 2% by weight water. Thus, a non-aqueous formulation may comprise trace amounts of water, however water is not added as a formulation component.

A hydrophobic oil as used herein refers to a higher fatty acid ester, oils and fats, higher fatty acids, and higher acids, where higher refers to a carbon chain of 12-28 carbon atoms.

A low molecular weight polyol refers to a polyol having a molecular weight in a range from 50 to 550. For an oligomeric polyol such as oligomeric PEG, the molecular weight is generally a number average molecular weight.

"Optional" or "optionally" means that the subsequently described circumstance may but need not necessarily occur, so that the description includes instances where the circumstance occurs and instances where it does not.

By reserving the right to proviso out or exclude any individual members of any such group, including any sub-ranges or combinations of sub-ranges within the group, that can be claimed according to a range or in any similar manner, less than the full measure of this disclosure can be claimed for any reason. Further, by reserving the right to proviso out or exclude any individual substituents, analogs, compounds, ligands, structures, or groups thereof, or any members of a claimed group, less than the full measure of this disclosure can be claimed for any reason.

All publications cited herein are hereby incorporated by reference in their entirety.

II. Topical Formulations

A topical composition for intracutaneous delivery of a hedgehog inhibitor compound is described. Hedgehog inhibitor compounds and solvent systems that together comprise the topical formulations will now be described.

A. Hedgehog Inhibitor Compounds

The Hedgehog polypeptide is a secreted protein that functions as a signaling ligand in the hedgehog pathway. Three different forms of the hedgehog protein are found in humans: Sonic hedgehog, Desert hedgehog and Indian hedgehog. Sonic hedgehog is the most prevalent hedgehog member in mammals and also is the best characterized ligand of the hedgehog family. Prior to secretion, Sonic hedgehog undergoes an intramolecular cleavage and lipid modification reaction. The lipid modified peptide is responsible for signaling activities. Inhibition of the hedgehog pathway in certain cancers has been shown to result in inhibition of tumor growth (Von Hoff D. et al., *N. Engl. J. Med.*, 361(12):1164-72 (2009); Kim et al., *Cancer Cell*, 23(1):23-34 (2013)). Small molecule inhibition of hedgehog pathway activity results in cell death in a number of cancer types (Tang, et al., *N. Eng. J. Med.*, 366 (23): 2180-2188 (2012); Kim, et al., *J. of Clin. Oncol.*, 32: 1-7 (2014).

Hedgehog inhibitor compounds contemplated for use include, for example, those described and disclosed in U.S. Pat. Nos. 7,230,004, 7,812,164; 8,669,365, U.S. Patent Application Publication No. 2008/0287420, U.S. Patent Application Publication No. 2008/0293755 and U.S. Patent Application Publication No. 2013/0109700, the entire disclosures of which are incorporated by reference herein. Examples of other suitable hedgehog inhibitors include those described in U.S. Patent Application Publication Nos. US 2002/0006931, US 2007/0021493 and US 2007/0060546, and International Application Publication Nos. WO 2001/19800, WO 2001/26644, WO 2001/27135, WO 2001/74344, WO 2003/011219, WO 2003/088970, WO 2004/020599, WO 2005/013800, WO 2005/033288, WO 2005/032343, WO 2005/042700, WO 2006/028958, WO 2006/050351, WO 2006/078283, WO 2007/054623, WO 2007/059157, WO 2007/120827, WO 2007/131201, WO 2008/070357, WO 2008/110611, WO 2008/112913, and WO 2008/131354.

Additional examples of hedgehog inhibitors include, but are not limited to, GDC-0449 (also known as RG3616 or vismodegib) described in, e.g., Von Hoff D. et al., *Engl. J. Med.* 361(12):1164-72 (2009); Robarge K. D. et al., *Bioorg Med Chem Lett.*, 19(19):5576-81 (2009); Rudin, C. et al., *New England J. of Medicine*, 361-366 (2009); BMS-833923 (also known as XL139) described in, e.g., in Siu, L. et al., *J. Clin. Oncol.* 2:15s (suppl; abstr 2501) (2010); LDE-225 described, e.g., in Pan S. et al., *ACS Med. Chem. Lett.* 1(3): 130-134 (2010); LEQ-506 described, e.g., in National Institute of Health Clinical Trial Identifier No. NCT01106508; PF-04449913 described, e.g., in National Institute of Health Clinical Trial Identifier No. NCT00953758; hedgehog pathway antagonists disclosed in U.S. Patent Application Publication No. 2010/0286114; SMOi2-17 described, e.g., U.S. Patent Application Publication No. 2010/0093625; SANT-1 and SANT-2 described, e.g., in Rominger C. M. et al., *J. Pharmacol. Exp. Ther.*, 329(3):995-1005 (2009); 1-piperazinyl-4-arylphthalazines or analogues thereof, described in Lucas B. S. et al., *Bioorg. Med. Chem. Lett.*, 20(12):3618-22 (2010).

In certain embodiments, the hedgehog inhibitor is a steroidal alkaloid of the cyclopamine family.

In certain embodiments, the hedgehog inhibitor is a compound of formula (I):

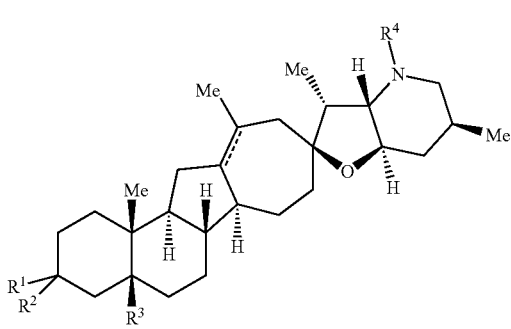

(I)

or a pharmaceutically acceptable form thereof (e.g., a salt and/or solvate) thereof; wherein:

$R^1$ is H, alkyl, —OR, amino, sulfonamido, sulfamido, —OC(O)$R^5$, —N($R^5$)C(O)$R^5$, or a sugar;

$R^2$ is H, alkyl, alkenyl, alkynyl, aryl, cycloalkyl, nitrile, or heterocycloalkyl;

or $R^1$ and $R^2$ taken together form =O, =S, =N(OR), =N(R), =N(NR$_2$), or =C(R)$_2$;

$R^3$ is H, alkyl, alkenyl, or alkynyl;

$R^4$ is H, alkyl, alkenyl, alkynyl, aryl, cycloalkyl, heterocycloalkyl, aralkyl, heteroaryl, heteroaralkyl, haloalkyl, —OR, —C(O)$R^5$, —CO$_2$$R^5$, —SO$_2$$R^5$, —C(O)N($R^5$)($R^5$), [C(R)$_2$]$_g$—$R^5$, —[(W)—N(R)C(O)]$_g$$R^5$, —[(W)—C(O)]$_g$$R^5$, —[(W)—C(O)O]$_g$$R^5$, —[(W)—OC(O)]$_g$$R^5$, —[(W)—SO$_2$]$_g$$R^5$, —[(W)—N($R^5$)SO$_2$]$_q$$R^5$, —[(W)—C(O)N(R)]$_q$$R^5$, —[(W)—O]$_q$$R^5$, —[(W)—N(R)]$_q$$R^5$, —W—NR$_3$$^+$X$^-$ or —[(W)—S]$_q$$R^5$; wherein each W is independently for each occurrence a diradical such as an alkylene; each q is independently for each occurrence 1, 2, 3, 4, 5, or 6; and X$^-$ is an anion (e.g., a halide);

each $R^5$ is independently for each occurrence H, alkyl, alkenyl, alkynyl, aryl, cycloalkyl, heterocycloalkyl, aralkyl, heteroaryl, heteroaralkyl or [C(R)$_2$]$_p$—$R^6$; wherein p is 0-6; or any two occurrences of $R^5$ on the same substituent can be taken together to form a 4-8 membered optionally substituted ring which contains 0-3 heteroatoms selected from N, O, S, and P; and each $R^6$ is independently hydroxyl, —N(R)COR, —N(R)C(O)OR, —N(R)SO$_2$(R), —C(O)N(R)$_2$, —OC(O)N(R)(R), —SO$_2$N(R)(R), —N(R)(R), —COOR, —C(O)N(OH)(R), —OS(O)$_2$OR, —S(O)$_2$OR, —OP(O)(OR)(OR), —NP(O)(OR)(OR), or —P(O)(OR)(OR); and each R is independently H, alkyl, alkenyl, alkynyl, aryl, cycloalkyl or aralkyl; provided that when $R^2$, $R^3$ are H and $R^4$ is hydroxyl; $R^1$ cannot be hydroxyl; provided that when $R^2$, $R^3$, and $R^4$ are H; $R^1$ cannot be hydroxyl; and provided that when $R^2$, $R^3$, and $R^4$ are H; $R^1$ cannot be sugar.

In certain embodiments, $R^1$ is H, hydroxyl, alkoxyl, aryloxy, or amino.

In some embodiments, $R^1$ and $R^2$ taken together along with the carbon to which they are bonded, form =O, =N(OR), or =S.

In other embodiments, $R^3$ is H and/or $R^4$ is H, alkyl, hydroxyl, aralkyl, [C(R)$_2$]$_q$—$R^5$, —[(W)—N(R)C(O)]$_q$$R^5$, —[(W)—N(R)SO$_2$]$_q$$R^5$, —[(W)—C(O)N(R)]$_q$$R^5$, —[(W)—O]$_q$$R^5$, —[(W)—C(O)]$_q$$R^5$, or —[(W)—C(O)O]$_q$$R^5$.

In yet other embodiments, $R^1$ is H or —OR, $R^2$ is H or alkyl, and $R^4$ is H.

In yet other embodiments, $R^2$ is H or alkyl, $R^3$ is H, alkyl, alkenyl, alkynyl, aryl, cycloalkyl, heterocycloalkyl, or aralkyl; and/or $R^4$ is H, alkyl, aralkyl, —[(W)—N(R)C(O)]$_q$$R^5$, —[(W)—N(R)SO$_2$]$_q$$R^5$, —[(W)—C(O)N(R)]$_q$$R^5$, —[(W)—O]$_q$$R^5$, —[(W)—C(O)]$_q$$R^5$, or —[(W) C(O)O]$_q$$R^5$.

In yet other embodiments, $R^1$ is sulfonamido.

Specific examples of hedgehog inhibitors include compounds, or pharmaceutically acceptable salts and/or solvates thereof, described in U.S. Pat. No. 7,812,164, incorporated by reference herein. An illustrative example of a hedgehog inhibitor is the following compound, referred to herein as patidegib, previously referred to as "saridegib" and also known in the art as IPI-926:

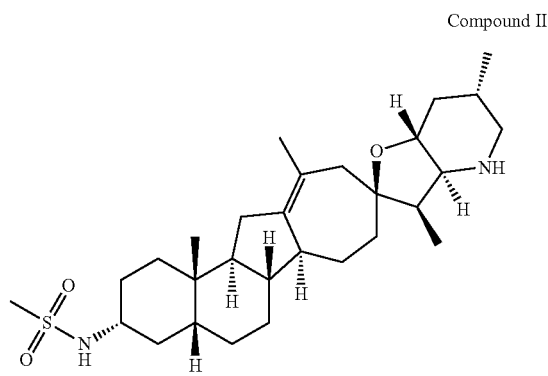

Compound II

The hedgehog inhibitor compounds described herein can be employed in a pharmaceutically acceptable salt form, and in one embodiment, the salt form is the hydrochloride salt of Compound II, identified below as Compound II-a:

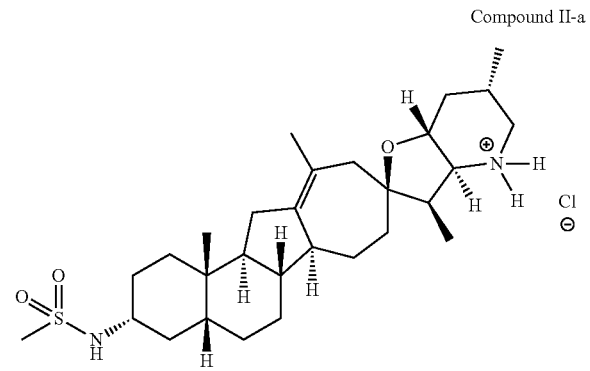

Compound II-a

In certain other embodiments, the hedgehog inhibitor is a triazolyl-triazolone compound according to formula (or compound) III:

Compound III

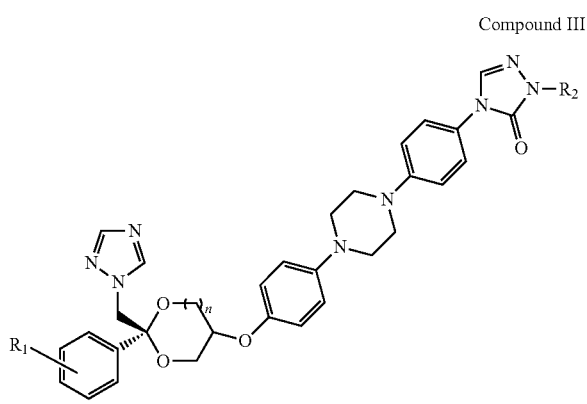

where $R_1$ is one or more independently selected halo groups substituted on the phenyl ring (i.e., the phenyl ring may comprise 1, 2, 3, 4 or 5 $R_1$ groups, that may be the same or different, where each $R_1$ is a halo group). In some embodiments, the halo group is selected from chloro, bromo and fluoro. In one or more embodiments, the phenyl ring comprises a single $R_1$ group that is ortho, meta or para to the attachment to the dioxolane or the dioxane moiety. In yet other embodiments, the phenyl ring comprises two $R_1$ groups that may be positioned in any configuration on the phenyl ring. In a preferred embodiment, the $R_1$ groups are the same. In further embodiments, the phenyl ring comprises three $R_1$ groups, or even four $R_1$ groups, or even five $R_1$ groups. In some embodiments, the $R_1$ groups are the same. Further in reference to Compound III, n is 0 or 1; that is to say, the oxygen containing heterocycle is either dioxane or is dioxolane. In one preferred embodiment, n is 0. The substituent attached to the triazolone ring, $R_2$, is typically a branched or linear lower alkyl group; examples include but are not limited to methyl, ethyl, propyl, isopropyl, butyl, isobutyl and tert-butyl.

In some embodiments of Compound (III), n is 0 and $R_1$ represents two chloro groups. In some embodiments, $R_1$ represents two chloro groups that are positioned ortho- and para- to the bond connecting the phenyl group to a 1,3-dioxolane ring. In some embodiments of Compound (III), $R_2$ is —CCH$_3$CH$_2$CH$_3$. In certain other preferred embodiments, Compound III is itraconazole (Compound III-a, (2R,4S)-rel-1-(butan-2-yl)-4-{4-[4-(4-(4-{[(2R,4S)-2-(2,4-dichlorophenyl)-2-(1H-1,2,4-triazol-1-ylmethyl)-1,3-dioxolan-4-yl]methoxy}phenyl)piperazin-1-yl]phenyl}-4,5-dihydro-1H-1,2,4-triazol-5-one)). Itraconazole possesses three chiral centers, and may be used in the instant topical formulations as a mixture of racemates, or in optically pure form (i.e., of any one particular stereoisomer), or as a mixture enriched in one or more of the stereoisomers. Itraconazole may also be in the form of a pharmaceutically acceptable salt. The commercially available drug (marketed as an antifungal) is provided as a stereoisomeric mixture of four stereoisomers, i.e., a mixture of two racemates, all of the stereoisomers having a cis configuration (where the hydrogen and the 2,4-dichlorophenyl group at the two chiral centers are on the same side of the dioxolane ring). Shi et al., *ACS Med. Chem. Lett.*, 2010, 1, 155-159. In one or more embodiments, a composition or delivery system comprises itraconazole as a stereoisomeric mixture of four stereoisomers, i.e., a mixture of two racemates, all of the stereoisomers having a cis configuration.

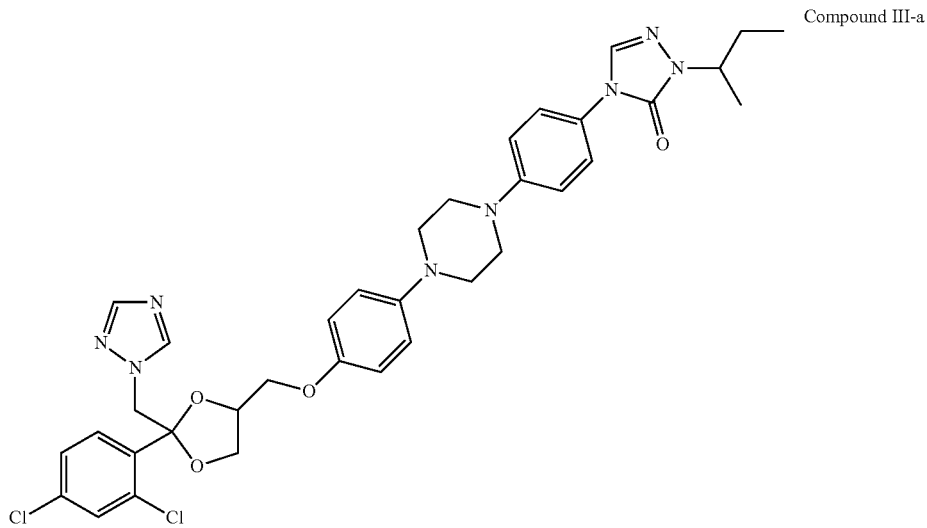 [SMILES: CCC(C)n1ncn(-c2ccc(N3CCN(c4ccc(OCC5COC(Cn6cncn6)(c6ccc(Cl)cc6Cl)O5)cc4)CC3)cc2)c1=O]

Compound III-a

Itraconazole is a potent antagonist of the Hedgehog (Hh) signaling pathway that acts by a mechanism distinct from its inhibitory effect on fungal sterol biosynthesis. Itraconazole appears to act on the essential Hh pathway component Smoothened (Smo) by a mechanism distinct from that of cyclopamine and other known Smo antagonists, and prevents the ciliary accumulation of Smo normally caused by Hh stimulation (Kim, J., et al., *Cancer Cell.*, 2010 Apr. 13; 17(4): 388-399).

B. Exemplary Solvent Systems and Compositions Comprising the Solvent Systems

Solvent systems for topical administration of a hedgehog inhibitor compound having a structure exemplified by Compound I or Compound III are described. As an exemplary compound in the solvent systems, a salt form of Compound II (patidegib), the hydrochloride salt form shown as Compound II-a, was used in some of the studies. Additional studies in which another exemplary compound, itraconazole, was used, are also described below (and in the examples which follow).

In a study detailed in Example 1, five topical formulations were prepared. Ingredients in the compositions are summarized in Table 1 and in the tables presented in Example 1.

TABLE 1

Exemplary Topical Compositions

| Name | Ethanol/PG[1] Ratio | DEGEE[2] | benzyl alcohol | isostearic acid | phenoxy ethanol | buffer[3] (pH 7.5) | HPC | patidegib |
|---|---|---|---|---|---|---|---|---|
| SS5  | 1.00 | 18.7 | 1.9 | —    | —   | 35.6 | 2.0 | 4.4 |
| SS6  | 1.50 | 18.4 | 1.8 | —    | —   | 25.7 | 2.0 | 6.2 |
| SS14 | 1.25 | 18.8 | —   | —    | 0.9 | 31.0 | 2.0 | 5.0 |
| SS20 | 1.25 | —    | 1.9 | —    | —   | 49.5 | 2.0 | 3.7 |
| SS22 | 1.56 | —    | 1.9 | 14.2 | —   | —    | 2.0 | 4.4 |

[1]PG = propylene glycol
[2]DEGEE = diethylene glycol monoethyl ether
[3]buffer pH 7.5 comprised of boric acid (0.16< adjusted with sodium hydroxide (0.1M)

The solvent system in one embodiment comprises a binary solvent system of a monohydric alcohol having between about 1-6 carbon atoms and a polyol. In one embodiment, the monohydric alcohol is a primary alcohol selected from methanol, ethanol, 1-propanol, butanol, amyl alcohol (pentanol) and cetyl alcohol (hexadecane-1-ol). In another embodiment the monohydric alcohol is a secondary alcohol such as isopropyl alcohol, and in another embodiment the monohydric alcohol is an aliphatic secondary alcohol, e.g., a secondary alcohol lacking a ring structure. In yet another embodiment, the monohydric alcohol is one having 2-4 or 2-3 carbon atoms, and in another embodiment it is a diol with 2-4 or 2-3 carbon atoms. In one embodiment the polyol is a diol selected from ethylene glycol, propylene glycol, and 1,4-butanediol. The ratio of the monohydric alcohol to polyol is between about 0.9-1.8 or 0.9-1.7, preferably between about 0.95-1.60 or between about 1.0-1.56.

The solvent system in another embodiment is a ternary solvent system comprised of the monohydric alcohol and the polyol described above in the binary solvent system and diethylene glycol monoethyl ether (DEGEE), benzyl alcohol, or both. In this ternary system, the monohydric alcohol to polyol is between about 0.9-1.8 or about 0.9-1.7, preferably between about 0.95-1.60 or between about 1.0-1.56. When the third component is DEGEE, the ratio (w/w) of monohydric alcohol to DEGEE is within about 10-20% of the ratio (w/w) of monohydric alcohol to polyol (or diol). In another embodiment, when the third component is DEGEE, the ratio (w/w) of monohydric alcohol to DEGEE is the same as the ratio (w/w) of monohydric alcohol to polyol (or diol).

The solvent system in another embodiment is a quaternary solvent system comprised of a monohydric alcohol monohydric alcohol having between about 1-6 carbon atoms and a polyol, as described above in the binary solvent system, and diethylene glycol monoethyl ether (DEGEE), benzyl alcohol, or both, and as the fourth component, phenoxyethanol. In this quaternary solvent system, the monohydric alcohol to polyol is between about 0.9-1.8 or about 0.9-1.7, preferably between about 0.95-1.60 or between about 1.0-1.56. When the third component is DEGEE, the ratio (w/w) of monohydric alcohol having between about 1-6 carbon atoms to DEGEE is within about 10-20% of the ratio (w/w) of monohydric alcohol to polyol (or diol). In another embodiment, when the third component is DEGEE, the ratio (w/w) of monohydric alcohol to DEGEE is the same as the ratio (w/w) of monohydric alcohol to polyol (or diol). The phenoxyethanol is present in the system in an amount between about 0.01-3 wt % or between about 0.07-2 wt %.

In another embodiment, the solvent system is a quaternary solvent system comprised of (i) a monohydric alcohol having between 1-6 carbon atoms, (ii) a polyol, (iii) DEGEE, benzyl alcohol, or both, and (iv) a fatty acid comprising between about 13-22 carbon atoms or a buffer. In this embodiment of a quaternary solvent system, the monohydric alcohol, polyol and DEGEE or benzyl alcohol or both are as described above for the ternary solvent system, with the additional feature that a fatty acid comprising between about 13-22 carbon atoms or a buffer is added to the system. In embodiments where a fatty acid comprising between about 13-22 carbon atoms is included in the solvent system, the fatty acid can be, in one embodiment, a saturated fatty acid. Exemplary saturated fatty acids include myristic acid (C14), isopropylmyristic acid, palmitic acid (C16), stearic acid (C18) and arachidic acid (C22). In an exemplary embodiment, the saturated fatty acid is isostearic acid. In one embodiment, the exemplary quaternary solvent system additionally comprises phenoxyethanol, rendering the system a quinary solvent system. The phenoxyethanol is present in the system in an amount between about 0.01-3 wt % or between about 0.07-2 wt %.

The composition, in one embodiment, can comprise a substance to increase viscosity, sometimes referred to as a thickening agent or gelling agent. Exemplary agents include gums (e.g., xanthan gum, guar gum), pectins, starches, and synthetic polymers, such as polyacrylic acid and hydroxyalkylcelluloses, such as hydroxyethylcellulose, hydropropylcellulose, and hydroxypropylmethylcellulose. The amount of viscosity increasing agent in the composition can range from about 0.5-10 wt %, preferably between about 0.5-5 wt % or about 0.5-3 wt %. In one embodiment, the thickening agent is hydroxyethylcellulose, and in another embodiment is hydroxyethylcellulose with a molecular weight of between about 800,000-1,250,000 Daltons.

Using these guiding principles, the intracutaneous delivery of patidegib into human skin from the five formulations set forth in Table 1 was tested in vitro using human skin in a Franz diffusion cell. As an initial indicator of partitioning of patidegib from the test formulations into the *stratum corneum*, the concentration of patidegib in the receiver fluid of each Franz cell was measured by taking aliquots of receiver fluid at various time points between 14-48 hours. After the 48 hour topical application to the skin, the layers of the skin were individually analyzed for concentration of patidegib in the *stratum corneum*, epidermis and dermis to assess intracutaneous delivery. The results are shown in FIGS. 1A-1B.

Figure 1B:
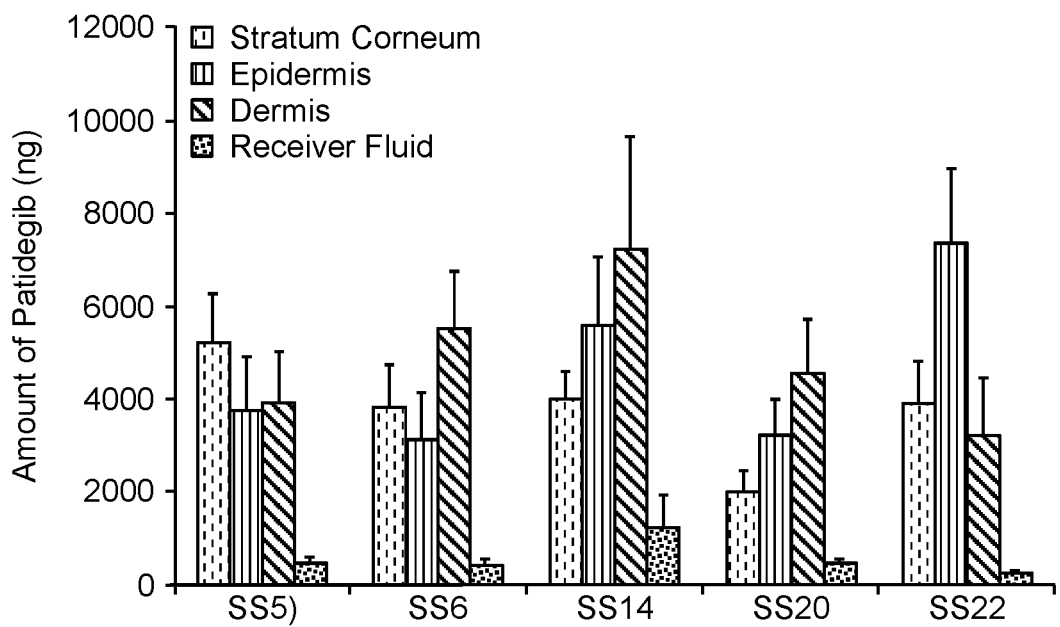
FIG. 1B is a bar graph showing the amount of patidegib, in ng, at various locations in a skin sample after 48 hours of in vitro contact with five exemplary compositions of patidegib in a solvent system, where the bars correspond to amount of patidegib in the stratum corneum (dashes), epidermis (horizontal fill), dermis (diagonal fill) and receiver fluid (dots)

FIG. 1A shows the cumulative amount of patidegib permeated across human skin in vitro, in ng/cm$^2$, as a function of time, in hours, for the five compositions of patidegib in the exemplary solvent systems set forth in Table 1. The formulations identified as SS5 (open squares), SS6 (closed triangles), SS20 (x symbols) and SS14 (closed diamonds) each provided a cumulative amount of patidegib of at least about 250 ng/cm$^2$ in 24 hours. Two of the formulations, SS20 (x symbols) and SS14 (closed diamonds), achieved a cumulative amount of patidegib of at least about 500 ng/cm$^2$ in 36 hours. The formulation identified as SS14 achieved a cumulative amount of patidegib of at least about 1000 ng/cm$^2$ in 36 hours. The non-aqueous formulation, SS22 (open diamonds), had the lowest flux of patidegib of the formulations tested, yet provided a cumulative amount delivered across the skin of about 250 ng/cm$^2$ in 40 hours.

The desired topical formulation is one that achieves partitioning of the hedgehog inhibitor compound from the topical formulation into the *stratum corneum*, diffusion across the *stratum corneum*, and retention in the epidermis and/or dermis. Thus, to assess the ability of the formulations to achieve intracutaneous delivery rather than transdermal delivery, the concentration of hedgehog inhibitor compound in the *stratum corneum*, epidermis and dermis was measured after 48 hours topical exposure to the test formulations. Results of the analysis of the layers of the skin for concentration of patidegib are shown in FIG. 1B. The amount of patidegib delivered to the dermis (bars with diagonal fill) was highest for the formulations identified as SS6 and SS14, which each provided greater than 5000 ng patidegib to the dermis after 48 hours of topical application. The formulation identified as SS22 delivered greater than 7000 ng of patidegib to the epidermis (bars with horizontal fill) after 48 hours of contact with the skin.

Accordingly, in one embodiment, a topical formulation of patidegib is provided that achieves after 24 hours or after 48 hours of topical application in vitro an amount of patidegib in the epidermis, the dermis or the epidermis and dermis combined that exceeds the amount of patidegib in the *stratum corneum*. In another embodiment, a topical formulation of patidegib is provided that achieves after 24 hours or after 48 hours of topical application in vitro an amount of patidegib in the epidermis, the dermis, or the epidermis and dermis combined that exceeds by at least about 15%, 25% or 40% the amount of patidegib in the *stratum corneum*. In another embodiment, a topical formulation of patidegib is provided that achieves after 24 hours or after 48 hours of topical application in vitro an amount of patidegib in the epidermis, the dermis, or the epidermis and dermis combined that exceeds by at least about 150%, 200%, 300%, 350% or 400% the amount of patidegib in the receiver fluid. In another embodiment, a topical formulation of patidegib is provided that achieves after 24 hours or after 48 hours of topical application in vitro an amount of patidegib in the epidermis, the dermis, or the epidermis and dermis combined that is at least about 1.5, 2, 3, 3.5, 4 or 5 fold greater than the amount of patidegib in the receiver fluid.

The drug in each layer of the skin is tabulated in Table 2 in concentration units of micromolar.

TABLE 2

Concentration of patidegib (μM) in each of the stratum corneum, epidermis and dermis 48 hours after topical application.

| Formulation | Concentration of patidegib (μM) in stratum corneum. | Concentration of patidegib (μM) in epidermis | Concentration of patidegib (μM) in dermis |
|---|---|---|---|
| SS5 | 17080 | 1233 | 445 |
| SS6 | 12593 | 1039 | 629 |
| SS14 | 13238 | 1851 | 823 |
| SS20 | 6588 | 1057 | 521 |
| SS22 | 12880 | 2425 | 367 |

The half maximal effective concentration of patidegib for inhibition of cellular hedgehog pathway is 0.007 μM (Tremblay et al., *J. Med. Chem.*, 52(14):4400-44118 (2009)). The formulations identified herein as SS5, SS6, SS14, SS20 and SS22 each provided for delivery of patidegib to the epidermis or dermis in an amount sufficient for therapy; that is, in one embodiment, an amount that provides a half-maximal effective concentration in the dermis, epidermis or combined dermis and epidermis within about 24 hours after topical application of the composition.

As mentioned above, the compound is included in the composition in an amount between about 0.1-10 wt %, or between about 1-10 wt %, alternatively between about 2-8 wt % or about 3-7 wt %. It will be appreciated that adjustments to the amount of compound added may vary according to the potency of the compound, although the weight percent of compound in the final formulation will typically be within the stated ranges.

In another study, detailed in Example 2, additional topical compositions were prepared and the delivery of patidegib from each was studied in vitro. The topical compositions of this study were variations of the formulations identified above as SS14 and SS22, which are included in Table 3 below for ease of reference.

TABLE 3

Exemplary Topical Compositions

| | Aqueous Formulations | | | Non-aqueous Formulations | | |
|---|---|---|---|---|---|---|
| | SS14 wt % | SS14.10 wt % | SS14.19 wt % | SS22 wt % | SS22.7 wt % | SS22.9 wt % |
| ethanol | 23.5 | 7.4 | — | 47.3 | — | — |
| isopropyl alcohol | — | — | — | — | 49.1 | 49.5 |
| propylene glycol | 18.8 | 4.9 | — | 30.3 | 31.4 | — |
| benzyl alcohol | — | — | — | 1.9 | — | — |
| DEGEE* | 18.8 | 9.8 | — | | | |
| isostearic acid | — | — | — | 14.2 | 16.7 | 24.7 |
| isopropyl myristate | — | — | — | — | — | 23.7 |
| phenoxyethanol | 0.9 | 1.0 | 1.0 | | | |
| buffer | 31.0 | — | — | — | — | — |
| deionized water | — | 74.2 | 96.9 | — | — | — |
| hydroxypropyl cellulose | 2.0 | 2.0 | 2.0 | 2.0 | 2.0 | 2.0 |
| patidegib | 5.0 | 0.75 | 0.1 | 4.4 | 0.75 | 0.1 |
| Ratio monohydric alcohol/diol | 1.25 | 1.51 | 0 | 1.6 | 1.6 | 0 |

*DEGEE = diethylene glycol monoethyl ether (Transcutol ® P)

Figure 2A:
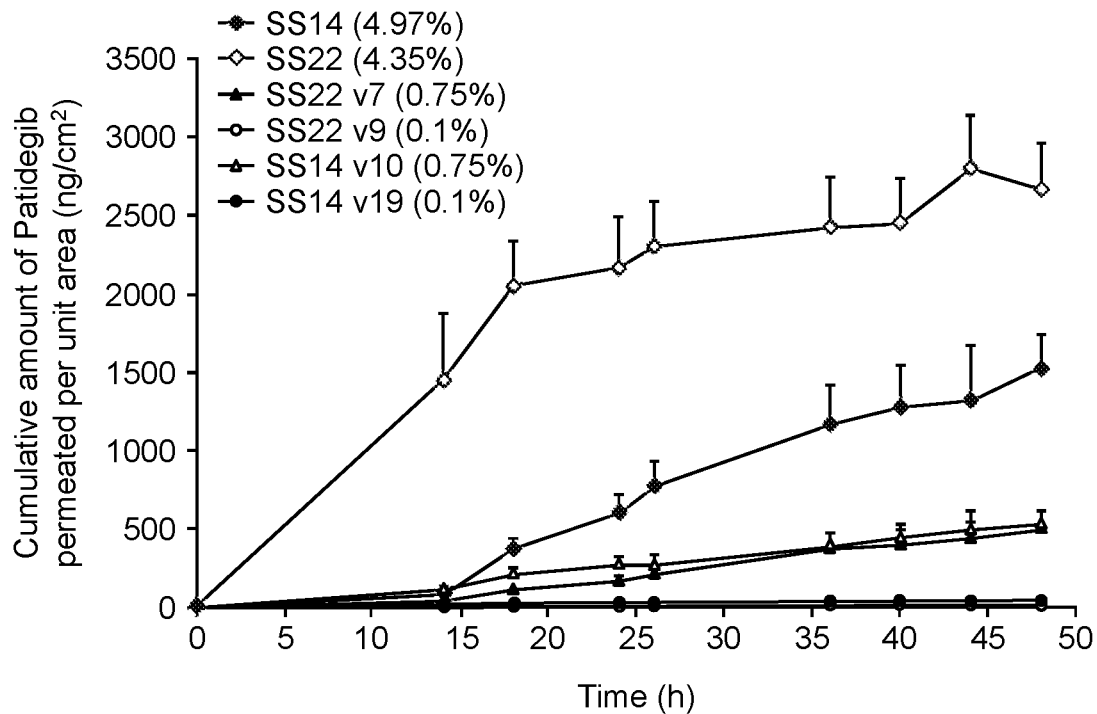
FIG. 2A is a graph showing the cumulative amount of patidegib permeated across human skin in vitro, in $ng/cm^2$, as a function of time, in hours, for six exemplary compositions of patidegib in a solvent system.

The intracutaneous delivery of patidegib from the formulations set forth in Table 3 was tested in vitro using human skin. As an initial indicator of partitioning of patidegib from the formulation into the *stratum corneum*, the concentration of patidegib in the receiver fluid of the Franz cell was measured by taking aliquots of receiver fluid at various time points between 14-48 hours. After the 48 hour topical application to the skin, the layers of the skin were analyzed for drug concentration to measure intracutaneous delivery. The results are shown in FIGS. 2A-21B. FIG. 2A shows the cumulative amount of patidegib permeated across human skin in vitro, in ng/cm$^2$, as a function of time, in hours. The non-aqueous formulation SS22 (open diamonds) and the aqueous formulation SS14 (closed diamonds) achieved the highest permeation of patidegib with at least about 500 ng/cm$^2$ in 24 hours and at least about 1000 ng/cm$^2$ in 36 hours. The study reveals that decreasing the concentration of hedgehog inhibitor compound decreases the cumulative amount delivered across the skin in both the aqueous and non-aqueous formulations (e.g., compare SS22.7 (non-aqueous, closed triangles) and SS14.10 (aqueous, open triangles)). Formulations with no diol, and thus a ratio of monohydric alcohol to diol of zero, and with 0.1 wt % patidegib had the lowest amount of patidegib delivered across the skin (e.g., SS22.9 (open circles) and SS14.19 (closed circles)).

Figure 2B:
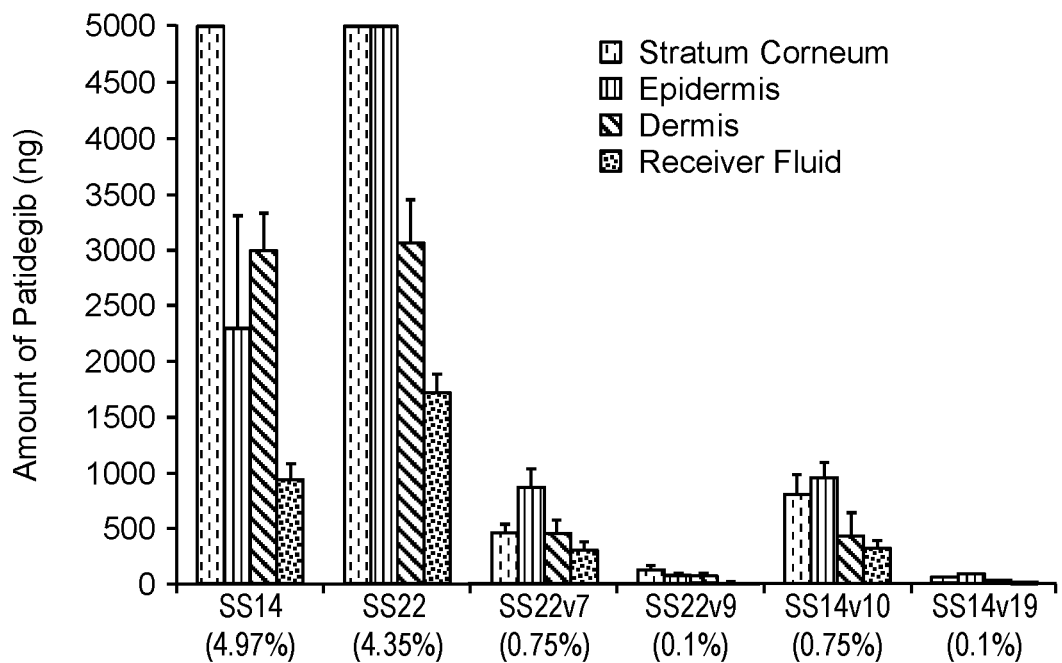
FIG. 2B is a bar graph showing the amount of patidegib, in ng, at various locations in a skin sample after 48 hours of in vitro contact with six exemplary compositions of patidegib in a solvent system, where the bars correspond to amount of patidegib in the stratum corneum (dashes), epidermis (horizontal fill), dermis (diagonal fill) and receiver fluid (dots)

At the end of the 48 hour in vitro permeation investigation, the skin was removed from the Franz diffusion cells and analyzed for patidegib concentration in the layers of the skin. The results are shown in FIG. 2B, where the bars for each formulation correspond to stratum corneum (dashes), epidermis (horizontal fill), dermis (diagonal fill) and receiver fluid (dots). The amount of patidegib delivered to the dermis (bars with diagonal fill) was highest for the formulations identified as SS14 and SS22, which each provided greater than 2900 ng of patidegib to the dermis after 48 hours of topical application. The formulation identified as SS22 delivered greater than 5000 ng of patidegib to the epidermis (bars with horizontal fill) after 48 hours of contact with the skin. The formulations with less than 1 wt % drug compound (SS14.10, SS14.19, SS22.7 and SS22.9) delivered less than about 1000 ng of drug to the epidermis or dermis after 48 hour topical application.

The drug in each layer of the skin is tabulated in Table 4 in concentration units of micromolar (μM).

TABLE 4

Concentration of patidegib (μM) in each of the stratum corneum, epidermis and dermis 48 hours after topical application.

| Formulation | Concentration of patidegib (% w/w) | Concentration of patidegib (μM) in Stratum corneum | Concentration of patidegib (μM) in epidermis | Concentration of patidegib (μM) in dermis |
|---|---|---|---|---|
| SS14 | 4.97 | 37819 | 758 | 341 |
| SS14.10 | 0.75 | 2687 | 315 | 50 |
| SS14.19 | 0.10 | 215 | 35 | 5 |
| SS22 | 4.35 | 51911 | 2458 | 349 |
| SS22.7 | 0.75 | 1538 | 287 | 53 |
| SS22.9 | 0.10 | 459 | 26 | 9 |

Accordingly, in one embodiment, the topical composition is one where the hedgehog inhibitor compound has a saturation solubility in the solvent system of between about 0.1-10 wt %, alternatively between about 2.5-8 wt %, and the solvent system comprises between about 15-60 wt % ethanol and between about 10-50 wt % propylene glycol. In another embodiment, the hedgehog inhibitor compound has a saturation solubility in the solvent system of between about 0.1-10 wt % or between about 2.5-8 wt % and is present in the composition in an amount between about 0.1-10 wt % or between about 2-8 wt %, or between about 2.5-7 wt %, or between about 2.8-7.5 or between about 3.0-7.0 wt %.

In another embodiment, the concentration of hedgehog inhibitor compound is between about 0.1-10 wt % or between about 2-8 wt %, between about 2.5-7 wt %, between about 2.8-7.5 or between about 3.0-7.0 wt %.

In another study, detailed in Example 3, the formulations identified as SS14 and SS22 were prepared with lower amount of patidegib and tested in vitro using human skin in a Franz diffusion cell. The aqueous formulation SS14 comprises of about 5 wt % patidegib and two comparative formulations were prepared that had 0.75 wt % (SS14D2) and 0.1 wt % (SS14D1) patidegib. The non-aqueous formulation SS22 comprises about 4.4 wt % patidegib and two comparative formulations were prepared that had 0.75 wt % (SS22D2) and 0.1 wt % (SS14D1) patidegib. The compositions are set forth in Example 3.

Figure 3A:
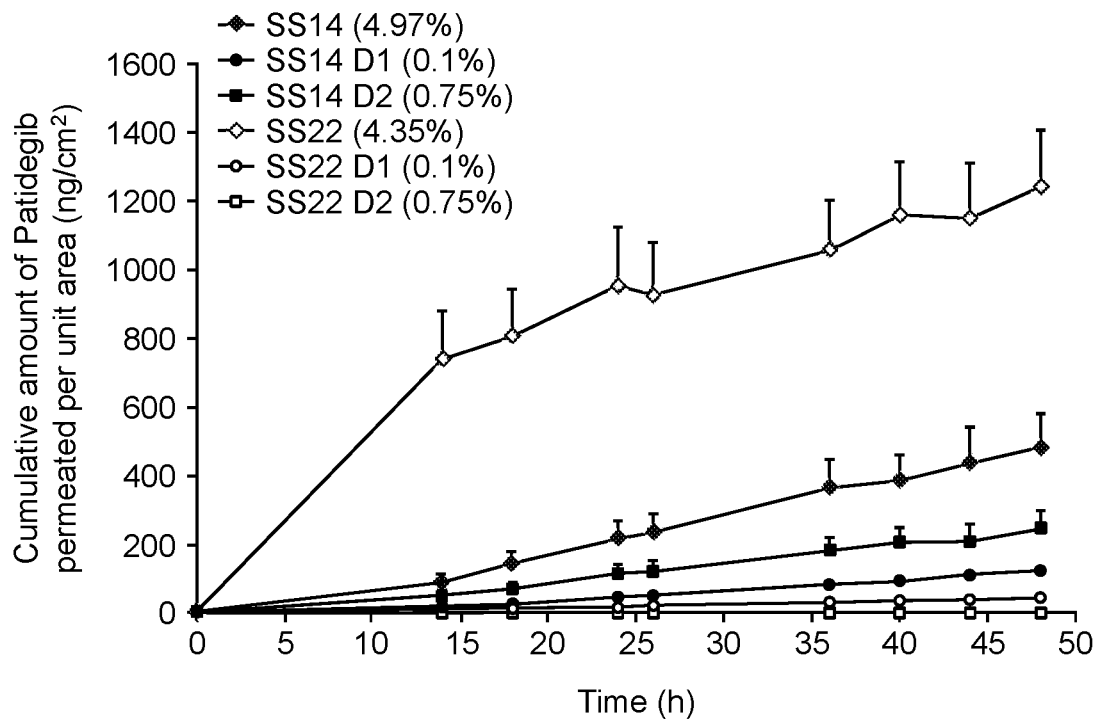
FIG. 3A is a graph showing the cumulative amount of patidegib permeated across human skin in vitro, in $ng/cm^2$, as a function of time, in hours, for six exemplary compositions of patidegib in a solvent system.
Figure 3B:
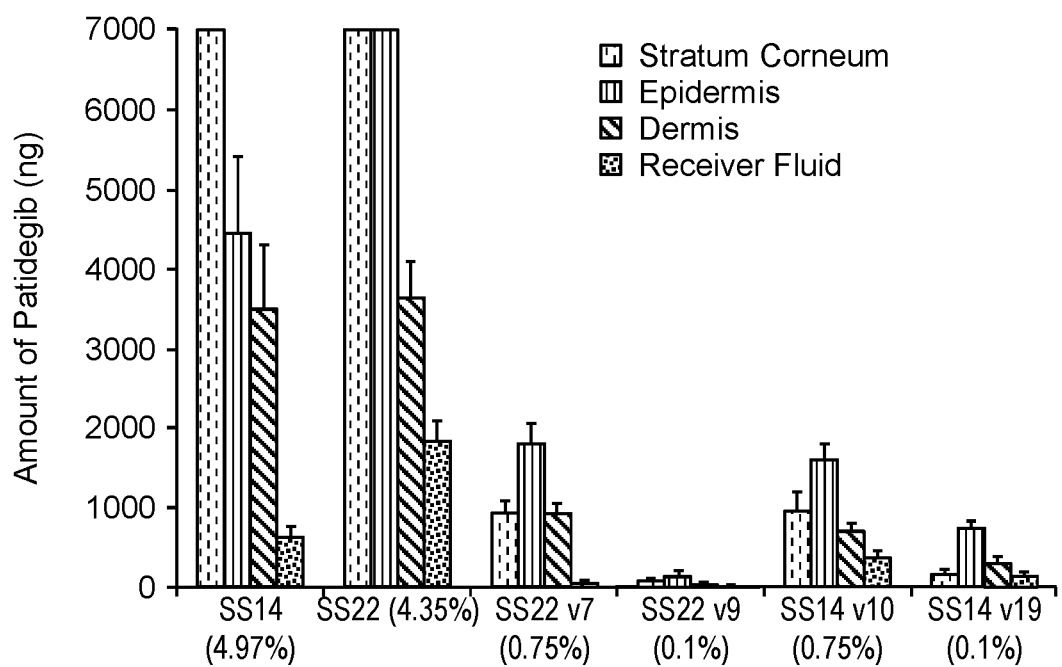
FIG. 3B is a bar graph showing the amount of patidegib, in ng, at various locations in a skin sample after 48 hours of in vitro contact with six exemplary compositions of patidegib in a solvent system, where the bars correspond to amount of patidegib in the stratum corneum (dashes), epidermis (horizontal fill), dermis (diagonal fill) and receiver fluid (dots).

As an initial indicator of partitioning of patidegib from the formulation into the *stratum corneum*, the concentration of patidegib in the receiver fluid of the Franz cell was measured by taking aliquots of receiver fluid at various time points between 14-48 hours. After the 48 hour topical application to the skin, the layers of the skin were analyzed for drug concentration to measure intracutaneous delivery. The results are shown in FIGS. 3A-3B. FIG. 3A shows the cumulative amount of patidegib permeated across human skin in vitro, in ng/cm$^2$, as a function of time, in hours. The non-aqueous formulation SS22 (open diamonds) achieved the highest cumulative amount of patidegib permeated across the skin, with at least about 750 ng/cm$^2$ in 24 hours and at least about 1000 ng/cm$^2$ in 36 hours. The aqueous formulations SS14 (closed diamonds), SS14D1 (closed circles) and SS14D2 (closed squares) yielded a higher cumulative amount of patidegib permeated across the skin relative to the non-aqueous formulations with 0.75 wt % and 0.1 wt % patidegib (respectively, SS22D2, open squares and SS22D1, open circles). The study confirms the results observed in Examples 1 and 2 that the topical compositions with at least about 2 wt % drug compound, preferably at least about 2.5 wt % drug compound in a solvent system with a monohydric alcohol and a diol in a ratio of between about 1.0-1.8 or 1.2-1.6 provide a topical composition that when applied to the skin of a subject in need delivers a therapeutically effective amount at times between 10-60 hours after topical application, or at times of 10-50 hours, or 12-48 hours.

At the end of the 48 hour in vitro permeation investigation, the skin was removed from the Franz diffusion cells and analyzed for patidegib concentration in the layers of the skin. The results are shown in FIG. 3B, where the bars for each formulation correspond to stratum corneum (dashes), epidermis (horizontal fill), dermis (diagonal fill) and receiver fluid (dots). The amount of patidegib delivered to the dermis (bars with diagonal fill) was highest for the formulations identified as SS14 and SS22, which each provided greater than 3000 ng patidegib to the dermis after 48 hours of topical application. The formulation identified as SS22 delivered more drug to the dermis (bars with diagonal fill) than the epidermis (bars with horizontal fill) after 48 hours of contact with the skin. The formulations with less than 1 wt % drug compound (SS14D1, SS14D2, SS22D1 and SS22D2) delivered less than about 1000 ng of drug to the dermis after 48 hours topical application.

Accordingly, in one embodiment, a topical formulation of patidegib is provided that achieves after 24 hours or after 48 hours of topical application in vitro an amount of patidegib in the epidermis, the dermis or the epidermis and dermis combined that exceeds the amount of patidegib in the *stratum corneum*. In another embodiment, a topical formulation of patidegib is provided that achieves after 24 hours or after 48 hours of topical application in vitro an amount of patidegib in the epidermis, the dermis, or the epidermis and dermis combined that exceeds by at least about 15%, 25% or 40% the amount of patidegib in the *stratum corneum*. In another embodiment, a topical formulation of patidegib is provided that achieves after 24 hours or after 48 hours of topical application in vitro an amount of patidegib in the epidermis, the dermis, or the epidermis and dermis combined that exceeds by at least about 150%, 200%, 300%, 350% or 400% the amount of patidegib in the receiver fluid. In another embodiment, a topical formulation of patidegib is provided that achieves after 24 hours or after 48 hours of topical application in vitro an amount of patidegib in the epidermis, the dermis, or the epidermis and dermis combined that is at least about 1.5, 2, 3, 3.5, 4 or 5 fold greater than the amount of patidegib in the receiver fluid.

The drug in each layer of the skin is tabulated in Table 5 in concentration units of micromolar ($\mu$M).

TABLE 5

Concentration of patidegib ($\mu$M) in each of the stratum corneum, epidermis and dermis 48 hours after topical application.

| Formulation | Concentration of patidegib (% w/w) | Concentration of patidegib ($\mu$M) in Stratum corneum | Concentration of patidegib ($\mu$M) in epidermis | Concentration of patidegib ($\mu$M) in dermis |
| --- | --- | --- | --- | --- |
| SS14 | 4.97 | 16226 | 1470 | 401 |
| SS14D1 | 0.10 | 553 | 247 | 35 |
| SS14D2 | 0.75 | 3245 | 534 | 81 |
| SS22 | 4.35 | 7329 | 1093 | 415 |
| SS22D1 | 0.10 | 286 | 49 | 5 |
| SS22D2 | 0.75 | 3118 | 597 | 107 |

The stability of several exemplary formulations was studied, as detailed in Example 4. The formulations detailed in Example 1 were stored for four weeks storage at 25° C. and at 40° C. and stability was assessed by analyzing the formulations for patidegib content. The results showed that the formulations were stable at room temperature (20-25° C.) and up to 40° C. for at least about 4 weeks, as evidenced by no degradation of patidegib. Accordingly, in one embodiment, compositions are provided that are stable, as evidenced by the patidegib content being between 95-105% of the theoretical patidegib content and/or the patidegib content at time zero (t=0), at room temperature.

In one embodiment, the formulation is an alcoholic solution. In such a formulation, the carrier is typically an admixture of monohydroxy alcohols and polyols. The formulation may optionally contain at least one penetration enhancer. Examples of suitable monohydroxy alcohols include, for example, ethanol, propanol, butanol and benzyl alcohol. Reference herein to "ethanol" includes absolute alcohol, as well as "alcohol USP" and all denatured forms of 95% ethanol. As used herein, the term "propanol" refers to all isomeric forms, including n-propanol and isopropanol, and the term "butanol" refers to all isomeric forms, including, for example, n-butanol, iso-butanol and sec-butanol. In one embodiment, the alcohol is selected from the group comprising ethanol, isopropyl alcohol, and benzyl alcohol, with ethanol being particularly useful.

Examples of suitable polyols include, for example, propylene glycol, dipropylene glycol, hexylene glycol, 1,3-butylene glycol, liquid polyethylene glycols, such as polyethylene glycol200 (PEG-200) and polyethylene glycol400 (PEG-400). A particularly useful polyol is propylene glycol.

For those formulations that are alcoholic solutions or aqueous-alcoholic solutions, the polyol will typically be present in the quantity of from about 0 to about 80% w/w, more typically about 10 to about 25% w/w. The monohydroxy alcohol will be present in the quantity of about 10 to about 99.9% w/w, more typically from about 40 to about 90% w/w. One example of such an alcoholic solution is a formulation containing about 1% w/v of Compound, about 10 to 30% w/w of a polyol, and about 40 to about 90% w/w of a monohydroxy alcohol.

Minor amounts of water can also be included in the formulation. Optionally a penetration enhancer may be incorporated into these alcoholic solutions. In one embodiment, the formulation contains from about 10% to about 25% (w/w) of a polyol, from about 50% to about 70% (w/w) of a monohydroxy alcohol and from about 1% to about 30% (w/w) of a penetration enhancer. In a second embodiment, the formulation contains from about 10% to about 25% (w/w) of a polyol selected from the group consisting of propylene glycol, dipropylene glycol, hexylene glycol, 1,3-butylene glycol, polyethylene glycol, and glycerol, from about 50% to about 70% (w/w) of a monohydroxy alcohol selected from the group consisting of ethanol, isopropyl alcohol and benzyl alcohol and from about 1% to about 30% (w/w) of a penetration enhancer selected from the group consisting of isopropyl myristate, cyclopentadecanolide and propylene glycol dicaprylate/dicaprate. In a more specific embodiment, the formulation contains from about 10% to about 25% (w/w) of propylene glycol, from about 50% to about 70% (w/w) of ethanol, and from about 1% to about 30% (w/w) of isopropyl myristate. More specifically, the formulation contains about 0.5 to about 3 w/v % of Compound, about 20% (w/w) of a propylene glycol, about 60% (w/w) of ethanol and about 20% (w/w) of isopropyl myristate.

Additional studies were conducted on exemplary topical formulations comprising the hedgehog inhibitor, itraconazole. Since itraconazole is a poorly water soluble drug, solubility studies were initially conducted to assess compound solubility in a variety of solvents. For ease of reference, the following formulation descriptions are described in the context of itraconazole as the hedgehog inhibitor compound, although any suitable hedgehog inhibitor compound, in particular those having structural and physicochemical properties similar to itraconazole may be used. Following initial screening experiments, an initial set of 13 preliminarily optimized formulations was prepared comprising various combinations of solvents and system components as described in Example 6. The combination of solvents selected for the initially optimized formulations were determined based upon solubility of the hedgehog inhibitor compound, e.g., itraconazole, stability of drug in the formulation upon storage, solvent compatibility. An additional consideration is skin permeability to achieve a localized skin effect with minimal or no systemic absorption (to be described in greater detail below). The solvent systems explored in Example 6 demonstrated acceptable solvent compatibility and drug stability results, and were then reformulated as non-aqueous gels for topical administration. Formulations for topical delivery may be in any form suitable for application to the skin, e.g., may be in the form of liquids, gels, ointments, creams, aerosols, and the like.

Based upon extensive screening studies, certain features of preferred topical formulations were determined. Topical formulations for administering a hedgehog inhibitor compound comprise a solvent system as follows. In one or more embodiments, the solvent system comprises an aliphatic monohydric alcohol having between 1-6 carbon atoms and a lower alkyl end-capped oligomeric alkylene glycol in a w/w ratio of between about 0.8 and 2.6. Suitable monohydric alcohols are as described above. For example, in one or more embodiments, the monohydric alcohol is a primary aliphatic alcohol selected from methanol, ethanol, 1-propanol, butanol, amyl alcohol (pentanol) and hexanol. Alternatively, the monohydric alcohol is a secondary alcohol such as isopropyl alcohol, or sec-butyl alcohol. In yet another embodiment, the monohydric alcohol is one having 2-4 or 2-3 carbon atoms. Exemplary solvent systems are at least ternary solvent systems comprising three different solvents each present in the solvent system in a w/w percentage greater than 10 weight percent. Thus, in reference to formulations directed to the exemplary hedgehog inhibitor, itraconazole, a binary solvent system, or a ternary solvent system, or a quaternary solvent system is one in which only two solvents, or only three solvents, or only four solvents, respectively, is present in an amount greater than 10 w/w percent. The w/w ratio of monohydric alcohol to lower alkyl end-capped oligomeric alkylene glycol is typically between 0.8 and 2.6, or is preferably between about 1.0 and 2.4, or more preferably from 1.0 and 2.3. Exemplary w/w ratios include 0.85, 0.90, 0.95, 1.0, 1.1, 1.2, 1.3, 1.4, 1.5, 1.6, 1.7, 1.8, 1.9, 2.0, 2.1, 2.2, 2.3, 2.4, and 2.5, including any and all ranges in between any two of the foregoing values.

One illustrative lower alkyl end-capped oligomeric alkylene glycol suitable for use in the instant compositions (with any of the hedgehog inhibitor compounds disclosed herein) is diethylene glycol monoethyl ether (DEGEE). In one or more embodiments, the lower alkyl end-capped oligomeric alkylene glycol is end-capped with a lower alkyl group, i.e., an aliphatic C1-C6 group, modifying the terminal hydroxyl group. In this embodiment, the oligomeric alkylene glyol is end-capped with a methoxy, ethoxy, propyloxy, butoxy, pentoxy, or hexoxy group. The oligomeric alkylene glycol comprises from 2 to 13 alkylene glycol repeat units. Illustrative alkylene glycol repeat units include, for example, ethylene oxide ($-CH_2CH_2O-$)$_n$ and propylene oxide ($-CH_2CCHCH_3O-$)$_n$ repeat units, where n is selected from 2, 3, 4, 5, 6, 7, 8, 9, 10, 11, 12, and 13. A preferred oligomeric alkylene glycol contains ethylene oxide repeats. In one or more embodiments, the lower alkyl end-capped oligomeric alkylene glycol is diethylene glycol $HO-(CH_2CH_2O)_2-R$, where R is a lower alkyl group. Preferred lower alkyl end-capping groups, R are ethyl and methyl.

In some embodiments, a ternary solvent system comprises an aliphatic monohydric alcohol having between 1-6 carbon atoms and a non-end-capped oligomeric alkylene glycol (instead of a lower alkyl end-capped oligomeric alkylene glycol) in a w/w ratio of between about 0.8 and 2.6. Representative non-end capped oligomeric alkyene glycols include diols such as oligomeric PEG, and oligomeric polypropylene glycol. See, for example, formulation SS40-I or IG. As described above, an oligomeric alkylene glycol comprises from 2 to 13 alkylene glycol repeat units. Illustrative alkylene glycol repeat units include ethylene oxide ($-CH_2CH_2O-$)$_n$ and propylene oxide ($-CH_2CH_2CH_2O-$)$_n$ repeat units, where n is selected from 2, 3, 4, 5, 6, 7, 8, 9, 10, 11, 12, and 13. A preferred oligomeric alkylene glycol contains ethylene oxide repeats. In one or more embodiments, the non-end capped oligomeric alkylene glycol is oligomeric PEG. The oligomeric PEG typically possesses a number average molecular weight between about 300 and 600, or between about 300 and 500. A preferred oligomeric PEG is PEG-400, having a number average molecular weight of 400 ($M_n$ 380-420). While oligomeric PEGs having a small number of monomer repeats may be provided as monodisperse compounds, typically, oligomeric PEGs having 5 to 13 repeat units are provided as polydisperse compounds, where the molecular weight provided is a number average molecular weight unless otherwise indicated. Oligomeric PEGs, both end-capped and non-end capped are commercially available. Representative amounts of an end-capped oligomeric alkylene glycol as described herein apply equally to formulations in which the end-capped oligomeric alkylene glycol (e.g., DEGMEE) is replaced by a non-end capped oligomeric alkyelene glycol such as PEG.

The ternary solvent systems described above further comprise a fused bicyclic ether having from 8-14 carbon atoms, where the number of carbon atoms refers to the total number of carbon atoms including any substituents. Generally, the fused bicyclic ether contains from 1 to 3 oxygen atoms (e.g., 1, 2 or 3) in the bicyclic ring system (i.e., fused oxacycles). Illustrative fused bicyclic systems include bicyclo [3.3.0] and [4.3.0] systems. The fused bicyclic ether possesses no unsaturation (i.e., is saturated), and may comprise from 1 to 4 substituents covalently attached to the bicyclic ring system, where the substituents are moieties that only contain atoms selected from carbon, hydrogen and oxygen. Illustrative substituents include alkyl groups, lower alkoxy groups, and hydroxyl groups. Representative fused bicyclic ethers include dianhydro-D-glucucitol, isosorbide dimethyl ether (synonyms include dimethyl isosorbide and 1,4:3,6-dianhydro-2,5-di-O-methyl-D-glucitol), which possesses two methoxy groups substituted on the dianhydro-D-glucitol ring system, and isosorbide diethyl ether.

In one or more embodiments, the w/w ratio of the lower alkyl end-capped oligomeric alkylene glycol to the fused bicyclic ether having from 8-14 carbon atoms is in a range between about 1 and 2.4, or between about 1 and 2, or preferably between about 1.2 and 1.8, or in some instances, is about 1.7. Exemplary w/w ratios include 1.1, 1.2, 1.3, 1.4, 1.5, 1.6, 1.7, 1.8, 1.9, 2.0, 2.1, 2.2, and 2.3, including any and all ranges in between any two of the foregoing values.

In one or more embodiments, the composition comprises from about 70 w/w % to about 16 w/w % of an aliphatic monohydric primary alcohol, or from about 65 w/w % to about 18 w/w %, or preferably from about 60 w/w % to about 20 w/w % of an aliphatic monohydric primary alcohol. In the event that the composition additionally comprises a non-aliphatic monohydric primary alcohol such as benzyl alcohol, the total w/w percent of monohydric primary alcohol in the composition will increase accordingly. When present in the formulations, benzyl alcohol is typically present at a w/w percent that is less than ten percent. Thus, the above w/w percentages for total w/w percent monohydric primary alcohol will increase accordingly: 80 w/w % to about 26 w/w % of monohydric primary alcohol, or from about 75 w/w % to about 28 w/w %, or preferably from about 70 w/w % to about 30 w/w % monohydric primary alcohol. These representative w/w percentages are considered to be disclosed in combination with any of the other illustrative w/w percentages of additional composition components described herein and/or disclosed in combination with any one or more of the w/w percentages disclosed herein.

In one or more alternative embodiments, e.g., when the solvent system does not contain an N-substituted lactam, the composition comprises from about 70 w/w % to about 30 w/w % of an aliphatic monohydric primary alcohol, or from about 65 w/w % to about 35 w/w %, or preferably from about 60 w/w % to about 40 w/w % of an aliphatic monohydric primary alcohol. In the event that the composition additionally comprises a non-aliphatic monohydric primary alcohol such as benzyl alcohol, the total w/w percent of monohydric primary alcohol in the composition will increase accordingly. These representative w/w percentages are considered to be disclosed in combination with any of the other illustrative w/w percentages of additional composition components described herein and/or disclosed in combination with any one or more of the w/w percentages or ranges disclosed herein.

In one or more additional embodiments, the composition comprises from about 16 w/w % to about 35 w/w %, or from about 20 w/w % to about 30 w/w % of the lower alkyl end-capped oligomeric alkylene glycol. A representative about of the lower alkyl end-capped oligomeric alkylene glycol is about 25 w/w %. These representative w/w percentages are considered to be disclosed in combination with any of the other illustrative w/w percentages of additional composition components described herein and/or disclosed in combination with any one or more of the w/w percentages or ranges disclosed herein.

In one or more embodiments, the combined percent by weight of the lower alkyl end-capped oligomeric alkylene glycol and the fused bicyclic ether having from 8-14 carbon atoms is from 30-50 w/w %. In certain representative formulations, the combined percent by weight of the optionally lower alkyl end-capped oligomeric alkylene glycol and the fused bicyclic ether having from 8-14 carbon atoms is 40 w/w %.

In further exemplary embodiments, the topical formulation comprises from about 7 w/w % to about 25 w/w %, or from about 10 w/w % to about 20 w/w % of a fused bicyclic ether having from 8-14 carbon atoms. In one or more preferred embodiments, the w/w percent of the fused bicyclic ether having from 8-14 carbon atoms, e.g., dimethyl isosorbide, is less than the w/w percent of both the monohydric primary alcohol and the lower alkyl end-capped oligomeric alkylene glycol (e.g., DEGMEE). In one or more embodiments, the w/w percent of the fused bicyclic ether having from 8-14 carbon atoms is about 15 percent by weight.

In certain representative formulations, the ternary solvent system (i.e., composed of three solvents each present in greater than 10 percent by weight) as described above consists essentially of ethanol, diethylene glycol monoethyl ether, and dimethyl isosorbide. See, for example, compositions SS-37I (or IG, where G refers to gel) and SS-38I (or IG).

In an alternative illustrative formulation, the ternary solvent system (i.e., composed of three solvents each present in greater than 10 percent by weight) as described above consists essentially of ethanol, oligomeric polyethylene glycol, and dimethyl isosorbide. See, for example, composition SS-40I (or IG, where G refers to gel).

Generally, preferred compositions comprising itraconazole possesses a saturated solubility of itraconazole from about 0.14-1.5 w/w percent, or more preferably, from about 0.25-1.0 w/w percent.

One solvent suitable for enhancing the solubility of itraconazole in topical formulations is N-methyl-2-pyrrolidone ("N-methyl pyrrolidone or NMP"). As noted in Example 6, itraconazole possesses a saturated solubility in N-methyl pyrrolidone of 7.65% w/w. Thus, certain topical formulations of itraconazole comprise an N-substituted lactam having 5-ring atoms, 6-ring atoms or 7-ring atoms. In certain embodiments, the nitrogen atom of the lactam is substituted with a methyl or with an ethyl group (i.e., is an N-methyl or is an N-ethyl lactam). A preferred lactam is N-methyl pyrrolidone. See, e.g., formulation SS43-I or IG.

In certain formulations, the solvent system is a quaternary solvent system comprising four different solvents each present in the solvent system in a w/w percentage greater than 10 weight percent. Representative quaternary solvent systems include as one of the solvents an N-substituted lactam. Generally, such quaternary solvent systems include a monohydric primary alcohol, a lower alkyl end-capped oligomeric alkylene glycol, a fused bicyclic ether having from 8-14 carbon atoms, and an N-substituted lactam as previously described. In one or more embodiments of a quaternary solvent system, the w/w ratio of the monohydric primary alcohol and the lower alkyl end-capped oligomeric alkylene glycol is between about 0.6 and 1.5, or is between about 0.8 and 1.4, or is between about 0.9 and 1.3, or is between about 1.0 and 1.5. In yet one or more further embodiments, the percentage by weight of each of the monohydric primary alcohol, the lower alkyl end-capped oligomeric alkylene glycol, and N-vinyl pyrrolidone is from about 20-30. An exemplary quaternary solvent system consists essentially of ethanol, diethylene glycol monoethyl ether, dimethyl isosorbide, and N-methyl pyrrolidone. In one or more embodiments of a quaternary solvent system, the percent by weight of the fused bicyclic ether having from 8-14 carbon atoms is less than that of the monohydric primary alcohol, the lower alkyl end-capped oligomeric alkylene glycol, and the N-substituted lactam. Representative quaternary solvent systems comprise from about 11 w/w % to about 50 w/w %, or from about 15 w/w % to about 45 w/w %, or even from about 20 w/w % to about 35 w/w % of the N-substituted lactam. In a preferred formulation, the w/w percent of N-methyl pyrrolidone in the composition is about 25. As in all instances herein, the representative w/w percentages are considered to be disclosed in combination with any of the other illustrative w/w percentages of additional composition components described herein and/or disclosed in combination with any one or more of the w/w percentages or ranges disclosed herein. In one or more embodiments of a quaternary solvent system comprising an N-substituted lactam, the solvent system contains from about 40 w/w % to about 16 w/w % of an aliphatic monohydric primary alcohol, or from about 17 w/w % to about 35 w/w %, or preferably from about 18 w/w % to about 30 w/w % of an aliphatic monohydric primary alcohol.

An additional exemplary solvent system for topically administering a hedgehog inhibitor compound such as itraconazole comprises (i) a ternary combination of low molecular weight aliphatic polyols having molecular weights ranging from 50 to 550), where the polyols possess 2 or 3 hydroxyl groups, and a lower alkyl end-capped oligomeric alkylene glycol as described above in a w/w ratio of between about 1.5 and 2.4 and (ii) a fused bicyclic ether having from 8-14 carbon atoms (as described above). In certain embodiments of the foregoing, the solvent system is absent an aliphatic monohydric alcohol such as ethanol.

Suitable aliphatic diols and triols include, for example, propylene glycol, dipropylene glycol, hexylene glycol, 1,3-butylene glycol, liquid polyethylene glycols, such as polyethylene glycol200 (PEG-200) and polyethylene glycol400 (PEG-400), glycerol, trimethylolpropane, sorbitol and pentaerythritol. In one or more embodiments, the ternary combination contains two low molecular weight aliphatic polyols each containing 2-4 carbon atoms. In certain embodiments, the ternary combination contains two low molecular weight aliphatic polyols each containing three carbon atoms. In a particular embodiment, the ternary combination comprises HOCH$_2$C(OH)HR' where R' is —CH$_3$ or —CH$_2$OH. In certain embodiments, the ternary combination comprises glyercol and propylene glycol. In other embodiments, the ternary combination further comprises a polyethylene glycol, e.g., having a number average molecular weight from 300-500. In some embodiments, the w/w ratio of the ternary combination of aliphatic polyols to the lower alkyl end-capped oligomeric alkylene glycol is in a range from 1.8 to 2.1. For example, the ternary combination of aliphatic polyols is present in the composition at a combined w/w percent between about 35 and 60, or between about 40 and 55. In one or more further representative embodiments, w/w ratio of propylene glycol to glycerol is between 1.5 and 2.5, and the w/w ratio of polyethylene glycol to glycerol is between 1.5 and 2.5. A representative formulation is SS-50I or IG.

The instant formulations, and in particular, those particularly suited for administration of itraconazole, may, as described previously, further comprise benzyl alcohol. Benzyl alcohol, while not an aliphatic primary alcohol, is a primary alcohol. Thus, in one or more embodiments, the monohydric alcohol component comprises, in addition to an aliphatic monohydric primary alcohol, the primary alcohol benzyl alcohol. When present in the formulations, benzyl alcohol is typically present at a w/w percent that is less than ten percent. Illustrative amounts of benzyl alcohol include 1 w/w %, 2 w/w %, 3 w/w %, 4 w/w %, 5 w/w %, 6 w/w %, 7 w/w %, 8 w/w %, and 9 w/w %. An exemplary about of benzyl alcohol is 5 w/w percent. The addition of up to ten w/w percent benzyl alcohol can be effective in increasing the concentration of itraconazole in the formulations. In some embodiments, the formulation does not contain benzyl alcohol but does contain phenoxyethanol. In other embodiments, the formulation does contain benzyl alcohol but does not contain phenoxyethanol, a preservative. When contained in the instant formulations, the amount of phenoxyethanol is generally from about 0.01 w/w % to about 5 w/w %, or is from about 0.5 w/w % to about 3 w/w %, or is even present in an amount between about 0.07-2 wt %. Illustrative amounts of phenoxyethanol include the following percentages by weight: 0.1, 0.5, 1.0, 1.5, 2.0, 2.5 and 3.0.

A hedgehog inhibitor formulation, e.g., comprising itraconazole or patidegib, may additionally contain small amounts, e.g., less than about 10 w/w percent, of one or more additional additives, excipients, stabilizers, solvents, buffers, anti-oxidants, gel forming agents, preservatives, or the like. For example, in one or more embodiments, the composition comprises a small amount (e.g., 1, 2, 3, 4, 5, 6, 7, 8, or 9 w/w %) of an organic carbonate ester, preferably, a dialkyl carbonate ester. Preferred are cyclic carbonate esters having a ring size from 4 to 7 atoms. One exemplary cyclic carbonate ester is propylene carbonate. See, e.g., formulations SS38-I, SS40-I, SS43-I and SS50-I (or IG).

The instant formulations may also contain small amounts, e.g., from 0.01 to 5 w/w %, more typically from 0.01 to 0.5 w/w % of an anti-oxidant. Exemplary anti-oxidants include, for example, butylated hydroxyanisole (BHA), butylated hydroxytoluene (BHT), ascorbic acid, tert-butyl hydroquinone, propyl gallate, and the like. In one or more particular embodiments, a topical composition as described herein contains butylated hydroxytoluene.

The compositions described may be in the form of solutions, suspensions, emulsions, ointments, lotions, gels, and the like. Emulsions of the form oil-in-water or water-in-oil are contemplated, particular for non-itraconazole containing formulations. The compositions are topically applied directly to the skin, for example, with the fingertips of a subject in need or by a caregiver, or for example, by spraying the solution or suspension onto the skin.

Gels are formed by the entrapment of large amounts of aqueous or aqueous-alcoholic liquids in a network of colloidal solid particles. These colloids are typically present at concentrations of less than 10% w/w and are also referred to as gelling agents or thickening agents, also mentioned herein above. Examples of suitable gelling agents include carboxymethyl cellulose, hydroxypropylmethyl cellulose, hydroxyethyl cellulose, methyl cellulose, sodium alginate, alginic acid, pectin, tragacanth, carrageen, agar, clays, aluminium silicate, carbomers, etc.

For formulations comprising itraconazole, the gelling agent hydroxypropyl cellulose (HPC) is preferred, in particular for use in formulations in which a smooth, non-particulate containing formulation is desired. Illustrative amounts of a gelling agent, as mentioned above, are typically less than 10 w/w %, and are often less than 5 w/w %. For instance, a formulation as provided herein may comprise 1, 2, 3, 4, or 5 w/w percent of a gel forming agent. In some embodiments, the formulation comprises from 1-3 w/w % of a gel forming agent. In one or more embodiments, the hedgehog inhibitor is itraconazole and the thickening agent is hydroxypropyl cellulose; in another embodiment, the hedgehog inhibitor is itraconazole and the thickening/gelling agent is hydroxypropylcellulose having a weight average molecular weight between about 50,000 to 150,000 Daltons, or from about 60,000 to about 125,000 Daltons, or preferably from about 80,000 to about 100,000 Daltons.

Creams and ointments may also be utilized. They are emulsions of oleaginous substances and water (i.e. the carrier). The cream may be a water-in-oil (w/o) in which an aqueous phase is dispersed in an oil phase, or an oil-in-water (o/w) which have an oil dispersed within an aqueous base. An ointment is also contemplated, and is typically more viscous than an o/w cream. Traditional ointment bases (i.e. the carrier) include hydrocarbons (petrolatum, beeswax, etc.) vegetable oils, fatty alcohols (cholesterol, lanolin, wool alcohol, stearyl alcohol, etc.) or silicones. Pastes are a type of ointment into which a high percentage of insoluble particulate solids have been added, up to 50% by weight. Insoluble solids such as starch, zinc oxide, calcium carbonate, or talc may be used.

Aerosols may also be utilized. The compound may be dissolved in a propellant and a co-solvent such ethanol, acetone, hexadecyl alcohol, etc. Foaming agents may be incorporated to produce a mousse.

In some embodiments directed to topical formulations in which the hedgehog inhibitor compound is itraconazole, the composition does not contain a surfactant. In some other embodiments directed to topical formulations comprising the hedgehog inhibitor, itraconazole, the composition is absent a triglyceride. In yet some further embodiments related to topical formulations in which the hedgehog inhibitor compound is itraconazole, the composition is absent a complexing agent such as a cyclodextrin. In yet one or more further embodiments of a topical formulation comprising the hedgehog inhibitor, itraconazole, the composition is not an oil-in-water emulsion and does not contain a hydrophobic oil. In certain further embodiments, the itraconazole-containing composition does not contain a surfactant, or a triglyceride, or a complexing agent, or a hydrophobic oil.

Formulations having the characteristics described herein, e.g., the particular composition components and relative amounts and ranges of each, were devised based at least in part upon hedgehog inhibitor solubility, as well as system compatibility, and stability of the hedgehog inhibitor in the formulation over time. Following an investigation of short-term stability, as described in detail in Example 8, itraconazole-containing formulations having particular advantageous features were further examined for their in-vitro skin permeation. These exemplary topical formulations are described in tabular form below. The "IG-2" designation of the samples refers to an itraconazole-containing gel formulation containing 2 w/w % of a gel forming agent.

TABLE 5-1

Exemplary Topical Compositions

| | SS-37-IG2 wt % | SS-38 IG2 wt % | SS-40 IG2** wt % | SS-43 IG2 wt % | SS-50 IG2 wt % |
|---|---|---|---|---|---|
| ethanol | 56.80 | 47.65 | 47.65 | 22.20 | — |
| DEGEE | 25.00 | 25.00 | — | 25.00 | 25.00 |
| PEG-400 | — | — | 25.00 | — | — |
| N-methyl pyrrolidone | — | — | — | 25.00 | — |
| TERNARY COMBINATION Glycerol/propylene glycol/PEG-400 | — | — | — | — | 10.00/ 19.75/ 17.90 |
| dimethyl isosorbide | 15.00 | 15.00 | 15.00 | 15.00 | 15.00 |
| benzyl alcohol | — | 5.00 | 5.00 | 5.00 | 5.00 |
| phenoxyethanol | 1.00 | — | — | — | — |
| propylene carbonate | — | 5.00 | 5.00 | 5.00 | 5.00 |
| Butylated hydroxytoluene | 0.10 | 0.10 | 0.10 | 0.10 | 0.10 |
| hydroxypropyl cellulose | 2.0 | 2.0 | 2.0 | 2.0 | 2.0 |
| itraconazole | 0.10 | 0.25 | 0.25 | 0.70 | 0.25 |
| Ratio* monohydric alcohol/lower alkyl end capped oligomeric alkylene glycol | 2.27 | 2.11 | — | 1.09 | — |

*Includes ethanol and benzyl alcohol
**Ratio of monohydric alcohol/non-end capped oligomeric alkylene glycol = 2.11

Figure 4:
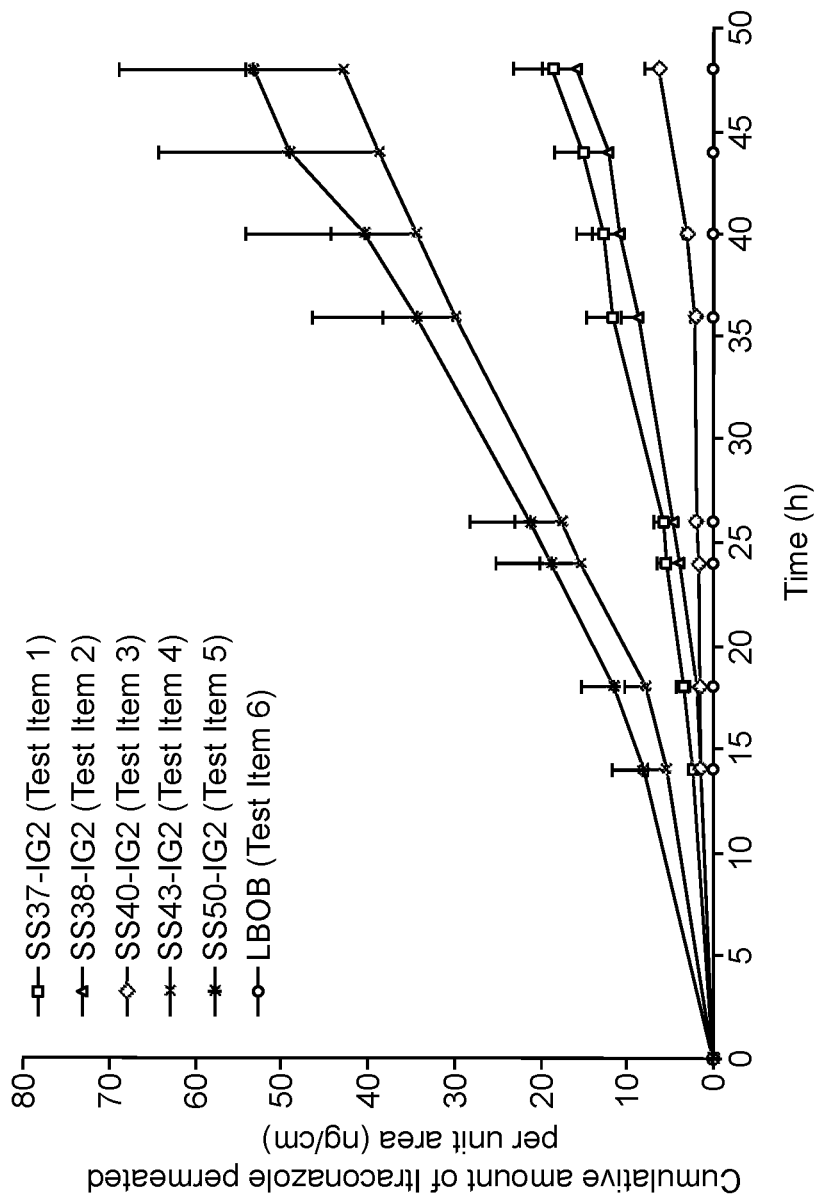
FIG. 4 is a graph demonstrating the cumulative amount of itraconazole permeated through human skin per unit area ($ng/cm^2$) over a 48 hour time period when evaluated at each of the following time points (hours): 0, 14, 18, 24, 26, 36, 40, 44 and 48 for representative topical formulations comprising itraconazole as described in Example 9.

FIG. 4 shows the cumulative amount of itraconazole permeated across human skin in vitro, in $ng/cm^2$, as a function of time, in hours, for the five compositions of itraconazole in the exemplary solvent systems set forth in Table 5-1. The formulations identified as SS50-IG2 (* symbols) and SS43-IG2 (x symbols) each provided a cumulative amount of itraconazole of at least about 40 $ng/cm^2$ in 48 hours. The formulation, SS50-G2, had the highest flux of the formulations tested and also achieved the highest cumulative amount of itraconazole delivered across the skin in 48 hours. Formulation SS43-IG2 exhibited the next highest flux and a similarly achieved the second highest cumulative amount of itraconazole delivered across the skin in 48 hours. Two of the formulations, SS37-IG2 (closed squares) and SS38-IG2 (closed triangles), achieved a cumulative amount of itraconazole of at least about 10 $ng/cm^2$ in 48 hours. The formulation identified as SS4-IG2 (closed diamonds) achieved a cumulative amount of itrazonazole of at least about 3 $ng/cm^2$ in 48 hours. Thus, the instant topical formulations are capable of permeating through human skin and also of achieving concentrations of itraconazole in the skin effective to achieve a cellular response.

Figure 5:
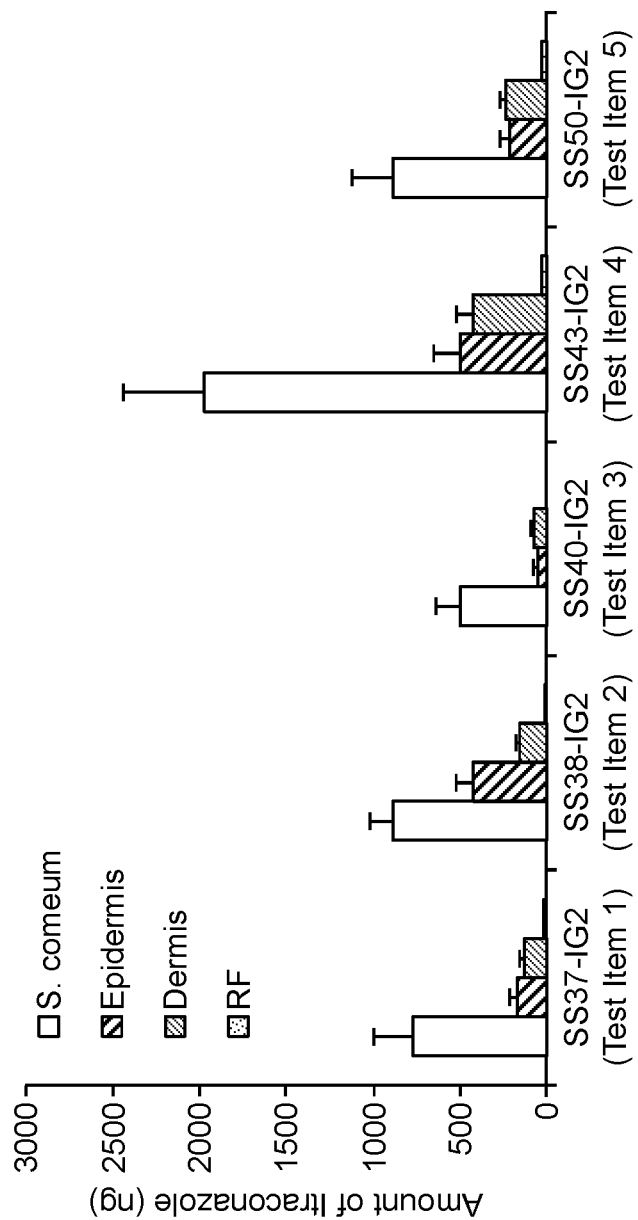
FIG. 5 is a bar graph illustrating the amount of itraconazole recovered (in ng) from each skin layer after the final 48 hour time point for each of the representative formulations evaluated following a permeation/penetration experiment as described in detail in Example 9. For each test item (itraconazole formulation), data is provided from left to right along the horizontal axis for the *stratum corneum*, epidermis, dermis, and receiver fluid.

To further assess the ability of the formulations to achieve intracutaneous delivery, the concentration of hedgehog inhibitor compound (itraconazole) in the *stratum corneum*, epidermis and dermis was measured after 48 hours topical exposure to the test formulations each comprising itraconazole. Results of the analysis of the layers of the skin for concentration of itraconazole are shown in FIG. 5. The amount of itraconazole delivered to the stratum corneum was highest for the formulation identified as SS43-IG2, which provided nearly 2000 ng (actual value 1973.01 ng) to the stratum corneum after 48 hours of topical application.

The same formulation, SS43-IG2, also delivered the highest amount of itraconazole to both the epidermis (about 500 ng; actual value 503.54 ng) and the dermis (greater than 400 ng; actual value 427.93 ng) after 48 hours of topical application. The formulations identified as SS50-IG2 and SS38-IG2 also delivered beneficial levels of itraconazole to each of the *stratum corneum*, the epidermis and the dermis.

The formulation identified as SS50-IG2 delivered about 900 ng (actual value 898.47 ng) of itrazonazole to the *stratum corneum*, about 210 ng (actual value 209.29 ng) to the epidermis, and about 230 ng (actual value 228.81 ng) to the dermis after 48 hours of contact with the skin.

The formulation identified as SS38-IG2 delivered about 900 ng (actual value 883.33 ng) of itraconazole to the *stratum corneum*, about 425 ng (actual value 426.71 ng) to the epidermis, and about 150 ng (146.91 ng) to the dermis after 48 hours of contact with the skin.

The topical formulations described herein are effective to provide an absolute concentration of hedgehog inhibitor compound such as patidegib or itraconazole in the living skin (epidermis and dermis) that is sufficient to have a molecular effect, i.e., suppress hedgehog signaling.

Accordingly, in one embodiment, a topical formulation of itraconazole is provided that achieves after 48 hours of topical application in vitro an amount of itraconazole in the epidermis, the dermis, or the epidermis and dermis combined that exceeds by at least about 150%, 200%, 300%, 350% or 400% the amount of itraconazole in the receiver fluid. In another embodiment, a topical formulation of itraconazole is provided that achieves after 48 hours of topical application in vitro an amount of itraconazole in the epidermis, the dermis, or the epidermis and dermis combined that is at least about 1.5, 2, 3, 3.5, 4 or 5 fold greater than the amount of itraconazole in the receiver fluid. As supported by the concentration values of itraconazole in each of the skin matrices for representative topical compositions of itraconazole in Table 9, the formulations described herein are effective to achieve therapeutically effective levels of itraconazole in the skin, since the concentrations of itraconazole achieved in each of the skin layers notably exceeds the IC50 value for itraconazole (0.8 µM, Kim and Beachy, *Cancer Cell*, 17, 388-399, 2010).

A wide variety of methods may be used for preparing the formulations described above. Broadly speaking, the formulations may be prepared by combining together the components of the formulations, as described herein, at a temperature and for a time sufficient to provide a pharmaceutically effective and elegant composition. The term "combining together", as used herein, means that all of the components of the compositions may be combined and mixed together at about the same time. The term "combining together" also means that the various components may be combined in one or more sequences to provide the desired product. The formulation can be prepared on a weight/weight (w/w) or a weight/volume (w/v) basis depending upon the form of the final dosage form.

The compositions may be packaged for use in a medical setting or for retail distribution directly to the consumer (i.e., an article of manufacture or kit). Such articles will be labeled and packaged in a manner advising the patient how to use the product for therapy. Such instructions will include the duration of treatment, dosing schedule, precautions, etc. These instructions may be in the form of pictures, written instructions, or a combination thereof. They may be printed on the side of the packaging, be an insert, or any other form of communication appropriate for the retail market.

It will be appreciated that, in other embodiments, the compositions can be incorporated into a topical delivery system that is applied to the skin. Topical delivery systems are well described in the literature and can take the form of a reservoir type system with a backing member secured to a membrane to device a reservoir for the composition. An adhesive is included about the periphery of the membrane to secure the system to the skin. Other examples of delivery systems that may be used for topical application of the formulations described herein are summarized, for example, in R. W. Baker and J. Farrant "Patents in transdermal drug delivery", *Drug Delivery Systems* 1987 Conference Proceedings, and the patents noted therein describing delivery devices are incorporated by reference herein.

C. Methods of Treating

The compositions described herein are, in one aspect, for treating a hedgehog-associated cancer or tumor. The tumor can be a solid tumor, a soft tissue tumor, or a metastatic lesion. In one embodiment, the compositions are for the treatment of skin cancer or more specifically of squamous cell carcinoma, keratoacanthoma, melanoma, or basal cell carcinoma. In one embodiment, the skin cancer is basal cell carcinoma. In yet a further embodiment, a method of treating a subject with Gorlin syndrome is provided, where the subject presents with or is at risk of presenting with basal cell carcinoma.

For treatment of a skin cancer, the composition is applied topically to the subject. In one embodiment, the topical application is to the region of the skin presenting with a cancerous lesion, and in other embodiments, the topical application is to a region of the skin that is not presenting with a cancerous lesion—e.g., the composition is applied topically to healthy skin for prevention. In one particular embodiment, the composition is applied directly to the cancerous lesion.

For illustrative itraconazole based formulations, e.g., containing from about 0.1 to about 2 w/w % itraconazole, a single dose full face application will typically correspond to about 0.1 mg to about 2 mg of itraconazole, assuming application of approximately 125 milligrams of gel to the face.

The composition is applied to the skin, in various embodiments, once a month, once every two weeks, once every 10 days, once a week, twice a week, three times a week, every other day, once daily, twice daily, three times daily or four times daily, etc. The dosing schedule will depend, as can be appreciated, by factors well known in medical arts, including the dose of drug compound in the composition, the particular hedgehog inhibitor compound, additional therapeutic agents, if present, the type of cancer or condition to be treated, and the health of the patient.

The methods and compositions can optionally be used in combination with one or more other cancer therapies (e.g., one or more therapeutic agents, surgery and/or radiation). In one or more embodiments, the methods and compositions are used in combination with a surgical procedure and/or radiation therapy. Surgical procedures include, but are not limited to, excision, curettage and electrosurgery, cryosurgery, Mohs micrographic surgery, and laser surgery. Excision is useful for both primary and recurrent tumors and has the advantage of allowing for histological assessment of surgical margins. Curettage and electrosurgery involves alternately removing soft tumor tissue with a curette and then destroying an extra margin of tissue by electrodesiccation, electrocautery, or electrocoagulation. Cryosurgery involves freezing the tumor to a temperature that kills the cells of the tumor. The dead tumor cells can be removed by, for example, curettage. Mohs micrographic surgery (MMS) involves a surgeon using a microscope to identify the margin of the tumor more accurately and more precisely than is possible by unaided visual inspection. MMS can increase the likelihood that the entire tumor is removed and minimize the amount of normal tissue that is removed. Laser surgery involves using a laser to vaporize tumor cells or use of a laser in lieu of a scalpel blade for excisional surgery.

In other embodiments, the methods and compositions provided herein are used in combination with one or more therapeutic agents. Any combination of the hedgehog inhibitor composition and other cancer therapies (e.g., one or more additional therapeutic agents, surgery and/or radiation) can be used. For example, a topical hedgehog inhibitor composition as described herein may comprise one or more additional therapeutic agents, or may be administered in conjunction with another type of therapy or treatment. Additionally, the hedgehog inhibitor composition and/or other cancer therapies can be administered or carried out during periods of active disorder, or during a period of remission or less active disease. The hedgehog inhibitor composition and other cancer therapies as applicable can be administered before treatment, concurrently with treatment, post-treatment, or during remission of the disorder or condition being treated. In one embodiment, the method or composition comprises a combination of patidegib and itraconazole.

In a further aspect, topically formulated itraconazole may be administered in conjunction with another topical drug such as but not limited to patidegib, to thereby prevent or inhibit degradation of the topical drug (e.g., patidegib), e.g., by cytochrome-based degradation mechanisms, in the skin. By reducing its metabolism in the living skin, one may be able to provide a lower dose of patidegib (or another topical agent) than could otherwise be achieved (e.g., in the absence of a combination with itraconazole) to achieve a therapeutically effective concentration of drug in the skin. In one or more further related embodiments, topical patidegib, e.g., comprised within a composition or delivery system as provided herein, is administered in conjunction with another topical azole drug such as fluconazole, or ketoconazole, to thereby prevent or lessen degradation of the patidegib, e.g., by cytochrome-based degradation mechanisms, in the skin. The topical administration of an azole drug such as itraconazole may therefore be effective to improve the efficacy of a topical or even systemically administered drug such as patidegib due to local inhibition of degradation mechanisms that function to metabolize the drug in the skin.

A study was conducted to evaluate the toxicokinetics of patidegib when administered twice daily via dermal application for 13 weeks. As described in Example 11, the formulation identified herein as SS14 was prepared, with patidegib concentrations of 2% and 4%. The formulations, along with a placebo, were applied topically to Gottingen Minipigs® twice daily, and blood samples were collected on study days 1, 14 and 90 for analysis of patidegib and its metabolite, IPI-230.

Figure 6A:
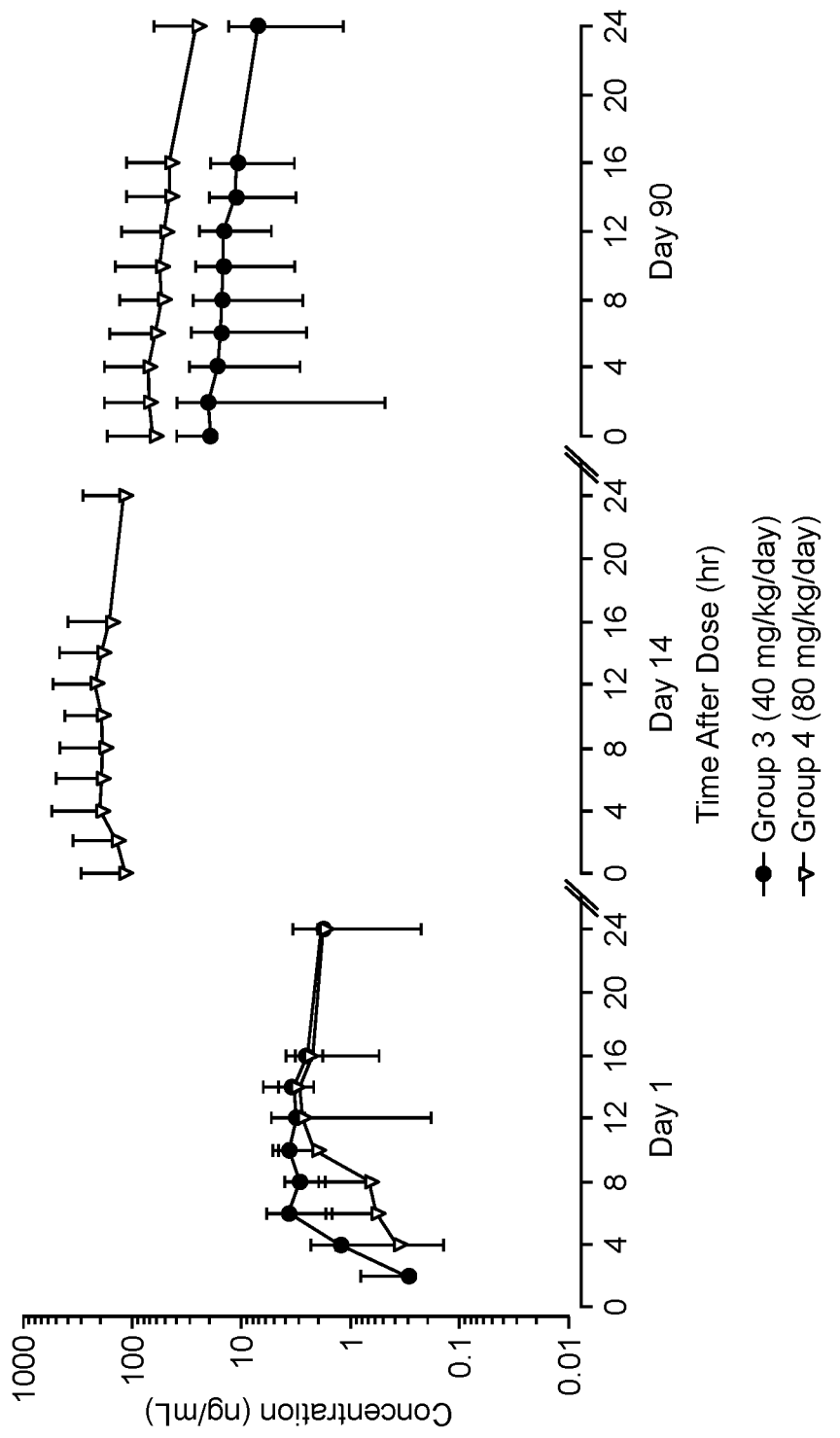
FIGS. 6A-6B are mean concentration-time profiles of patidegib (FIG. 6A) and its metabolite, IPI-230 (FIG. 6B) in Gottingen Minipig® plasma for the test groups (male and female results combined) treated with 40 mg/kg/day (closed circles) and 80 mg/kg/day (inverted diamonds) patidegib topically.
Figure 6B:
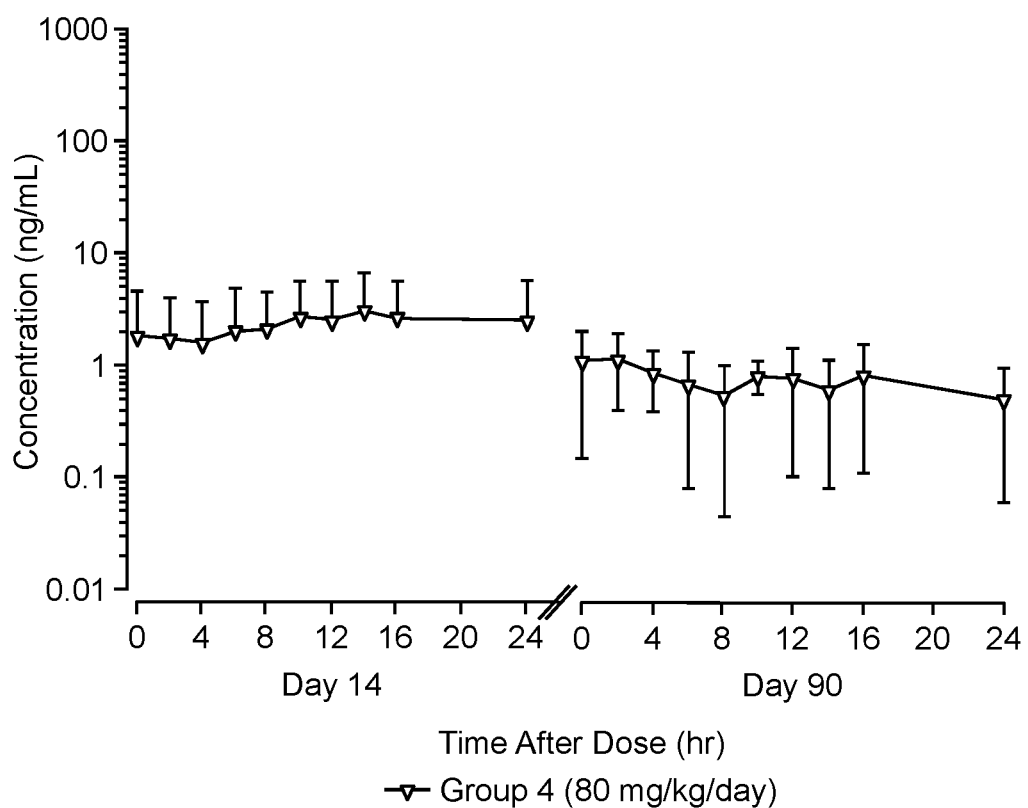
Figure 7A:
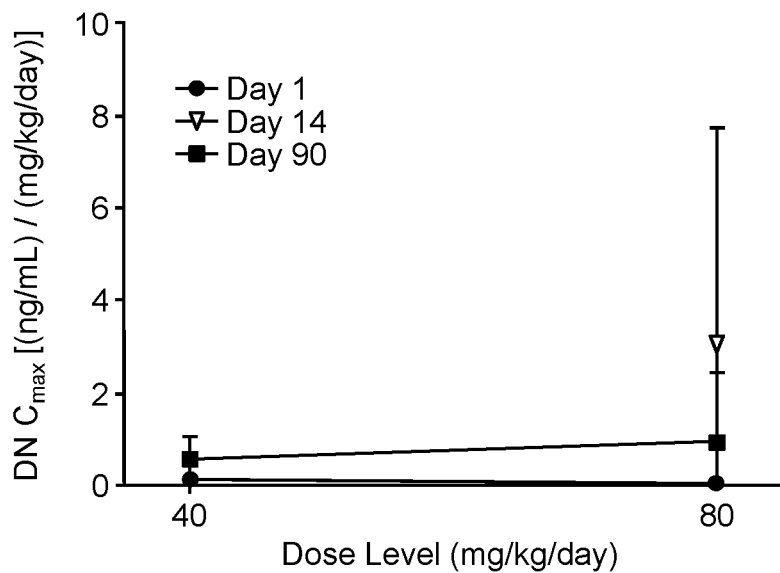
FIGS. 7A-7B are dose normalized $C_{max}$ and $AUC_{0-24}$ relationships, respectively, of patidegib in Gottingen Minipig® plasma for the test groups (male and female results combined) treated with 40 mg/kg/day and 80 mg/kg/day patidegib topically, on Day 1 (closed circles), Day 14 (inverted triangles) and Day 90 (closed squares) of the study (Example 11).
Figure 7B:
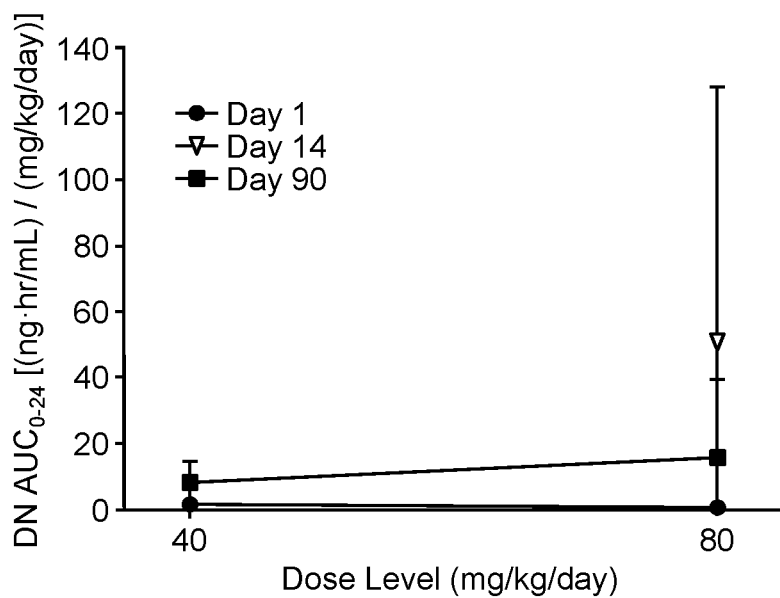

The mean concentration-time profiles of patidegib in plasma for the test groups (male and female results combined) are presented graphically in FIG. 6A and the mean concentration-time profiles of IPI-230 in plasma for the test groups (male and female results combined) are presented graphically in FIG. 6B. The dose normalized $C_{max}$ and $AUC_{0-24}$ relationships of patidegib in Gottingen Minipig® plasma are presented graphically in for the combined sexes in FIGS. 7A-7B. After dermal administration, patidegib was absorbed. Individual $T_{max}$ values were observed 2 to 8 hours post the first or second dose on Day 1, and 2 to 6 hours post the first or second dose on Days 14 and 90. The mean concentration-time profiles for the combined sexes (FIG. 6A) show that exposure to patidegib generally increased with the increase in dose level from 40 to 80 mg/kg/day on Day 90. The data also shows that after dermal administration of patidegib, IPI-230 appeared in plasma (FIG. 6B). Individual $T_{max}$ were observed 2 to 8 hours post the first or second daily dose on Days 14 and 90. The exposure, as assessed by patidegib mean $C_{max}$ and $AUC_{0-24}$ values, increased with the increase in patidegib dose level from 40 to 80 mg/kg/day on Day 90. The increases in patidegib mean $C_{max}$ and $AUC_{0-24}$ values were generally dose proportional, as presented FIGS. 7A-7B.

Exposure to patidegib increased with the increase in dose level from 40 to 80 mg/kg/day on Day 90. The increases in patidegib mean $C_{max}$ and $AUC_{0-24}$ values on Day 90 were generally greater than dose proportional. Patidegib mean $C_{max}$ and $AUC_{0-24}$ values were generally greater than 4-fold higher in females, when compared to males, on Days 14 and 90. Patidegib Day 14 to Day 1 ratio values ranged from 45.8 to 139 and from 70.7 to 218 for mean $C_{max}$ and $AUC_{0-24}$, respectively. Patidegib Day 90 to Day 1 ratio values ranged from 7.89 to 28.4 and from 9.18 to 39.9 for mean $C_{max}$ and $AUC_{0-24}$, respectively. Additionally, mean $C_{max}$ and $AUC_{0-24}$ were generally lower on Day 90 when compared to Day 14.

Exposure to the patidegib metabolite IPI-230 was demonstrated following twice daily administration of patidegib at 80 mg/kg/day on Days 14 and 90. IPI-230 mean $C_{max}$ and $AUC_{0-24}$ values were greater than 2-fold in females when compared to males. Mean $C_{max}$ and $AUC_{0-24}$ values could not be compared to Day 1, as Day 1 values for IPI-230 were generally below the limit of quantification (BLQ). The mean metabolite to parent ratios ranged from 0.00535 to 0.00738 and from 0.00524 to 0.00702, for $C_{max}$ and $AUC_{0-24}$, respectively. In summary, the study in Example 11 demonstrated that exposure to patidegib increased with the increase in dose level from 40 to 80 mg/kg/day on Day 90. Exposure to IPI-230 was demonstrated following twice daily administration of Patidegib at 80 mg/kg/day on Days 14 and 90. The study also demonstrated that the increases in patidegib mean $C_{max}$ and $AUC_{0-24}$ values on Day 90 were generally dose proportional. Patidegib and IPI-230 mean $C_{max}$ and $AUC_{0-24}$ values were generally greater than 2-fold higher in females when compared to males. Patidegib Day 14 to Day 1 ratio values ranged from 45.8 to 139 and from 70.7 to 218 for mean $C_{max}$ and $AUC_{0-24}$, respectively. Patidegib Day 90 to Day 1 ratio values ranged from 7.89 to 28.4 and from 9.18 to 39.9 for mean $C_{max}$ and $AUC_{0-24}$, respectively. IPI-230 Day 14 and Day 90 mean $C_{max}$ and $AUC_{0-24}$ values could not be compared to Day 1, as Day 1 values for IPI-230 were generally BLQ. The mean metabolite to parent ratios ranged from 0.00535 to 0.00738 and from 0.00524 to 0.00702, for $C_{max}$ and $AUC_{0-24}$, respectively.

III. Examples

The following examples are illustrative in nature and are in no way intended to be limiting.

Example 1

Topical Formulations

The hedgehog inhibitor compound patidegib and the following solvent systems were prepared as topical formulations.

TABLE 1-1

Topical Formulation SS5

| Component | w/w % | Ratio EtOH + BnOH/PG | Ratio Ethanol/PG |
|---|---|---|---|
| ethanol | 18.73 | 1.1 | 1.0 |
| propylene glycol | 18.73 | | |
| benzyl alcohol | 1.87 | | |
| diethylene glycol monoethyl ether* | 18.73 | | |
| buffer, pH 7.5 | 35.59 | | |
| hydroxypropyl cellulose (HPC; Klucel HF grade) | 2.00 | | |
| patidegib | 4.35 | | |

*abbreviated herein as "DEGEE" and also known as 2-(2-ethoxyethoxy) ethanol and sold under the tradename Transcutol ® P

TABLE 1-2

Topical Formulation SS6

| Component | w/w % | Ratio EtOH + BnOH/PG | Ratio Ethanol/PG |
|---|---|---|---|
| ethanol | 27.54 | 1.60 | 1.5 |
| propylene glycol | 18.36 | | |
| benzyl alcohol | 1.84 | | |
| diethylene glycol monoethyl ether | 18.36 | | |
| buffer, pH 7.5 | 25.70 | | |
| hydroxypropyl cellulose | 2.00 | | |
| patidegib | 6.21 | | |

TABLE 1-3

Topical Formulation SS14

| Component | w/w % | Ratio Ethanol/PG |
|---|---|---|
| ethanol | 23.49 | 1.25 |
| propylene glycol | 18.79 | |
| diethylene glycol monoethyl ether | 18.79 | |
| buffer, pH 7.5 | 31.01 | |
| phenoxyethanol | 0.94 | |
| hydroxypropyl cellulose | 2.00 | |
| patidegib | 4.97 | |

TABLE 1-4

Topical Formulation SS20

| Component | w/w % | Ratio EtOH + BnOH/PG | Ratio Ethanol/PG |
|---|---|---|---|
| ethanol | 23.81 | 1.35 | 1.25 |
| propylene glycol | 19.05 | | |
| benzyl alcohol | 1.90 | | |
| buffer, pH 7.5 | 49.52 | | |
| hydroxypropyl cellulose | 2.00 | | |
| patidegib | 3.73 | | |

TABLE 1-5

Topical Formulation SS22

| Component | w/w % | Ratio EtOH+ BnOH/PG | Ratio Ethanol/PG |
|---|---|---|---|
| ethanol | 47.30 | 1.62 | 1.56 |
| propylene glycol | 30.27 | | |
| benzyl alcohol | 1.89 | | |

TABLE 1-5-continued

Topical Formulation SS22

| Component | w/w % | Ratio EtOH+ BnOH/PG | Ratio Ethanol/PG |
|---|---|---|---|
| isostearic acid | 14.19 | | |
| hydroxypropyl cellulose | 2.00 | | |
| patidegib | 4.35 | | |

The permeation of patidegib into human skin from the five formulations was tested in vitro using Franz diffusion cells. Franz diffusion cells with a surface area of about 0.6 cm$^2$ and a volume of 2.0 mL were used. Skin from an abdominoplasty was dermatomed to approximately 400 micrometers (μm). The receiver side of the cell was filled with ethanol/water 20/80 and the cells were maintained at 37±0.5° C. Each test formulation was dosed into the sample side of the cells using a 1 mL plunger and positive displacement pipette. The weight of the plunger was determined before and after dispensing formulation into each cell to dispense a 6-7 mg dose of formulation (approximately 10 mg/cm$^2$). Each formulation was tested in six diffusion cells (n=6). A 200 μL aliquot of receiver fluid was removed from each cell at 0 hours, 14 hours, 18 hours, 24 hours, 36 hours, 40 hours, 44 hours and 48 hours. Following the 48 hour time point, the Franz cells were dismantled to recover the skin for analysis. The concentration of patidegib in the *stratum corneum*, epidermis and dermis was determined using tissue homogenization and solvent extraction (80/20 v/v ethanol/water) and analysis via LC MS/MS. Results are shown in FIGS. 1A-1B.

Example 2

Topical Formulations

The hedgehog inhibitor compound patidegib and the following solvent systems were prepared as topical formulations.

TABLE 2-1

Topical Formulation SS14.10

| Component | w/w % | Ratio Ethanol/PG |
|---|---|---|
| ethanol | 7.37 | 1.50 |
| propylene glycol | 4.91 | |
| diethylene glycol monoethyl ether (DEGEE) | 9.83 | |
| phenoxyethanol | 0.98 | |
| deionized water | 74.16 | |
| hydroxypropyl cellulose | 2.00 | |
| patidegib | 0.75 | |

TABLE 2-2

Topical Formulation SS14.19

| Component | w/w % |
|---|---|
| phenoxyethanol | 0.99 |
| deionized water | 96.91 |
| hydroxypropyl cellulose | 2.00 |
| patidegib | 0.10 |

TABLE 2-3

Topical Formulation SS22.7

| Component | w/w % | Ratio Ethanol/PG |
|---|---|---|
| isopropyl alcohol | 49.13 | 1.56 |
| propylene glycol | 31.44 | |
| isostearic acid | 16.68 | |
| hydroxypropyl cellulose | 2.00 | |
| patidegib | 0.75 | |

TABLE 2-4

Topical Formulation SS22.9

| Component | w/w % | Ratio Ethanol/PG |
|---|---|---|
| isopropyl alcohol | 49.45 | 0 |
| propylene glycol | — | |
| isostearic acid | 24.72 | |
| isopropyl myristate | 23.74 | |
| hydroxypropyl cellulose | 2.00 | |
| patidegib | 0.10 | |

The permeation of patidegib into human skin from the formulations identified in Example 1 as SS14 and SS22 and the formulations identified above as SS14.10, SS14.19, SS22.7 and SS22.9 were tested in vitro using Franz diffusion cells. Franz diffusion cells with a surface area of about 0.6 cm$^2$ and a volume of 2.0 mL were used. Skin from an abdominoplasty was dermatomed to approximately 400 micrometers (m). The receiver side of the cell was filled with ethanol/water 20/80 and the cells were maintained at 37±0.5° C. Each test formulation was dosed into the sample side of the cells using a 1 mL plunger and positive displacement pipette. The weight of the plunger was determined before and after dispensing formulation into each cell to dispense a 6-7 mg dose of formulation (approximately 10 mg/cm$^2$). Each formulation was tested in six diffusion cells (n=6). A 200 μL aliquot of receiver fluid was removed from each cell at 0 hours, 14 hours, 18 hours, 24 hours, 36 hours, 40 hours, 44 hours and 48 hours. Following the 48 hour time point, the Franz cells were dismantled to recover the skin for analysis. The concentration of patidegib in the *stratum corneum*, epidermis and dermis was determined using tissue homogenization and solvent extraction (80/20 v/v ethanol/water). Results are shown in FIGS. 2A-2B.

Example 3

Topical Formulations with Patidegib

The hedgehog inhibitor compound patidegib and the following solvent systems were prepared as topical formulations.

TABLE 3-1

Topical Compositions

| | Aqueous Formulations | | | Non-aqueous Formulations | | |
|---|---|---|---|---|---|---|
| | SS14 wt % | SS14D1 wt % | SS14D2 wt % | SS22 wt % | SS22D1 wt % | SS22D2 wt % |
| ethanol | 23.5 | 23.5 | 23.5 | 47.3 | 47.3 | 47.3 |
| propylene glycol | 18.8 | 18.8 | 18.8 | 30.3 | 30.3 | 30.3 |

TABLE 3-1-continued

Topical Compositions

| | Aqueous Formulations | | | Non-aqueous Formulations | | |
|---|---|---|---|---|---|---|
| | SS14 wt % | SS14D1 wt % | SS14D2 wt % | SS22 wt % | SS22D1 wt % | SS22D2 wt % |
| benzyl alcohol | — | — | — | 1.9 | 1.9 | 1.9 |
| DEGEE* | 18.8 | 18.8 | 18.8 | — | — | — |
| isostearic acid | — | — | — | 14.2 | 18.4 | 17.8 |
| phenoxyethanol | 0.9 | 0.9 | 0.9 | — | — | — |
| buffer | 31.0 | 35.9 | 35.2 | — | — | — |
| hydroxypropyl cellulose | 2.0 | 2.0 | 2.0 | 2.0 | 2.0 | 2.0 |
| patidegib | 5.0 | 0.1 | 0.75 | 4.4 | 0.1 | 0.75 |
| Ratio monohydric alcohol/diol | 1.25 | 1.25 | 1.25 | 1.62 | 1.62 | 1.62 |

*DEGEE = diethylene glycol monoethyl ether (Transcutol ® P)

The permeation of patidegib into human skin from the formulations was tested in vitro using Franz diffusion cells. Franz diffusion cells with a surface area of about 0.6 cm² and a volume of 2.0 mL were used. Skin from an abdominoplasty was dermatomed to approximately 400 micrometers (μm). The receiver side of the cell was filled with ethanol/water 20/80 and the cells were maintained at 37±0.5° C. Each test formulation was dosed into the sample side of the cells using a 1 mL plunger and positive displacement pipette. The weight of the plunger was determined before and after dispensing formulation into each cell to dispense a 6-7 mg dose of formulation (approximately 10 mg/cm²). Each formulation was tested in six diffusion cells (n=6). A 200 μL aliquot of receiver fluid was removed from each cell at 0 hours, 14 hours, 18 hours, 24 hours, 36 hours, 40 hours, 44 hours and 48 hours. Following the 48 hour time point, the Franz cells were dismantled to recover the skin for analysis. The concentration of patidegib in the *stratum corneum*, epidermis and dermis was determined using tissue homogenization and solvent extraction (80/20 v/v ethanol/water). Results are shown in FIGS. 3A-3B.

Example 4

Stability of Exemplary Patidegib Topical Formulations

Stability of the exemplary formulations (SS5, SS6, SS14, SS20 and SS22) was assessed by analyzing the formulations for patidegib content after four weeks storage at 25° C. and at 40° C. Results are shown in the tables below.

TABLE 4-1

Stability of Exemplary Formulations—Mean Percentage Recovery of Patidegib

| | | | Mean percentage recovery of patidegib from theoretical (n = 3, lowest-highest value) | | | |
|---|---|---|---|---|---|---|
| | patidegib | | t = 22 weeks | | t = 4 weeks | |
| Formulation | (% w/w) | t = 0 | 25° C. | 40° C. | 25° C. | 40° C. |
| SS5 (Aq.) | 4.35 | 97.88 (95.44- 100.31) | 109.82 (105.24- 113.56) | 106.51 (106.25- 106.64) | 97.61 (97.40- 97.88) | 96.24 (95.59- 97.06) |
| SS6 (Aq.) | 6.21 | 98.75 (97.24- 100.28) | 110.90 (109.77- 111.51) | 111.99 (109.75- 114.30) | 100.60 (99.11- 102.79) | 97.75 (97.28- 98.30) |

TABLE 4-1-continued

Stability of Exemplary Formulations—Mean Percentage Recovery of Patidegib

| | | | Mean percentage recovery of patidegib from theoretical (n = 3, lowest-highest value) | | | |
|---|---|---|---|---|---|---|
| | patidegib | | t = 22 weeks | | t = 4 weeks | |
| Formulation | (% w/w) | t = 0 | 25° C. | 40° C. | 25° C. | 40° C. |
| SS14 (Aq.) | 4.97 | 102.44 (101.61- 103.61) | 131.46 (127.08- 134.03) | 105.62 (105.19- 106.25) | 99.07 (98.39- 99.51) | 96.63 (95.93- 97.85) |
| SS20 (Aq.) | 3.73 | 107.89 (107.11- 108.30) | 65.38 (63.42- 67.35) | 104.49 (103.57- 105.46) | 102.05 (100.38- 103.72) | 97.71 (97.10- 98.24) |
| SS22 (Non-Aq.) | 4.35 | 114.96 (114.48- 115.40) | 100.24 (99.66- 101.34) | 93.98 (88.29- 103.31) | 100.25 (100.18- 100.29) | 99.57 (98.89- 99.93) |

TABLE 4-2

Stability of Exemplary Formulations—Peak Purity of Patidegib

| | | | Mean percentage area/area of patidegib (n = 3, lowest-highest value) | | | |
|---|---|---|---|---|---|---|
| | patidegib | | t = 2 weeks | | t = 4 weeks | |
| Formulation | (% w/w) | t = 0 | 25° C. | 40° C. | 25° C. | 40° C. |
| SS5 (Aq.) | 4.35 | 99.49 (98.78- 99.87) | 99.63 (99.60- 99.66) | 99.52 (99.47- 99.60) | 99.28 (99.26- 99.30) | 99.30 (99.23- 99.38) |
| SS6 (Aq.) | 6.21 | 100.00 (100.00- 100.00) | 99.71 (99.68- 99.77) | 99.41 (99.31- 99.48) | 99.08 (99.00- 99.15) | 99.25 (99.20- 99.28) |
| SS14 (Aq.) | 4.97 | 100.00 (100.00- 100.00) | 99.67 (99.65- 99.69) | 99.49 (99.35- 99.67) | 99.33 (99.32- 99.33) | 99.28 (99.26- 99.31) |
| SS20 (Aq.) | 3.73 | 99.89 (99.88- 99.90) | 99.67 (99.67- 99.67) | 99.46 (99.33- 99.61) | 99.31 (99.28- 99.34) | 99.27 (99.23- 99.31) |
| SS22 (Non-Aq.) | 4.35 | 100.00 (100.00- 100.00) | 99.94 (99.92 - 99.95) | 99.95 (99.92- 99.98) | 99.92 (99.91- 99.93) | 99.84 (99.83- 99.87) |

TABLE 4-3

Stability of Exemplary Formulations SS14 and SS22—Peak Purity of Patidegib

| | Storage | Percentage patidegib peak purity (%) | | |
|---|---|---|---|---|
| Formulation | condition (° C.) | T = 0 | T = 4 week | T = 8 week |
| SS14 | 25 | 99.72 | 99.82 | 99.89 |
| | 40 | | 99.88 | 99.87 |
| SS22 | 25 | 99.65 | 99.88 | 99.10 |
| | 40 | | 99.82 | 99.54 |

TABLE 4-4

Stability of Exemplary Formulations SS14 and SS22—Mean Percentage Recovery of Patidegib

| Formulation | Storage condition (° C.) | T = 0* | T = 2 week | T = 4 week | T = 8 week |
|---|---|---|---|---|---|
| SS14 | 25 | 100.61 (99.81-101.30) | 109.04 (106.62-111.51) | 103.44 (102.99-103.85) | 102.45 (102.38-102.56) |
|  | 40 |  | 103.42 (102.23-104.59) | 103.10 (102.91-103.20) | 103.17 (102.13-104.40) |
| SS22 | 25 | 95.78 (94.02-99.09) | 98.51 (98.13-99.19) | 99.90 (99.48-100.19) | 97.74 (97.46-98.03) |
|  | 40 |  | 104.24 (102.30-106.85) | 98.64 (98.17-98.89) | 98.92 (98.51-99.28) |

The patidegib content for all formulations at t=0 was between 97-117% of the theoretical concentration. The peak purity of the patidegib formulation at t=0 was greater than 99%. After 2 weeks of storage at 25° C. and at 40° C., the peak purity of all formulations were comparable to the starting peak purity at t=0 and observed to be greater than 99%. The patidegib content for the formulations 2 weeks of storage at 25° C. and at 40° C. was between 65-131% of the theoretical concentration. After 4 weeks of storage at 25° C. and at 40° C. the patidegib content of all formulations was between 95-105% of the theoretical concentration. The peak purity of all formulations was greater than 99% and comparable to the peak purity at t=0, with the exception of SS5 at 40° C. which was 98.58% and slightly lower than the t=0 value of 99.85%. Thus, the formulations are stable at room temperature (20-25° C.) and up to 40° C. for at least about 4 weeks.

Example 5

Skin Irritation of Exemplary Patidegib Topical Formulations

Skin irritation of three exemplary formulations prepared as described in Example 1 was assessed in Gottingen minipigs. The test formulations were:
1. "SS22, 3.5 wt % patidegib", and comprising ethanol, benzyl alcohol, isostearic acid and propylene glycol, and HPC as a gelling agent;
2. "SS14, low PG, 4.0 wt % patidegib", and comprising Transcutol P, ethanol, propylene glycol, buffer (pH 7.5; boric acid and sodium hydroxide) and phenoxyethanol and HPC as a gelling agent;
3. "SS14, 4.0 wt % patidegib", and comprising Transcutol P, ethanol, propylene glycol, buffer (pH 7.5; boric acid and sodium hydroxide) and phenoxyethanol and HPC as a gelling agent;
4. SS22 placebo—same as formulation 1. above with no patidegib;
5. SS14, low PG placebo—same as formulation 2. above with no patidegib;
6. SS14 placebo—same as formulation 3. above with no patidegib;

In three minipigs, six application sites were identified; 3 sites on each side of the midline of the dorsal region of each animal. Each application measured 2×2 inches and the sites were marked at the corners with an indelible marker. Prior to administration, the hair was clipped from the back of each animal. Each test article and placebo (1 mL/site) was distributed over the prescribed area by gentle in junction with a stainless steel spatula for 14 consecutive days. The test article was applied evenly with a thin, uniform film and the area was not occluded. For the initial dose, the material was applied in 0.25-0.5 mL/kg increments until the maximum feasible volume was identified to be 1 mL/kg application. Beginning on Day 2, the dosing sites were gently wiped with a wiping cloth (WYPALL®) wet with tap water to remove any residual material.

Daily observations of the test sites on each pig were made. For the SS22 formulation, very slight erythema was noted in ⅔ pigs beginning on Day 2. This progressed to well-defined to moderate-to-server incidences of the course of the 14 days. By Day 14, very slight to moderate-to-severe erythema was present in all animals. Because the same observations were made for the test and placebo SS22 test articles (numbers 1 and 4 above), the erythema may be vehicle related rather than drug related. For the SS14 formulations (numbers 2, 3, 5 and 6 above), no erythema or edema was noted at any time point on either the active or placebo test sites.

Example 6

Combination Solvent Systems for Topical Administration of a Hedgehog Inhibitor

The hedgehog inhibitor compound itraconazole and the following solvent systems were prepared as topical formulations. The solvent systems were devised following solubility experiments in which the saturated solubility of itraconazole in various solvents after a minimum of 24 hours stirring at 25° C. was investigated. Itraconazole is highly insoluble in water. However, following initial solubility experiments, itraconazole was found to exhibit a solubility between 0.01-0.05% w/w in dimethicone 350 CST, diisopropyl adipate, ethanol and castor oil; in dimethyl isosorbide, itraconazole exhibits a solubility of 2.32% w/w. A higher solubility was observed in benzyl alcohol and phenoxyethanol, of 14.97% and 7.87% w/w, respectively. Itraconazole demonstrated a saturated solubility in N-methyl pyrrolidone of 7.65% w/w. For the remaining solvents in which itraconazole solubility was investigated (not shown), the drug possessed a solubility between 0.01-0.20% w/w. Following several screening studies in which various mixed solvent systems were explored to assess solubility, system compatibility, and storage stability of itraconazole, the following optimized non-aqueous formulations were prepared.

TABLE 5-A

| Excipient | Theoretical composition (%, w/w) | | | | | |
|---|---|---|---|---|---|---|
| | SS36-I | SS37-I | SS38-I | SS40-I | SS42-I | SS43-I |
| Phenoxyethanol | — | 1 | — | — | — | — |
| Benzyl alcohol | 5 | — | 5 | 5 | 5 | 5 |
| diethylene glycol monoethyl ether | 25 | 25 | 25 | — | 25 | 25 |
| Ethanol | 53.9 | 57.9 | 48.9 | 48.9 | 28.9 | 23.9 |
| PEG 400 | — | — | — | 25 | — | — |
| N-methyl pyrrolidone* | — | — | — | — | 25 | 25 |
| dimethylisosorbide | 15 | 15 | 15 | 15 | 15 | 15 |
| Propylene Carbonate | — | — | 5 | 5 | — | 5 |
| Butylated hydroxytoluene (BHT) | 0.1 | 0.1 | 0.1 | 0.1 | 0.1 | 0.1 |
| Mean itraconazole saturated solubility (%, w/w, lowest-highest value of n = 3) | 0.34 (0.23-0.42) | 0.16 (0.12-0.19) | 0.34 (0.30-0.39) | 0.33 (0.30-0.37) | 0.76 (0.72-0.78) | 0.86 (0.85-0.88) |
| Mean itraconazole % area/area (lowest-highest value of n = 3) | 100.00 (100.00-100.00) | 100.00 (100.00-100.00) | 100.00 (100.00-100.00) | 100.00 (100.00-100.00) | 100.00 (100.00-100.00) | 100.00 (100.00-100.00) |
| Apparent pH of solvent system with itraconazole | 7.14 | 7.03 | 6.79 | 8.24 | 7.44 | 7.61 |

*N-methyl-2-pyrrolidone, also known as N-methyl pyrrolidone, is sold under the trade name Pharmasolve ™.

TABLE 5-B

| Excipient | Theoretical composition (%, w/w) | | | | | | |
|---|---|---|---|---|---|---|---|
| | SS44-I | SS45-I | SS46-I | SS47-I | SS48-I | SS49-I | SS50-I |
| Phenoxyethanol | — | — | 1 | — | — | — | — |
| Benzyl alcohol | 5 | 5 | — | 5 | 5 | 5 | 5 |
| diethylene glycol monoethyl ether | 25 | 25 | 25 | 25 | 25 | 25 | 25 |
| Ethanol | 53.9 | 53.9 | 32.9 | 23.9 | 23.9 | — | — |
| Glycerol | — | — | — | — | 10 | 10 | 10 |
| Propylene glycol | — | — | — | — | 20 | 20 | 20 |
| PEG 400 | — | 15 | — | 15 | — | 23.9 | 18.9 |
| N-methyl-2-pyrrolidone | — | — | 25 | 25 | — | — | — |
| Dimethyl isosorbide | 15 | — | 15 | — | 15 | 15 | 15 |
| Propylene Carbonate | — | — | — | 5 | — | — | 5 |
| Butylated hydroxytoluene | — | 0.1 | 0.1 | 0.1 | 0.1 | 0.1 | 0.1 |
| Butylated hydroxyanisol (BHA) | 0.1 | — | — | — | — | — | — |
| Mean itraconazole saturated solubility (%, w/w, lowest-highest value of n = 3) | 0.25 (0.22-0.27) | 0.14 (0.13-0.15) | 0.67 (0.64-0.69) | 0.59 (0.58-0.59) | 0.23 (0.22-0.24) | 0.27 (0.26-0.29) | 0.32 (0.31-0.33) |
| Mean itraconazole % area/area (lowest-highest value of n = 3) | 100.00 (100.00-100.00) | 100.00 (100.00-100.00) | 100.00 (100.00-100.00) | 100.00 (100.00-100.00) | 100.00 (100.00-100.00) | 100.00 (100.00-100.00) | 100.00 (100.00-100.00) |
| Apparent pH of solvent system with itraconazole | 7.04 | 8.88 | 7.33 | 9.26 | 6.8 | 7.7 | 7.61 |

The solubility of itraconazole in all of the additional solvent systems generated (SS36-J to SS50-) was between about 0.24-0.86% w/w of itraconazole, with the exception of SS37 and SS45 where the solubility was approximately 0.15% w/w of itraconazole. Topical formulations of itraconazole will generally contain from about 0.10 w/w % itraconazole to about 10 w/w % itraconazole, or more typically will contain from about 0.10 w/w % itraconazole to about 5 w/w % itraconacole, or more typically from about 0.1-2 weight percent itraconazole.

Example 7
Non-Aqueous Gels for Topical Administration of a Hedgehog Inhibitor

Following the exploration and identification of the mixed solvent systems identified in Tables 5A and 5B, and following acceptable four week compatibility results, non-aqueous gels based on the formulations described in Example 6 were prepared. The gel formulations were slightly viscous to highly viscous gels, with viscosity increasing with the amount of HPC in the solvent system (e.g., from 1% to 2% w/w). Based upon initial formulation experiments, the gelling agents Carbopol 980 and hydroxypropyl methylcellulose appeared to be incompatible with itraconazole and the solvent systems employed, with a white precipitate forming during formulation.

TABLE 6-A

Representative Non-aqueous gels for Topical Administration

| Excipient | SS36-IG 1% HPC P | SS37-IG 1% HPC P | SS38-IG 1% HPC P | SS40 1% HPC P | SS42-IG 1% HPC P | SS43-IG 1% HPC P |
|---|---|---|---|---|---|---|
| Phenoxyethanol | — | 1 | — | — | — | — |
| Benzyl alcohol | 5 | — | 5 | 5 | 5 | 5 |
| diethylene glycol monoethyl ether | 25 | 25 | 25 | — | 25 | 25 |
| Ethanol | 53.9 | 57.9 | 48.9 | 48.9 | 28.9 | 23.9 |
| PEG 400 | — | — | — | 25 | — | — |
| N-methyl-2-pyrrolidone | — | — | — | — | 25 | 25 |
| Dimethyl isosorbide | 15 | 15 | 15 | 15 | 15 | 15 |
| Propylene Carbonate | — | — | 5 | 5 | — | 5 |
| Butylated hydroxytoluene (BHT) | 0.1 | 0.1 | 0.1 | 0.1 | 0.1 | 0.1 |
| Hydroxypropylcellulose | 1 | 1 | 1 | 1 | 1 | 1 |
| Apparent pH | 7.03 | 7.06 | 7.24 | 8.31 | 7.74 | 7.84 |

TABLE 6-B

Representative Non-Aqueous Gels for Topical Administration

| Excipient | SS44-IG 1% HPC P | SS45-IG 1% HPC P | SS46-IG 1% HPC P | SS47-IG 1% HPC P | SS48-IG 1% HPC P | SS49-IG 1% HPC P | SS50-IG 1% HPC P |
|---|---|---|---|---|---|---|---|
| Phenoxyethanol | — | — | 1 | — | — | — | — |
| Benzyl alcohol | 5 | 5 | — | 5 | 5 | 5 | 5 |
| diethylene glycol monoethyl ether | 25 | 25 | 25 | 25 | 25 | 25 | 25 |
| Ethanol | 53.9 | 53.9 | 32.9 | 23.9 | 23.9 | — | — |
| Glycerol | — | — | — | — | 10 | 10 | 10 |
| Propylene glycol | — | — | — | — | 20 | 20 | 20 |
| PEG 400 | — | 15 | — | 15 | — | 23.9 | 18.9 |
| N-methyl-2-pyrrolidone | — | — | 25 | 25 | — | — | — |
| Dimethyl isosorbide | 15 | — | 15 | — | 15 | 15 | 15 |
| Propylene Carbonate | — | — | — | 5 | — | — | 5 |
| Butylated hydroxytoluene | — | 0.1 | 0.1 | 0.1 | 0.1 | 0.1 | 0.1 |
| Butylated hydroxyanisole | 0.1 | — | — | — | — | — | — |
| Hydroxypropyl-cellulose | 1 | 1 | 1 | 1 | 1 | 1 | 1 |
| Apparent pH | 7.07 | 8.93 | 7.89 | 9.28 | 6.68 | 7.70 | 7.61 |

A representative active gel comprising itraconazole with 1.5% HPC and 0.15% itraconazole was successfully formulated, forming a medium viscosity gel with no appearance of itraconazole crystals when observed under a microscope. Placebo gels were prepared for solvent systems SS36-IG to SS50-IG and containing HPC at 1% w/w. In all cases, the gels prepared were slightly hazy with a low to medium viscosity which flowed when tilted, with the exception of SS49 and SS50 which possessed a medium viscosity.

Example 8

Short-Term Stability of Non-Aqueous Gels for Topical Administration of a Hedgehog Inhibitor A total of 16 formulations (including the corresponding placebos) were prepared for short-term stability testing. The representative formulations contain 2% w/w HPC (in contrast to the formulations above which contain 1% w/w HPC), and comprise from 0.1% w/w to about 1.0% w/w itraconazole. Only 14 of the 16 formulations prepared were placed on stability at 25 and 40° C. (and an additional temperature of 2-8° C.) in borosilicate glass vials, with the compositions of active formulations outlined in the tables below. The following tests were performed at each time point: 0, 2 and 4 weeks, for the assessment of the formulations placed on stability: visual appearance (macroscopic and microscopic appearance), apparent pH, and itraconazole content and peak purity.

Macroscopic Appearance

The formulations were visually assessed. At t=0, all active and placebo itraconazole gels were observed to be uniform, colourless with a high viscosity. Following 2 and 4 weeks storage at 25 and 40° C. all formulations were observed to be unchanged from t=0.

Microscopic Appearance

All formulations were assessed under the light microscope at 200 and 400× magnification and compared to their respective placebo formulations. Crystallisation was not observed in any of the active formulations at t=0 or following 2 and 4 weeks storage at 25 and 40° C.

Apparent pH

At t=0 the apparent pH of the itraconazole formulations was measured. The active itraconazole formulations possessed apparent pH values between 7.49 and 9.59 at t=0. Since all of the formulations placed on stability were non-aqueous based, the pH values are only "apparent pH" values, where the pH meter was standardized by use of an aqueous buffer solution. For the pH of the non-aqueous solutions, the ionization constant of the acid or base, the dielectric constant of the medium, the liquid junction potential (which may give rise to errors of 1 pH unit) and the hydrogen ion response of the glass electrode are all charged, giving rise to the "apparent pH", which for the current purpose is to monitor any pH changes during the stability program. After 2 weeks stored at 25 and 40° C., the apparent pH values of active and placebo formulations were relatively comparable to t=0 where the apparent pH values showed a small decrease in pH (up to 0.5 pH units). After 4 weeks storage at 25 and 40° C. the apparent pH remained relatively comparable to t=2 weeks and t=0, with the final pH reading of each formulation falling within 0.5 pH units of t=0, with the exception of SS43-IG which was within 0.7 pH units of the initial pH reading.

Itraconazole Content and Peak Purity

The formulations were analysed for itraconazole content. Itraconazole content for all of the active formulations prepared for short term stability was 95-102% of the theoretical concentration. Peak purity of the itraconazole formulations at t=0 were all >99.39%. After 2 weeks storage at 25 and 40° C., the recovery and peak purity of all formulations were comparable to t=0, with the exception of SS33 at both temperatures and SS46-SS50 at 40° C. where a slight decrease in itraconazole recovery (approx. 92-96%) was observed. After 4 weeks storage at 25 and 40° C., the recovery of all formulations was observed to be between 95-100% of the theoretical concentration and comparable to t=0, with the exception of SS33 which showed a minimal decrease of between 4-5% from 102% to 98 and 97% at 25 and 40° C., respectively. The peak purity of all itraconazole formulations after 4 weeks storage at 25 and 4° C. were >99.4%, and comparable to the peak purity at t=0.

TABLE 7A

Active formulations placed on stability

Theoretical composition (%, w/w)

| Excipient | SS36-IG2 2% HPC 0.18% Itr A | SS37-IG2 2% HPC 0.10% Itr A | SS38-IG2 2% HPC 0.25% Itr A | SS40-IG2 2% HPC 0.25% Itr A | SS42-IG2 2% HPC 0.55% Itr A | SS43-IG2 2% HPC 0.70% Itr A | SS33-IG2 2% HPC 0.25% Itr A |
|---|---|---|---|---|---|---|---|
| Phenoxyethanol | — | 1.00 | — | — | — | — | — |
| Benzyl alcohol | 5.00 | — | 5.00 | 5.00 | 5.00 | 5.00 | 5.00 |
| diethylene glycol monoethyl ether | 25.00 | 25.00 | 25.00 | — | 25.00 | 25.00 | 25.00 |
| Ethanol | 52.72 | 56.80 | 47.65 | 47.65 | 27.35 | 22.20 | 30.65 |
| Propylene glycol | — | — | — | — | — | — | 20.00 |
| Solutol | — | — | — | — | — | — | 2.00 |
| PEG 400 | — | — | — | 25.00 | — | — | — |
| N-methyl-2-pyrrolidone | — | — | — | — | 25.00 | 25.00 | — |
| Dimethyl isosorbide | 15.00 | 15.00 | 15.00 | 15.00 | 15.00 | 15.00 | 15.00 |
| Propylene carbonate | — | — | 5.00 | 5.00 | — | 5.00 | — |
| Butylated hydroxytoluene | 0.10 | 0.10 | 0.10 | 0.10 | 0.10 | 0.10 | 0.10 |

TABLE 7A-continued

Active formulations placed on stability

Theoretical composition (%, w/w)

| Excipient | SS36-IG2 2% HPC 0.18% Itr A | SS37-IG2 2% HPC 0.10% Itr A | SS38-IG2 2% HPC 0.25% Itr A | SS40-IG2 2% HPC 0.25% Itr A | SS42-IG2 2% HPC 0.55% Itr A | SS43-IG2 2% HPC 0.70% Itr A | SS33-IG2 2% HPC 0.25% Itr A |
|---|---|---|---|---|---|---|---|
| Hydroxypropyl-cellulose | 2.00 | 2.00 | 2.00 | 2.00 | 2.00 | 2.00 | 2.00 |
| Itraconazole (API) | 0.18 | 0.1 | 0.25 | 0.25 | 0.55 | 0.7 | 0.25 |
| Total | 100.00 | 100.00 | 100.00 | 100.00 | 100.00 | 100.00 | 100.00 |

TABLE 7B

Active Formulations Placed on Stability

Theoretical composition (%, w/w)

| Excipient | SS44-IG2 2% HPC 0.18% Itr A | SS45-IG2 2% HPC 0.10% Itr A | SS46-IG2 2% HPC 0.50% Itr A | SS47-IG2 2% HPC 0.50% Itr A | SS48-IG2 2% HPC 0.18% Itr A | SS49-IG2 2% HPC 0.20% Itr A | SS50-IG2 2% HPC 0.25% Itr A |
|---|---|---|---|---|---|---|---|
| Phenoxyethanol | — | — | 1.00 | — | — | — | — |
| Benzyl alcohol | 5.00 | 5.00 | — | 5.00 | 5.00 | 5.00 | 5.00 |
| diethylene glycol monoethyl ether | 25.00 | 25.00 | 25.00 | 25.00 | 25.00 | 25.00 | 25.00 |
| Ethanol | 52.72 | 52.80 | 31.40 | 22.40 | 22.72 | — | — |
| Propylene glycol | — | — | — | — | 20.00 | 19.80 | 19.75 |
| Glycerol | — | — | — | — | 10.00 | 10.00 | 10.00 |
| PEG 400 | — | 15.00 | — | 15.00 | — | 22.90 | 17.90 |
| N-methyl-2-pyrrolidone | — | — | 25.00 | 25.00 | — | — | — |
| Dimethyl isosorbide | 15.00 | — | 15.00 | — | 15.00 | 15.00 | 15.00 |
| Propylene carbonate | — | — | — | 5.00 | — | — | 5.00 |
| Butylated hydroxytoluene | — | 0.10 | 0.10 | 0.10 | 0.10 | 0.10 | 0.10 |
| Hydroxypropyl-cellulose | 2.00 | 2.00 | 2.00 | 2.00 | 2.00 | 2.00 | 2.00 |
| Itraconazole (API) | 0.18 | 0.1 | 0.5 | 0.5 | 0.18 | 0.2 | 0.25 |
| Total | 100.00 | 100.00 | 100.00 | 100.00 | 100.00 | 100.00 | 100.00 |

Formulations selected for additional permeation/penetration experiments include SS37-IG2, SS38-IG2, SS-40-IG2, SS-43-IG2 and SS-50-IG2, based on solubility of itraconazole, solvent compatibility, apparent pH, and drug stability.

Example 9

Permeation/Penetration of Topical Formulations of Itraconazole

A permeation/skin penetration study was conducted based on formulations SS37-IG2, SS38-IG2, SS-40-IG2, SS-43-G2 and SS-50-G2, with sampling time points t=0, 14, 18, 24, 26, 36, 40, 44, and 48 hours following the same protocol as described in Example 1.

Components of each representative topical formulation are described below.

TABLE 8-01

Topical Formulation SS37-IG2

| Component | w/w % | |
|---|---|---|
| ethanol | 56.80 | w/w ratio EtOH + phenoxyethanol/DEGMEE 2.3 |
| diethylene glycol monoethyl ether | 25.00 | |
| Dimethyl isosorbide | 15.00 | w/w ratio DEGMEE/DMI 1.7 |
| phenoxyethanol | 1.00 | |
| hydroxypropyl cellulose | 2.00 | |
| Butylated hydroxytoluene | 0.10 | |
| itraconazole | 0.10 | |

TABLE 8-02

Topical Formulation SS38-IG2

| Component | w/w % | |
|---|---|---|
| ethanol | 47.65 | w/w ratio EtOH + benzyl alcohol/DEGMEE 2.11 |
| diethylene glycol monoethyl ether | 25.00 | |
| Dimethyl isosorbide | 15.00 | w/w ratio DEGMEE/DMI 1.7 |
| Benzyl alcohol | 5.00 | |
| Propylene carbonate | 5.00 | |
| hydroxypropyl cellulose | 2.00 | |
| Butylated hydroxytoluene | 0.10 | |
| itraconazole | 0.25 | |

TABLE 8-03

Topical Formulation SS40-1G2

| Component | w/w % | |
|---|---|---|
| ethanol | 47.65 | w/w ratio EtOH + benzyl alcohol/PEG-400 2.11 |
| PEG-400 | 25.00 | |
| Dimethyl isosorbide | 15.00 | w/w ratio PEG/DMI 1.7 |
| Benzyl alcohol | 5.00 | |
| Propylene carbonate | 5.00 | |
| hydroxypropyl cellulose | 2.00 | |
| Butylated hydroxytoluene | 0.10 | |
| itraconazole | 0.25 | |

TABLE 8-04

Topical Formulation SS43-IG2

| Component | w/w % | |
|---|---|---|
| diethylene glycol monoethyl ether | 25.00 | |
| N-methyl pyrrolidone | 25.00 | |
| ethanol | 22.20 | w/w ratio EtOH + benzyl alcohol/DEGMEE 1.1 |
| Dimethyl isosorbide | 15.00 | w/w ratio DEGMEE/DMI 1.7 |
| Benzyl alcohol | 5.00 | |
| Propylene carbonate | 5.00 | |
| hydroxypropyl cellulose | 2.00 | |
| Butylated hydroxytoluene | 0.10 | |
| itraconazole | 0.70 | |

TABLE 8-05

Topical Formulation SS50-IG2

| Component | w/w % | |
|---|---|---|
| diethylene glycol monoethyl ether | 25.00 | w/w ratio ternary solvent system PPG, PEG, glycerol + benzyl alcohol/DEGMEE 2.12 |
| Propylene glycol | 19.75 | |
| PEG-400 | 17.90 | |
| Dimethyl isosorbide | 15.00 | w/w ratio DEGMEE/DMI 1.7 |
| Glycerol | 10.00 | |
| Propylene carbonate | 5.00 | |
| Benzyl alcohol | 5.00 | |
| hydroxypropyl cellulose | 2.00 | |
| Butylated hydroxytoluene | 0.10 | |
| itraconazole | 0.25 | |

FIG. 4 and FIG. 5 illustrate the results obtained from the full scale permeation and penetration experiments of itraconazole, respectively. The data generated in the penetration experiment was utilized to determine the concentration achieved in the *Stratum corneum*, epidermis and dermis summarized in Table 9. Given that the half maximal inhibitory concentration (IC50) for itraconazole is 0.8 µM, the tissue concentration of itraconazole is adequate to achieve a cellular response.

TABLE 9

Summary of concentration of itraconazole in each of the skin matrices (*Stratum corneum*, epidermis, dermis) (µM) after the final time point (48 h).

| Formulation | Concentration of itraconazole (µM) in *Stratum corneum*. | Concentration of itraconazole (µM) in epidermis. | Concentration of itraconazole (µM) in dermis |
|---|---|---|---|
| SS37-IG2 (Test Item 1) | 1819.6436 | 39.0019 | 10.3957 |
| SS38-IG2 (Test Item 2) | 2086.3566 | 100.7848 | 11.9649 |
| SS40-IG2 (Test Item 3) | 1151.2386 | 14.8867 | 6.7681 |
| SS43-IG2 (Test Item 4) | 4660.0911 | 118.9332 | 34.8528 |
| SS50-IG2 (Test Item 5) | 2122.1240 | 49.4327 | 18.6353 |

FIG. 4 provides the cumulative amount of itraconazole permeated through human skin over a 48 hour time period for each of the test items. Formulations demonstrating the highest cumulative amount of itraconazole permeation were formulations SS50-IG2 and SS-43-IG2; these formulations exhibited the highest cumulative amount of itraconazole permeation at each of the time points evaluated, with SS-50 IG2 demonstrating the greatest overall skin permeation of itraconazole at each of the time points evaluated.

FIG. 5 provides information regarding recovery of itraconazole from each of the skin matrices (*stratum corneum*, epidermis, dermis) and receiver fluid, in nanograms, following the final 48 hour time point. SS-43-IG2 exhibited superior penetration into the *stratum corneum*, with notable levels of drug in both the epidermis and dermis as well.

Based upon a consideration of numerous factors including solubility of itraconazole, solvent system compatibility, apparent pH, formulation stability, and in-vitro skin permeation, representative preferred formulations include SS43-IG2, SS50-IG2 and SS38-IG2.

Example 10

Preparation of an Illustrative Itraconazole Topical Gel Formulation

A non-aqueous topical formulation of itraconazole was prepared as follows. Dehydrated ethanol was added to the formulation vessel, followed by addition of butylated hydroxytoluene (BHT) to the formulation vessel until dissolution. To the mixture was added diethylene glycol monoethyl ether (Transcutol® P), followed by N-methyl-2-pyrrolidone (Pharmasolve™). Dimethyl isosorbide was then added, followed by addition of propylene carbonate, and benzyl alcohol. The mixture was stirred by propeller until uniform. To the uniform mixture was added itraconazole until dissolved. Hydroxypropylcellulose was then added accompanied by propeller stirring. Once the HPC addition was complete, the resulting mixture was stirred until the HPC was fully dispersed. The exemplary formulation contains 0.7% w/w itraconazole.

A total single dose full face application of approximately 125 mg of gel corresponds to approximately 0.7 mg of itraconazole.

TABLE 10

| Material | Supplier | Grade | Formula (% w/w) | Quantity per 30 g Tube Fill (g) |
|---|---|---|---|---|
| Itraconazole | Letco Medical Decatur, AL | USP | 0.7 | 0.21 |
| Dehydrated alcohol | Spectrum New Brunswick, NJ | USP | 22.2 | 6.66 |
| Butylated hydroxytoluene | Spectrum New Brunswick, NJ | NF | 0.1 | 0.03 |
| Diethylene glycol monoethyl ether (Transcutol P) | Gattefosse Paramus, NJ | NF | 25.0 | 7.50 |
| N-methyl-2-pyrrolidone (Pharmasolve) | Ashland Wilmington, DE | JP | 25.0 | 7.50 |
| Dimethyl isosorbide (Arlasolve DMI-LQ) | Croda Edison, NJ | ≥98.0% | 15.0 | 4.50 |
| Propylene carbonate | Penta Fairfield, NJ | NF | 5.0 | 1.50 |
| Benzyl alcohol | Spectrum New Brunswick, NJ | NF | 5.0 | 1.50 |
| Hydroxylpropyl-cellulose, (Klucel HF Pharm) | Ashland Wilmington, DE | NF | 2.0 | 0.60 |

Example 11

In Vivo Administration of Patidegib Via Topical Delivery

A study was conducted to determine the toxicokinetics of patidegib and its metabolite, IPI-230, when patidegib was administered twice daily (approximately 8 hours apart) to Gottingen Minipigs® via dermal application for 13 weeks.

The formulation identified herein as SS14 was prepared, with 2% patidegib and with 4% patidegib. A placebo formulation was also prepared that was identical in all respects to SS14 except for the absence of the patidegib. The formulation was applied topically to the animals at patidegib dose levels of 0 mg/kg/day (untreated), 0 mg/kg/day (placebo), 40 mg/kg/day, and 80 mg/kg/day to Groups 1, 2, 3, and 4, respectively. Groups 1 and 3 consisted of four animals/sex/group and Groups 2 and 4 consisted of six animals/sex/group. Doses were administered twice daily (approximately 8 hours apart). Blood samples were collected from all animals, survival permitting, on Days 1, 14 (Group 4 only), and 90 predose and at approximately 2, 4, 6, 8 (just prior to the second daily dose), 10, 12, 14, 16, and 24 hours following the first daily dose. Plasma samples were assayed for patidegib and IPI-230. Only the 2-hour samples from the untreated and placebo groups were analyzed.

| | No. of Animals | | Approximate Dose Patidegib |
|---|---|---|---|
| Group | Male | Female | (mg/kg/day)[a] |
| 1 (Untreated) | 4 | 4 | 0 |
| 2 (Placebo) | 6 | 6 | 0 |
| 3 (2% Patidegib) | 4 | 4 | 40 |
| 4 (4% Patidegib) | 6 | 6 | 80 |

[a] Dose levels calculated assuming a test article density of 1 g/mL at an application rate of 2 mL/kg/day (1 mL/kg/dose) and based on an average body weight of 14 kg.

Noncompartmental analysis was applied to the individual plasma patidegib and IPI-230 concentration data for males and females. The following parameters were estimated: $C_{max}$—Maximum observed concentration; $T_{max}$—Time of maximum observed concentration; $AUC_{Tlast}$—Area under the concentration-time curve from hour 0 to the last measurable concentration, estimated by the linear trapezoidal rule; $AUC_{0-24}$—Area under the concentration-time curve from hour 0 to hour 24, estimated by the linear trapezoidal rule; DN $AUC_{0-24}$—Dose normalized $AUC_{0-24}$, calculated as $AUC_{0-24}$/dose level; DN $C_{max}$—Dose normalized $C_{max}$, calculated as $C_{max}$/dose level. Some of the data is summarized in the tables below.

TABLE 11-1

Summary of the Mean Patidegib $C_{max}$ and $AUC_{0-24}$ in Gottingen Minipig® Plasma

| Interval | Dose Group | Dose Level (mg/kg/day) | Sex | $C_{max}$ (ng/mL) | $AUC_{0-24}$ (ng · hr/mL) |
|---|---|---|---|---|---|
| Day 1 | 3 | 40 | F | 4.65 | 56.7 |
| | 4 | 80 | M | 3.84 | 37.7 |
| | | | F | 4.03 | 36.3 |
| | | | MF | 3.93 | 37.1 |
| Day 14 | 4 | 80 | M | 88.7 | 1390 |
| | | | F | 410 | 6820 |
| | | | MF | 249 | 4110 |
| Day 90 | 3 | 40 | M | 8.68 | 132 |
| | | | F | 35.0 | 526 |
| | | | MF | 21.9 | 329 |
| | 4 | 80 | M | 21.4 | 352 |
| | | | F | 141 | 2310 |
| | | | MF | 75.8 | 1240 |

Notes:

Doses were administered twice daily approximately 8 hours apart.

Due to limited concentration data above the lower limit of quantitation in males, only females are presented for Day 1 at 40 mg/kg/day.

TABLE 11-2

Summary of the Mean IPI-230 $C_{max}$ and $AUC_{0-24}$ in Gottingen Minipig ®Plasma

| Interval | Dose Group | Patidegib Dose Level (mg/kg/day) | Sex | $C_{max}$ (ng/mL) | $AUC_{0-24}$ (ng · hr/mL) |
|---|---|---|---|---|---|
| Day 14 | 4 | 80 | M | 1.56[a] | 27.2[a] |
|  |  |  | F | 3.47 | 61.2 |
|  |  |  | MF | 3.15 | 55.5 |
| Day 90 | 4 | 80 | M | 0.567[a] | 3.35* |
|  |  |  | F | 1.64 | 25.5 |
|  |  |  | MF | 1.28 | 18.1 |

Note:
Doses were administered twice daily approximately 8 hours apart.
*Value is not a mean (N = 1) and is presented for informational purposes only.

The mean concentration-time profiles of patidegib in plasma for the test groups (male and female results combined) are presented graphically in FIG. 6A and the mean concentration-time profiles of IPI-230 in plasma for the test groups (male and female results combined) are presented graphically in FIG. 6B. The dose normalized $C_{max}$ and $AUC_{0-24}$ relationships of patidegib in Gottingen Minipig® plasma are presented graphically in for the combined sexes in FIGS. 7A-7B.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

It is claimed:

1. A composition for intradermal delivery, comprising: patidegib and a solvent system comprising (i) a monohydric primary alcohol and a polyol in a w/w ratio of between about 0.9-1.8 and (ii) a buffer, wherein patidegib is present in the solvent system between about 0.1-10 wt %.

2. The composition of claim 1, wherein the monohydric primary alcohol is of the form R—OH, where R is selected from methyl, ethyl, propyl, butyl, and pentyl.

3. The composition of claim 1, wherein the polyol is selected from propylene glycol, dipropylene glycol, hexylene glycol, 1,3-butylene glycol, liquid polyethylene glycols.

4. The composition of claim 1, wherein the solvent system further comprises diethylene glycol monoethyl ether.

5. The composition of claim 4, wherein the composition further comprises a gelling agent.

6. The composition of claim 5, wherein the gelling agent is hydroxypropylcellulose.

7. The composition of claim 6, wherein the composition further comprises a preservative.

8. The composition of claim 7, wherein the preservative is phenoxyethanol.

9. The composition of claim 1, comprising: patidegib and a solvent system comprising (i) ethanol and propylene glycol in a w/w ratio of between about 0.9-1.8, (ii) diethylene glycol monoethyl ether, and (iii) a buffer, wherein patidegib is present in the solvent system in an amount between about 0.1-10 wt %.

10. The composition of claim 9, wherein the composition further comprises a gelling agent.

11. The composition of claim 10, wherein the gelling agent is hydroxypropylcellulose.

12. The composition of claim 11, wherein the composition further comprises a preservative.

13. The composition of claim 12, wherein the preservative is phenoxyethanol.

14. The composition of claim 1, wherein the patidegib has a saturation solubility in the solvent system of between about 2.5-8 wt % and wherein formulation provides an in vitro concentration of patidegib in the dermis of greater than about 50 µM 48 hours after topical application.

15. A topical delivery system, comprising an intradermal composition according to claim 1.

16. The topical delivery system of claim 15, further comprising a backing member and membrane joined to define a reservoir in which the composition is contained.

17. The topical delivery system of claim 16, wherein the membrane is a non-rate controlling membrane.

18. A method for treating basal cell carcinoma, comprising:
    topically applying a topical delivery system according to claim 15 to a subject in need thereof, whereby said topically applying achieves intracutaneous delivery of patidegib in an amount sufficient for treating basal cell carcinoma, with a non-therapeutic concentration of the compound present in the blood of the subject.

19. The method of claim 18, wherein the subject has Gorlin syndrome.

20. A method for treating basal cell carcinoma, comprising: topically applying a composition according to claim 1 to a subject in need thereof, whereby said topically applying achieves intracutaneous delivery of patidegib in an amount sufficient for treating basal cell carcinoma, with a non-therapeutic concentration of the compound present in the blood of the subject.

21. The method of claim 20, wherein the subject has Gorlin syndrome.

* * * * *